(12) United States Patent
Zhao et al.

(10) Patent No.: US 12,297,284 B2
(45) Date of Patent: May 13, 2025

(54) ANTI-TNFR2 ANTIBODY AND USE THEREOF

(71) Applicants: JIANGSU SIMCERE PHARMACEUTICAL CO., LTD., Nanjing (CN); SIMCERE BIO-PHARMACEUTICAL TECHNOLOGY., LTD., Nanjing (CN)

(72) Inventors: Xinyan Zhao, Nanjing (CN); Xiaofeng Zhao, Nanjing (CN); Shiqiang Lu, Nanjing (CN); Ran Pang, Nanjing (CN); Xinxin Li, Nanjing (CN); Jinsheng Ren, Nanjing (CN)

(73) Assignees: JIANGSU SIMCERE PHARMACEUTICAL CO., LTD., Nanjing (CN); SIMCERE BIO-PHARMACEUTICAL TECHNOLOGY., LTD., Nanjing (CN)

( * ) Notice: Subject to any disclaimer, the term of this patent is extended or adjusted under 35 U.S.C. 154(b) by 962 days.

(21) Appl. No.: 17/295,773

(22) PCT Filed: Jul. 31, 2020

(86) PCT No.: PCT/CN2020/106057
§ 371 (c)(1),
(2) Date: May 20, 2021

(87) PCT Pub. No.: WO2021/023098
PCT Pub. Date: Feb. 11, 2021

(65) Prior Publication Data
US 2022/0017630 A1 Jan. 20, 2022

(30) Foreign Application Priority Data
Aug. 2, 2019 (CN) .......................... 201910713742.1

(51) Int. Cl.
*C07K 16/28* (2006.01)
*A61P 35/00* (2006.01)
*G01N 33/574* (2006.01)
*A61K 39/00* (2006.01)

(52) U.S. Cl.
CPC .......... *C07K 16/2878* (2013.01); *A61P 35/00* (2018.01); *C07K 16/2818* (2013.01); *C07K 16/2827* (2013.01); *G01N 33/57492* (2013.01); *A61K 2039/505* (2013.01); *A61K 2039/507* (2013.01); *C07K 2317/24* (2013.01); *C07K 2317/34* (2013.01); *C07K 2317/732* (2013.01); *C07K 2317/76* (2013.01); *C07K 2317/92* (2013.01); *G01N 2333/7151* (2013.01)

(58) Field of Classification Search
CPC ............ C07K 16/2878; C07K 16/2818; C07K 16/2827; C07K 2317/24; C07K 2317/34; C07K 2317/732; C07K 2317/76; C07K 2317/92; A61P 35/00; G01N 33/57492; G01N 2333/7151; A61K 2039/505; A61K 2039/507
See application file for complete search history.

(56) References Cited

U.S. PATENT DOCUMENTS

| | | |
|---|---|---|
| 2018/0194850 A1 | 7/2018 | Faustman |
| 2019/0144556 A1 | 5/2019 | Faustman |

FOREIGN PATENT DOCUMENTS

| | | | | |
|---|---|---|---|---|
| CN | 107849142 A | | 3/2018 | |
| CN | 109476745 A | * | 3/2019 | ..... A61K 39/001117 |
| WO | 2016/187068 A1 | | 11/2016 | |
| WO | 2017/083525 A1 | | 5/2017 | |
| WO | 2017/197331 A2 | | 11/2017 | |
| WO | 2017/220711 A1 | | 12/2017 | |
| WO | 2019/094559 A2 | | 5/2019 | |
| WO | 2020/102739 A1 | | 5/2020 | |

OTHER PUBLICATIONS

Sampson, JF et. al. "A novel human TNFR2 antibody (MM-401) modulates T cell responses in anti-cancer immunity", Cancer Res, 2019, 79. (Year: 2019).*
Stancovski, I et. al. "Mechanistic aspects of the opposing effects of monoclonal antibodies to the ERBB2 receptor on tumor growth", 1991, Proc. Natl. Acad. Sci., 88, 8691-8695. (Year: 1991).*
Jiang, B et. al. "A Novel Peptide Isolated from a Phage Display Peptide Library with Trastuzumab Can Mimic Antigen Epitope of HER-2", 2005, The Journal of Biological Chemistry, 280(6), 4656-4662. (Year: 2005).*
Rudikoff et al., "Single Amino Acid Substitution Altering Antigen-Binding Specificity," *PNAS* 79:1979-1983, 1982.
Heinrich et al., "Comparison of the results obtained by ELISA and surface plasmon resonance for the determination of antibody affinity," *Journal of Immunological Methods* 352:13-22, 2010.
Hu et al., "Comparison of Surface Plasmon Resonance, Resonant Waveguide Grating Biosensing and Enzyme Linked Immunosorbent Assay (ELISA) in the Evaluation of a Dengue Virus Immunoassay," *Biosensors* 3:297-311, 2013.

* cited by examiner

*Primary Examiner* — Nelson B Moseley, II
*Assistant Examiner* — Alyssa Rae Stonebraker
(74) *Attorney, Agent, or Firm* — Seed IP Law Group LLP

(57) ABSTRACT

Provided is an antibody or an antigen-binding fragment thereof capable of specifically binding to TNFR2, wherein the antibody or the antigen-binding fragment thereof is capable of regulating the function of immune cells and may be used as a medicament to treat diseases related to immune-related disorders, such as tumors. A polynucleotide encoding the antibody or antigen-binding fragment thereof and a pharmaceutical composition comprising the antibody or antigen binding fragment thereof are also provided.

12 Claims, 28 Drawing Sheets
Specification includes a Sequence Listing.

| TGI (%) | Day | 24 | 26 | 28 |
|---|---|---|---|---|
| Anti-mTNFR2 | G2 vs. G1 | 62.6* | 63.2 *** | 58.4 **** |
| Anti-mPD-1 | G3 vs. G1 | 35.9 | 39.1 * | 31.5* |
| Anti-mTNFR2 + anti-mPD-1 | G4 vs. G1 | 83.0** | 85.0 **** | 88.5 **** |

*: $p < 0.05$, : $p < 0.01$, *: $p < 0.001$, ****: $p < 0.0001$, vs. G1 Veh, Two-way ANOVA, N=9

ANTI-TNFR2 ANTIBODY AND USE THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 500044_405USPC_SEQUENCE LISTING.txt. The text file is 49.8 KB, was created on May 17, 2021, and is being submitted electronically via EFS-Web.

The present application claims the benefits of Chinese patent application No. 201910713742.1 filed on Aug. 2, 2019, the entire contents of which are incorporated by reference herein in their entirety.

FIELD OF THE INVENTION

The invention relates to an anti-TNFR2 antibody or antigen binding fragment thereof, a pharmaceutical composition comprising the TNFR2 antibody or antigen binding fragment thereof, and a use thereof.

BACKGROUND OF THE INVENTION

Immunity is a protective response of the body, which is affected by many genes, proteins and cells Immune abnormalities can cause many diseases, including tumors, immune deficiency (such as AIDS), allergies and rheumatoid arthritis. In the past few years, tumor immunotherapy, as a brand-new treatment method, has become a hot spot in the field of tumor therapy research. Antagonistic antibodies that target immune checkpoint proteins, such as anti-PD-1 and anti-CTLA-4 monoclonal antibodies, have been used to treat various types of cancers and have achieved revolutionary results, greatly prolonging the survival period of patients with malignant tumors. However, there are still many cancer patients who do not respond to the treatment of antagonistic antibodies against immune checkpoint proteins or develop resistance or drug resistance after short-term treatment. Therefore, it is necessary to develop new drugs for the treatment of cancer, which can be used alone or in combination with other tumor treatment methods, and antagonistic antibodies containing immune checkpoint proteins are used in combination to further improve the efficacy and safety.

SUMMARY OF THE INVENTION

The inventors found that human TNFR2 was overexpressed on the surface of human Treg and various human tumor cells, suggesting that human TNFR2 may promote tumorigenesis in patients and mediate immunosuppression and immune escape of tumor microenvironment.

It may be a very potential anti-tumor strategy to regulate the function of Treg cells through TNFR2 to inhibit the occurrence of tumors. The inventors prepared an antagonistic antibody against TNFR2, which could 1) specifically bind to TNFR2, block the binding of TNFR2 to the ligand TNFα, therefore inhibiting the proliferation of Treg cells and inhibitory function mediated by the Treg cells, and promoting the expansion of T cells and the anti-tumor function mediated by T cells and other immune cells. In addition, 2) due to the high expression of TNFR2 in human tumor cell lines, the antibody could also directly mediate the killing effect on tumor cells with high expression of TNFR2.

The inventors also found that the potential function of TNFR2 was further verified in relevant experiments in mice. The results show that TNFR2 antagonistic antibody, compared with PD-1 antibody or PD-L1 monoclonal antibody, can significantly inhibit the growth of PD-1 antibody-resistant tumors, reduce the size of tumors, effectively increase the ratio of $CD8^+T$/Treg and partially reverse the immunodepletion of $CD8^+T$ cells in a mouse colorectal cancer CT26 model. Therefore, TNFR2 may become a new target for tumor immunotherapy. TNFR2 antagonistic antibody is expected to help change tumor microenvironment, and can be used alone and/or in combination with existing immune checkpoint antagonistic antibodies, thus having a wide application prospect. For this reason, the inventors prepared a variety of TNFR2 antibodies and completed the present invention thereon.

In a first aspect, the present disclosure provides an antibody or antigen-binding fragment thereof which specifically binds to TNFR2, and which is capable of regulating the function of immune cells, including Treg cells and/or MDSC, and be used as a drug to treat diseases related to immune abnormalities, e.g., tumors.

In one embodiment, the regulating comprises inhibiting the proliferation and/or activation of Treg cells and/or myeloid derived suppressor cell (MDSC). In another embodiment, the regulating is achieved by blocking the binding of TNFα to TNFR2.

In a specific embodiment, the antibody or antigen binding fragment thereof comprises:
(1) heavy chain CDR combinations of CDR1-VH, CDR2-VH and CDR3-VH,
the CDR1-VH, CDR2-VH and CDR3-VH have any sequence combination selected from the group consisting of the following or sequence combinations having 1, 2, 3 or more amino acid insertions, deletions and/or substitutions compared to the sequence combination:

|      | SEQ ID NO. | | |
| --- | --- | --- | --- |
| No. | CDR1-VH | CDR2-VH | CDR3-VH |
| VH1  | 26  | 27  | 28  |
| VH2  | 38  | 39  | 40  |
| VH3  | 50  | 51  | 52  |
| VH4  | 62  | 63  | 64  |
| VH5  | 74  | 75  | 76  |
| VH6  | 86  | 87  | 88  |
| VH7  | 98  | 99  | 100 |
| VH8  | 110 | 111 | 112 |
| VH9  | 122 | 123 | 124 |
| VH10 | 134 | 135 | 136 |
| VH11 | 146 | 147 | 148 |
| VH12 | 23  | 24  | 25  |
| VH13 | 35  | 36  | 37  |
| VH14 | 47  | 48  | 49  |
| VH15 | 59  | 60  | 61  |
| VH16 | 71  | 72  | 73  |
| VH17 | 83  | 84  | 85  |
| VH18 | 95  | 96  | 97  |
| VH19 | 107 | 108 | 109 |
| VH20 | 119 | 120 | 121 |
| VH21 | 131 | 132 | 133 |
| VH22 | 143 | 144 | 145 | and/or,
(2) light chain CDR combinations of CDR1-VL, CDR2-VL and CDR3-VL,
the CDR1-VL, CDR2-VL and CDR3-VL have any sequence combination selected from the group consisting of the following or sequence combinations having 1, 2, 3 or more amino acid insertions, deletions and/or substitutions compared to the sequence combination:

|        | SEQ ID NO. | | |
| --- | --- | --- | --- |
| Number | CDR1-VL | CDR2-VL | CDR3-VL |
| VL1  | 32  | 33  | 34  |
| VL2  | 44  | 45  | 46  |
| VL3  | 56  | 57  | 58  |
| VL4  | 68  | 69  | 70  |
| VL5  | 80  | 81  | 82  |
| VL6  | 92  | 93  | 94  |
| VL7  | 104 | 105 | 106 |
| VL8  | 116 | 117 | 118 |
| VL9  | 128 | 129 | 130 |
| VL10 | 140 | 141 | 142 |
| VL11 | 152 | 153 | 154 |
| VL12 | 29  | 30  | 31  |
| VL13 | 41  | 42  | 43  |
| VL14 | 53  | 54  | 55  |
| VL15 | 65  | 66  | 67  |
| VL16 | 77  | 78  | 79  |
| VL17 | 89  | 90  | 91  |
| VL18 | 101 | 102 | 103 |
| VL19 | 113 | 114 | 115 |
| VL20 | 125 | 126 | 127 |
| VL21 | 137 | 138 | 139 |
| VL22 | 149 | 150 | 151. |

In particular, the antibody or antigen binding fragment thereof of the present invention comprises, e.g., a combination of the heavy chain CDRs and light chain CDRs selected from the group consisting of VH1+VL1, VH2+VL2, VH3+VL3, VH4+VL4, VH5+VL5, VH6+VL6, VH7+VL7, VH8+VL8, VH9+VL9, VH10+VL10, VH11+VL11, VH12+VL12, VH13+VL13, VH14+VL14, VH15+VL15, VH16+VL16, VH17+VL17, VH18+VL18, VH19+VL19, VH20+VL20, VH21+VL21 and VH22+VL22, and CDR combinations having 1, 2, 3 or more amino acid insertions, deletions and/or substitutions compared with the combination of the heavy chain CDRs and light chain CDRs.

In another specific embodiment, the present invention provides such antibody or antigen binding fragment thereof, wherein
1) a heavy chain variable region and a light chain variable region have the sequence shown in SEQ ID NO: 1 and SEQ ID NO: 2, respectively, or the sequence having 70%, 75%, 80%, 85%, 90%, 95%, 96%, 97%, 98%, 99% or higher consistency with the sequence shown;
2) a heavy chain variable region and a light chain variable region have the sequence shown in SEQ ID NO: 3 and SEQ ID NO: 4, respectively, or the sequence having 70%, 75%, 80%, 85%, 90%, 95%, 96%, 97%, 98%, 99% or higher consistency with the sequence shown;
3) a heavy chain variable region and a light chain variable region have the sequence shown in SEQ ID NO: 5 and SEQ ID NO: 6, respectively, or the sequence having 70%, 75%, 80%, 85%, 90%, 95%, 96%, 97%, 98%, 99% or higher consistency with the sequence shown;
4) a heavy chain variable region and a light chain variable region have the sequence shown in SEQ ID NO: 7 and SEQ ID NO: 8, respectively, or the sequence having 70%, 75%, 80%, 85%, 90%, 95%, 96%, 97%, 98%, 99% or higher consistency with the sequence shown;
5) a heavy chain variable region and a light chain variable region have the sequence shown in SEQ ID NO: 9 and SEQ ID NO: 10, respectively, or the sequence having 70%, 75%, 80%, 85%, 90%, 95%, 96%, 97%, 98%, 99% or higher consistency with the sequence shown;
6) a heavy chain variable region and a light chain variable region have the sequence shown in SEQ ID NO: 11 and SEQ ID NO: 12, respectively, or a sequence having 70%, 75%, 80%, 85%, 90%, 95%, 96%, 97%, 98%, 99% or higher consistency with the sequence shown;
7) a heavy chain variable region and a light chain variable region have the sequence shown in SEQ ID NO: 13 and SEQ ID NO: 14, respectively, or a sequence having 70%, 75%, 80%, 85%, 90%, 95%, 96%, 97%, 98%, 99% or higher consistency with the sequence shown;
8) a heavy chain variable region and a light chain variable region have the sequence shown in SEQ ID NO: 15 and SEQ ID NO: 16, respectively, or a sequence having 70%, 75%, 80%, 85%, 90%, 95%, 96%, 97%, 98%, 99% or higher consistency with the sequence shown;
9) a heavy chain variable region and a light chain variable region have the sequence shown in SEQ ID NO: 17 and SEQ ID NO: 18, respectively, or a sequence have 70%, 75%, 80%, 85%, 90%, 95%, 96%, 97%, 98%, 99% or higher consistency with the sequence shown;
10) a heavy chain variable region and a light chain variable region have the sequence shown in SEQ ID NO: 19 and SEQ ID NO: 20, respectively, or a sequence have 70%, 75%, 80%, 85%, 90%, 95%, 96%, 97%, 98%, 99% or higher consistency with the sequence shown; or
11) a heavy chain variable region and a light chain variable region have the sequence shown in SEQ ID NO: 21 and SEQ ID NO: 22, respectively, or have 70%, 75%, 80%, 85%, 90%, 95%, 96%, 97%, 98%, 99% or higher consistency with the sequence shown.

In a preferred embodiment, the antibody or antigen-binding fragment thereof of the present invention has a dissociation constant (KD) of not more than 5 nM for binding to human TNFR2 and not more than 5 nM for binding to cynomolgus TNFR2.

In a preferred embodiment, the antibody or antigen binding fragment thereof of the present invention is chimeric or humanized or fully human antibody or antigen binding fragment.

In a preferred embodiment, the antibody or antigen binding fragment thereof of the present invention comprises a constant region selected from the group consisting of human IgG1, IgG2, IgG3, IgG4, IgA, IgM, IgE and IgD, and the antibody or antigen binding fragment:
1) specifically binds to cells that express TNFR2 on cell surface;
2) specifically binds to Treg cells;
3) inhibits the binding of TNFα to TNFR2 protein;
4) inhibits the binding of TNFα to TNFR2 expressed on the cell surface;
5) inhibits TNFα-mediated Treg proliferation and/or Treg function;
6) mediates ADCC function against TNFR2-expressing cell; or/and
7) inhibits tumor growth.

In another preferred embodiment, the antigen binding fragment of the present invention is selected from the group consisting of F(ab)$_2$, Fab', Fab, Fv, scFv, bispecific antibodies, nano antibodies, and antibody minimum recognition units.

In another embodiment, the antibody or antigen binding fragment thereof of the present invention may compete with the antibody selected from the group consisting of numbers 001, 088, 125, 133, 219, 224, 226, 309, 352, 365 and 395 for binding to TNFR2.

In a second aspect, the present invention provides a polynucleotide encoding the antibody or antigen binding fragment thereof or any combination thereof as described in the first aspect above.

In a third aspect, the present invention provides an expression vector comprising the polynucleotide as described in the second aspect above.

In a fourth aspect, the present invention provides a cell comprising the expression vector as described in the third aspect above. The cell is, e.g., prokaryotic or eukaryotic cells, including Chinese hamster ovary cells, yeast cells, insect cells, Escherichia coli and Bacillus subtilis.

In a fifth aspect, the present invention provides a pharmaceutical composition comprising the antibody or antigen binding fragment thereof as described in the first aspect above, the polynucleotide as described in the second aspect, the expression vector as described in the third aspect, or the cell as described in the fourth aspect, and a pharmaceutically acceptable carrier.

In one embodiment, the pharmaceutical composition of the present invention further comprises additional anti-tumor agents. The additional anti-tumor agents are, e.g., selected from the group consisting of chemotherapeutic agents, targeted therapeutic agents and immunotherapy agents, e.g., anti-PD-1/PD-L1 therapeutic agents (including anti-PD-1 antibodies and anti-PD-L1 antibodies) and anti-CTLA-4 therapeutic agents (including anti-CTLA-4 antibodies).

In a sixth aspect, the present invention provides a kit comprising the antibody or antigen binding fragment thereof as described in the first aspect above, the polynucleotide as described in the second aspect, the expression vector as described in the fourth aspect, or the cell as described in the fourth aspect, and instructions for use.

In the seventh aspect, the present invention provides a method for treating and/or preventing immune abnormality-related diseases, the method comprising administering to a subject in need the antibody or antigen binding fragment thereof as described in the first aspect, the polynucleotide as described in the second aspect, the expression vector as described in the third aspect, the cell as described in the fourth aspect, or the pharmaceutical composition as described in the fifth aspect. The immune abnormality-related diseases are, e.g., immune abnormality diseases characterized by sTNFR2 abnormalities, including diseases related to Treg cell and/or MDSC function, in particular a tumor.

In one embodiment, the method of the present invention further comprises administering to the subject additional anti-tumor therapy, including chemotherapy, radiotherapy, targeted therapy and immunotherapy, e.g., anti-PD-1/PD-L1 therapy such as anti-PD-1/PD-L1 antibody, anti-CTLA-4 therapy such as anti-CTLA-4 antibody.

In one embodiment, the related disease is a tumor, preferably selected from:
1) ovarian cancer, advanced epidermal T cell lymphoma, stage III/IV metastatic colorectal cancer, triple negative breast cancer and/or pancreatic cancer; or,
2) metastatic melanoma or other possible advanced solid tumor resistant to CTLA-4 and PD-1 therapy.

In an eighth aspect, the present invention provides a drug product corresponding to the method described in the seventh aspect above, which is used in the preventive and/or therapeutic method described in the seventh aspect. In addition, the present invention provides a use for preparing a drug or kit corresponding to the method described in the seventh aspect, wherein the product according to the first to fifth aspects above is used for manufacturing, and the drug or kit is used in the preventive and/or therapeutic method described the seventh aspect above.

In a ninth aspect, the present invention provides a method for detecting sTNFR2, which comprises contacting a sample suspected of containing sTNFR2 with the antibody or antigen binding fragment thereof of the first aspect. The detection method can be used for diagnosing immune abnormality diseases characterized by sTNFR2 abnormalities, e.g., diagnosing whether a sample source subject suffers from immune abnormality-related diseases (such as Treg cell and/or MDSC function-related diseases) or is at risk of onset. Accordingly, the present invention also provides a use of a reagent for detecting sTNFR2 to prepare a kit for diagnosing whether a sample source subject suffers from an immune abnormality-related disease (such as an immune abnormality disease related with TNFR2 expression abnormality) or is at a risk of onset.

BRIEF DESCRIPTION OF THE DRAWINGS

The abovementioned aspects and other aspects of the invention will be clearly explained by the following detailed description of the invention and the accompanying drawings. The drawings are provided to illustrate some preferred embodiments of the invention, however, it is to be understood that the invention is not limited to the particular embodiments disclosed.

FIG. 2 shows the extent of TNFR2 expression on Treg, $CD8^+$ T cells and $CD4^+CD25^-$Tcon cells of human peripheral blood mononuclear cells (PBMC).

FIG. 3 shows the binding of the test antibodies to CHO cells that overexpress human TNFR2 (CHO-TNFR2).

FIG. 4 shows the binding ability of the test antibodies on Treg cells.

FIG. 8A shows the proliferation of Treg cells after 3 days of culture without cytokine, or with IL-2 alone, or with IL-2 and TNFα. FIG. 8B shows the inhibitory effect of different antibodies on TNFα-induced Treg proliferation. The ordinate shows different antibodies, the abscissa shows (inhibitory ability of each antibody on TNFα-induced Treg proliferation−inhibitory ability of the control antibody on TNFα-induced Treg proliferation)/inhibitory ability of the control antibody on TNFα-induced Treg proliferation×100%, the control antibody is anti-Hel antibody, and the experimental concentration of each antibody is 12.5 μg/ml.

FIG. 10 shows the antibody-dependent cellular cytotoxicity (ADCC) killing effect of the test antibodies of the invention against Treg.

DETAILED DESCRIPTION OF THE INVENTION

Figure 1:
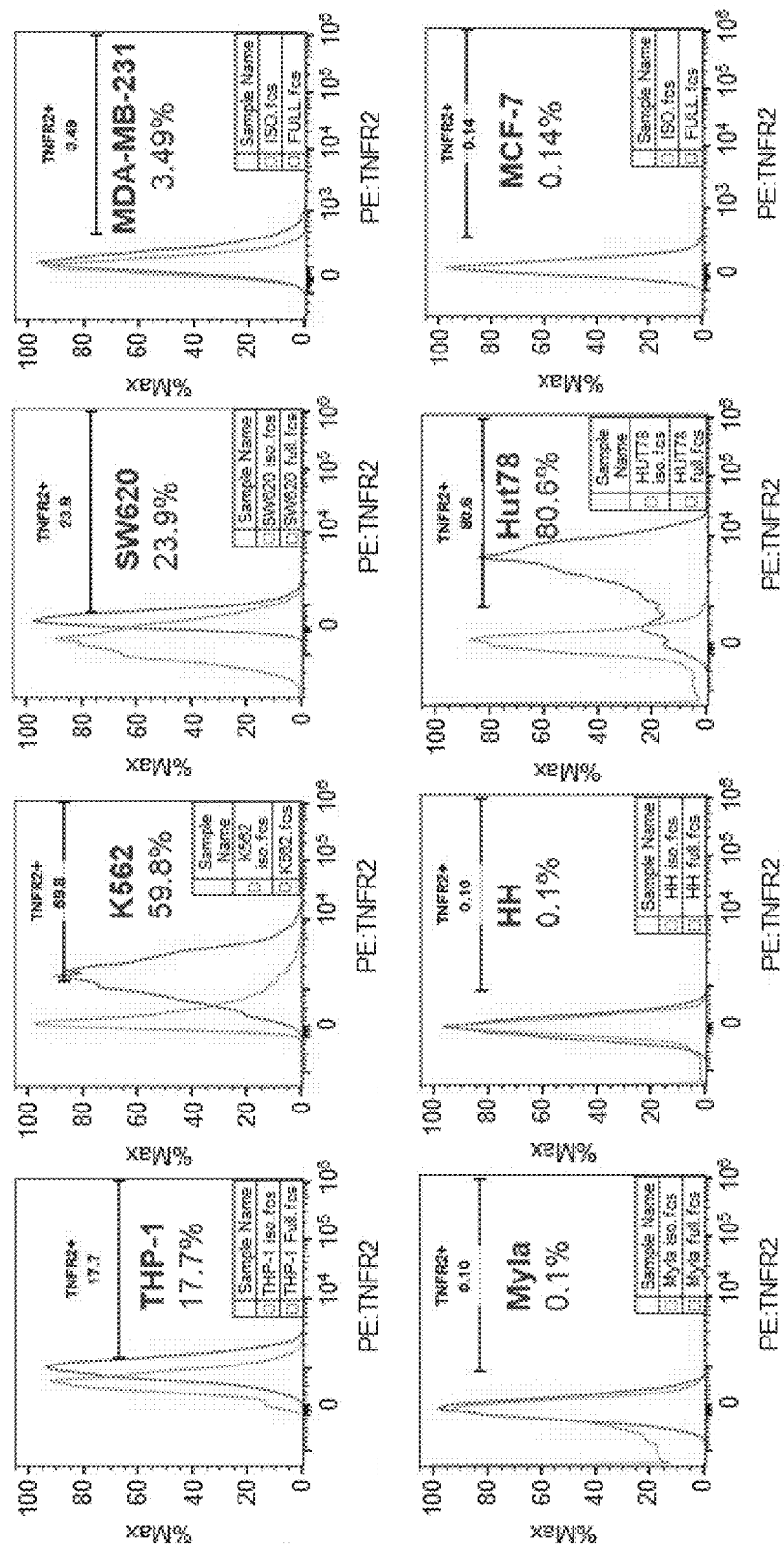
FIG. 1 shows the extent of TNFR2 expression in 13 human tumor cell lines. The positive ratio is determined according to the detection value of the matched isotype control antibody after flow cytometry fluorescence sorting (FACS) staining, and the percentage shown in the figure is the expression percentage of TNFR2.
Figure 1:
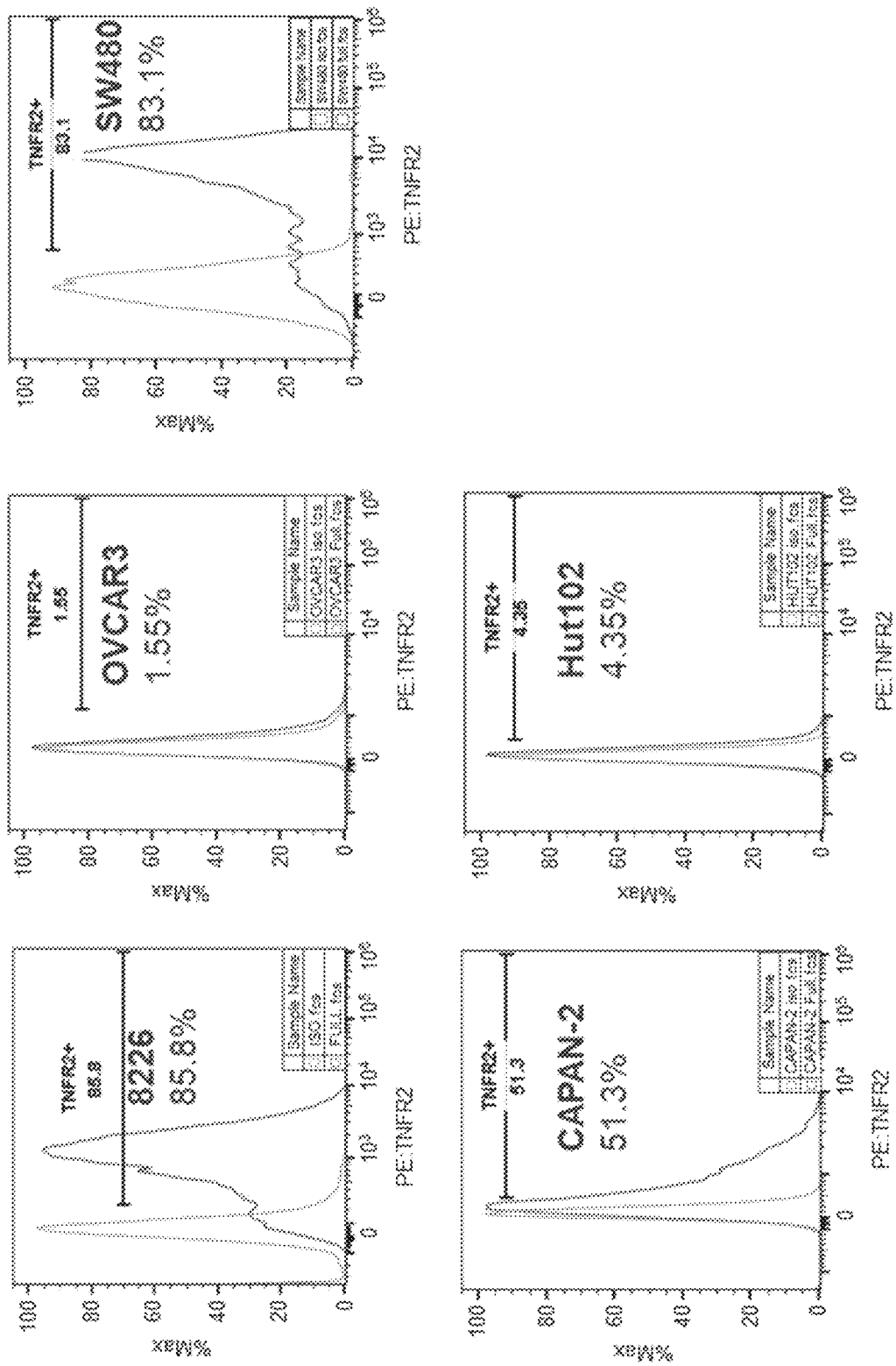

As use herein, unless otherwise stated, terms have meanings commonly understood by those skilled in the art. For a term expressly defined herein, the meaning of the term shall be subject to the definition.

As use herein, the term "antibody" (Ab) refers to an immunoglobulin molecule that specifically binds to, or is immunologically reactive with, a particular antigen, and includes polyclonal, monoclonal, genetically engineered and otherwise modified forms of antibodies (including but not limited to chimeric antibodies, humanized antibodies, fully human antibodies, heteroconjugated antibodies (e.g., bi-, tri-, and quad-specific antibodies, diabodies, triabodies and tetrabodies), antibody conjugates) and antigen binding fragments of antibodies (including, e.g., Fab', F(ab')2, Fab, Fv, rIgG and scFv fragments). Moreover, unless otherwise stated, the term "monoclonal antibody" (mAb) is meant to include both intact molecules, as well as, antibody fragments (e.g., Fab and F(ab')2 fragments) that are capable of specifically binding to a target protein. Fab and F(ab')2 fragments lack Fc fragments of an intact antibody, clear more rapidly from the circulation of the animal and therefore lack Fc-mediated effector function (see Wahl et al., J. Nucl. Med. 24: 316, 1983; incorporated herein by reference).

As use herein, the term "antigen-binding fragment" refers to one or more fragments of an antibody that retain the ability to specifically bind to a target antigen. The antigen-binding function of an antibody can be performed by fragments of a full-length antibody. The antibody fragments can be a Fab, F(ab')2, scFv, SMIP, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the VL, VH, CL and CH domains; (ii) a F(ab)2 fragment, a bivalent fragment comprising two Fab fragments linked by a disulfide bridge at the hinge region; (iii) a Fab fragment consisting of the VH and CH domains; (iv) a Fv fragment consisting of the VL and VH domains of a single arm of an antibody; (V) a dAb including VH and VL domains; (vi) a dAb fragment consisting of a VH domain (Ward et al., Nature 341: 544-546, 1989); (vii) a dAb consisting of a VH or a VL domain; (viii) an isolated complementary determinant region (CDR); and (ix) a combination of two or more isolated CDRs which may optionally be joined by synthetic linkers. Furthermore, although the two domains of the Fv fragment, VL and VH, are coded by separate genes, they can be joined, using a recombinant method, by a linker that enables them to be made as a single protein chain in which the VL and VH domain pair to form monovalent molecules (known as single-chain Fv (scFv); see e.g., Bird et al., Science 242: 423-426, 1988, and Huston et al., Proc. Natl. Acad. Sci. USA 85: 5879-5883, 1988). These antibody fragments can be obtained using conventional techniques known to those skilled in the art, and the fragments can be screened for utility in the same manner as intact antibodies. Antigen-binding fragments may be produced by recombinant DNA techniques, enzymatic or chemical cleavage of intact immunoglobulins, or, in some embodiment, by chemical peptide synthesis procedures known in the art.

As use herein, the term "TNFR2" refers to tumor necrosis factor receptor 2, also refers to tumor necrosis factor receptor superfamily member 1B (TNFRSF1B) or CD120b, which is a membrane receptor that binds to tumor necrosis factor-α (TNFα). The TNFR2 is preferably a human TNFR2.

As use herein, the terms "anti-tumor necrosis factor receptor 2 antibody", "tumor necrosis factor receptor 2 antibody", "anti-TNFR2 antibody", "TNFR2 antibody", "anti-TNFR2 antibody portion" and/or "anti-TNFR2 antibody fragment" and the like refer to any protein- or peptide-containing molecule that includes at least a portion of an immunoglobulin molecule (for example but not limited to at least one complementarity determining region (CDR) of a heavy or light chain or a ligand binding portion thereof, a heavy chain or light chain variable region, a heavy chain or light chain constant region, a framework region or any portion thereof), that is capable of specifically binding to TNFR2. TNFR2 antibodies also include antibody-like protein scaffolds (e.g. the 10th fibronectin type III domain (10Fn3)), which contains BC, DE and FG structural loops similar in structure and solvent accessibility to antibody CDRs. The tertiary structure of the 10Fn3 domain resembles that of the variable region of the IgG heavy chain, and one of skill in the art can graft, e.g., the CDRs of a TNFR2 monoclonal antibody onto the fibronectin scaffold by replacing residues of the BC, DE and FG loops of 10Fn3 with residues from the CDR-H1, CDR-H2 or CDR-H3 regions of the TNFR2 monoclonal antibody.

As use herein, the term "bispecific antibody" refers to monoclonal, often human or humanized antibodies that have binding specificities for at least two different antigens. In the invention, one of the binding specificities can be directed towards an antigenic epitope of TNFR2, and the other can be directed towards another antigenic epitope of TNFR2 or any other antigen, e.g., for a cell-surface protein, receptor, receptor subunit, tissue-specific antigen, virally derived protein, virally encoded envelope protein, bacterially derived protein, or bacterial surface protein, etc.

As use herein, the term "chimeric" antibody refers to an antibody having variable sequences derived from an immunoglobulin of one source organism, such as rat or mouse, and constant regions derived from an immunoglobulin of a different organism (e.g., a human). Methods for producing chimeric antibodies are known in the art. See, e.g., Morrison, 1985, Science 229 (4719): 1202-7; Oi et al., 1986, Bio Techniques 4: 224-221; Gillies et al., 1985 J Immunol Methods 125: 191-202; incorporated herein by reference.

As use herein, the term "complementarity determining region" (CDR) refer to a hypervariable region found both in the light chain and heavy chain variable domains. The more highly conserved portions of variable domains are called the framework regions (FRs). As is appreciated in the art, the amino acid positions that delineate a hypervariable region of an antibody can vary, depending on the context and the various definitions known in the art. Some positions within a variable domain may be reviewed as hybrid hypervariable positions in that these positions can be deemed to be within a variable region under one set of criteria (such as IMGT or KABAT) while being deemed to be outside a variable region under a different set of criteria (such as KABAT or IMGT). One or more of these positions can also be found in extended variable regions. The invention includes antibodies comprising modifications in these hybrid variable positions. The variable domains of native heavy and light chains each comprise four framework regions that primarily adopt a β-sheet configuration, connected by three CDRs (CDR1, CDR2 and CDR3), which form loops that connect, and in some cases form part of, the β-sheet structure. The CDRs in each chain are held together in close proximity by the FR region in the order FR1-CDR1-FR2-CDR2-FR3-CDR3-FR4 and, with the CDRs from the other antibody chains, contribute to the formation of antigen binding sites of the antibody (see Kabat et al., Sequences of Proteins of Immunological Interest, National Institute of Health, Bethesda, Md. 1987; incorporated herein by reference). As use herein, e.g., CDR1-VH, CDR2-VH and CDR3-VH refer to a first CDR, a second CDR and a third CDR of a heavy chain variable region (VH), respectively, which constitute a combination of CDRs (VHCDR combination) of a heavy chain (or variable region thereof); CDR1-VL, CDR2-VL and CDR3-VL refer to a first CDR, a second CDR and a third CDR of a light chain variable region (VL), respectively, which constitute a combination of CDRs (VLCDR combination) of the light chain (or variable region thereof).

As use herein, the term "antibody conjugate" refers to a conjugate formed by chemical bonding of an antibody molecule to another molecule, either directly or through a linker, e.g. an antibody-drug conjugate (ADC), wherein the drug molecule is the abovementioned another molecule.

As use herein, the term "monoclonal antibody" refers to an antibody derived from a single clone (including any eukaryotic, prokaryotic, or phage clone), and is not limited to the method by which it is produced.

As use herein, the term "VH" refers to the variable region of an immunoglobulin heavy chain of an antibody (including the heavy chain of an Fv, scFv, or Fab). The term "VL" refers to the variable region of an immunoglobulin light chain (including the light chain of an Fv, scFv, dsFv or Fab).

As use herein, the term "regulatory T cells" or "Treg", also referred to as suppressor T cells, are a group of lymphocytes that negatively regulate the body's immune response to maintain tolerance to autoantigens, control immune overreaction, avoid immune damage to normal cells, and prevent the occurrence of autoimmune diseases. Treg expresses the following biomarkers: CD4, FOXP3 and CD25, which are believed to originate from the same germline as immature CD47 cells. Treg plays an extremely important role in the occurrence of tumors. Many studies have shown that the number of Treg cells in tumor microenvironment has increased significantly, including melanoma, ovarian cancer, breast cancer, colon cancer, lung cancer, pancreatic cancer, etc. In the meantime, the number of Treg cells is also closely related to the survival rate of tumor patients. In addition, tumor cells can induce the proliferation of tumor infiltrating Treg cells. Proliferated Treg cells secrete a large amount of immunosuppressive factors such as TGF-β, inhibit the functions of immune cells such as $CD8^+T$ cells, and block the killing effect of immune cells on tumors. It is an important drug resistance mechanism for the failure of immunotherapy for various solid tumors and hematological tumors. Recent studies have shown that immune tolerance of PD-1/PD-L1 and other immunotherapy patients is also closely related to Treg.

As use herein, the term "myeloid-derived suppressor cell" or "MDSC" refers to a heterogeneous cell population of the immune system composed of immature neutrophils, monocytes and dendritic cells, which has the effect of inhibiting immune response and tumor immune response. MDSC modulates the activity of various effector cells and antigen presenting cells (such as T cells, NK cells, dendritic cells, macrophages, etc.). Myeloid-derived suppressor cells are characterized by their gene expression profile, which express all or a subset of proteins and small molecules selected from the group consisting of B7-1 (CD80), B7-H1 (PD-L1), CCR2, CD1d, CD1d1, CD2, CD31 (PECAM-I), CD43, CD44, complement component C5aR1, F4/80 (EMR1), FcγRIII (CD16), FcγRII (CD32), FcγRIIA (CD32b), FcγRIIB/C (CD32b/c), FcγRIIC (CD32c), FcγRIIIA (CD16A), FcγRIIIB (CD16b), galactin-3, GP130, Gr-1(Ly-6G), ICAM-1(CD54), IL-1RI, IL-4Ra, IL-6Ra, integrin a4(CD49d), integrin aL (CD11a), integrin aM (CD11b), M-C SFR, MGL1(CD301a), MGL1/2(CD301a/b), MGL2(CD301b), nitric oxide, PSGL-1(CD162), L-selectin (CD62L), siglec-3(CD33), transferrin receptor (TfR), VEGFR1(Flt-I) and VEGFR2(KDR or Flk-1). In particular, MDSC does not express proteins selected from the group consisting of B7-2 (CD86), B7-H4, CD11c, CD14, CD21, CD23 (FcεRII), CD34, CD35, CD40 (TNFRSF5), CD117 (c-kit), HLA-DR, and Sca-I (Ly6).

As use herein, The term "percent (%) sequence consistency" refers to the percentage of amino acid (or nucleic acid) residues of a candidate sequence that are identical to the amino acid (or nucleic acid) residues of a reference sequence after aligning the sequences and introducing gaps, if necessary, to achieve the maximum percent sequence identity (e.g., gaps can be introduced in one or both of the candidate and reference sequences for optimal alignment and non-homologous sequences can be disregarded for comparison purposes). Alignment for purposes of determining percent sequence identity can be achieved in various ways that are within the skill in the art, for instance, using publicly available computer software, such as BLAST, ALIGN, or Megalign (DNASTAR) software. Those skilled in the art can determine appropriate parameters for measuring alignment, including any algorithms needed to achieve maximal alignment over the full length of the sequences being compared. For example, a reference sequence aligned for comparison with a candidate sequence may show that the candidate sequence exhibits from 50% to 100% sequence identity across the full length of the candidate sequence or a selected portion of contiguous amino acid (or nucleic acid) residues of the candidate sequence. The length of the candidate sequence aligned for comparison purposes may be, e.g., at least 30%, (e.g., 30%, 40, 50%, 60%, 70%, 80%, 90%, or 100%) of the length of the reference sequence. When a position in the candidate sequence is occupied by the same amino acid residue as the corresponding position in the reference sequence, then the molecules are identical at that position.

As use herein, the term "specifically binds" refers to a binding reaction which is determinative of the presence of an antigen in a heterogeneous population of proteins and other biological molecules that is recognized, e.g., by an antibody or antigen-binding fragment thereof, with particularity. An antibody or antigen-binding fragment thereof that specifically binds to an antigen will bind to the antigen with a KD of less than 100 nM. For example, an antibody or antigen-binding fragment thereof that specifically binds to an antigen will bind to the antigen with a KD of up to 100 nM (e.g., between 1 pM and 100 nM). An antibody or antigen-binding fragment thereof that does not exhibit specific binding to a particular antigen or epitope thereof will exhibit a KD of greater than 100 nM (e.g., greater than 500 nm, 1 µM, 100 µM, 500 µM, or 1 mM) for that particular antigen or epitope thereof. A variety of immunoassay formats may be used to select antibodies specifically immunoreactive with a particular protein or carbohydrate. For example, solid-phase ELISA immunoassays are routinely used to select antibodies specifically immunoreactive with a protein or carbohydrate. See, Harlow & Lane, Antibodies, A Laboratory Manual, Cold Spring Harbor Press, New York (1988) and Harlow & Lane, Using Antibodies, A Laboratory Manual, Cold Spring Harbor Press, New York (1999), for a description of immunoassay formats and conditions that can be used to determine specific immunoreactivity.

As use herein, the term "vector" includes a nucleic acid vector, e.g., a DNA vector, such as a plasmid, a RNA vector, virus or other suitable replicon (e.g., viral vector). A variety of vectors have been developed for the delivery of polynucleotides encoding exogenous proteins into a prokaryotic or eukaryotic cell. Expression vectors of the invention contain a polynucleotide sequence as well as, e.g., additional sequence elements used for the expression of proteins and/or the integration of these polynucleotide sequences into the genome of a mammalian cell. Certain vectors that can be used for the expression of antibodies and antibody fragments of the invention include plasmids that contain regulatory sequences, such as promoter and enhancer regions, which direct gene transcription. Other useful vectors for expression of antibodies and antibody fragments contain polynucleotide sequences that enhance the rate of translation of these genes or improve the stability or nuclear export of the mRNA that results from gene transcription. These sequence elements include, e.g., 5' and 3' untranslated regions, an internal ribosomal entry site (IRES), and polyadenylation signal site in order to direct efficient transcription of the gene carried on the expression vector. The expression vectors of the invention may also contain a polynucleotide encoding a marker for selection of cells that contain such a vector. Examples of a suitable marker include genes that encode resistance to antibiotics, such as ampicillin, chloramphenicol, kanamycin, or nourseothricin.

As use herein, the terms "subject" and "patient" refer to an organism that receives treatment for a particular disease or condition as described herein (such as cancer or an infectious disease). Examples of subjects and patients include mammals, such as humans, primates, pigs, goats, rabbits, hamsters, cats, dogs, guinea pigs, members of the bovidae family (such as cattle, bison, buffalo, elk, and yaks, among others), cows, sheep, horses, and bison, among others, receiving treatment for diseases or conditions, e.g., cell proliferation disorders, such as cancer or infectious diseases.

As use herein, the terms "treat" or "treatment" refer to surgical or pharmaceutical treatment, in which the object is to prevent or slow down (lessen) an undesired physiological change or disorder, such as the progression of a cell proliferation disorder, such as cancer, or an infectious disease. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Those in need of treatment include those already with the condition or disorder, as well as those prone to have the condition or disorder or those in which the condition or disorder is to be prevented. When the terms slow down, alleviation, diminishment, palliation and remission are mentioned, it also includes the meanings of elimination, disappearance and non-occurrence.

Embodiments of the invention will be described in detail below in combination with Examples, but those skilled in the art will understand that the following Examples are for illustrating the invention only and should not be regarded as limiting of the scope of the invention. If no specific conditions are provided in the Examples, the conventional conditions or the conditions recommended by the manufacturer shall be followed. If the reagent or instrument used does not indicate the manufacturer, it is a conventional product that can be purchased commercially.

Example 1 Preparation of TNFR2 Monoclonal Antibody

Human TNFR2 recombinant protein (purchased from SinoBiological, Catalog. 10417-H08H and Novoprotein, Catalog. C830) was mixed with complete Freund's adjuvant (CFA, purchased from SIGMA, Catalog. F5881) for the first immunization of 6-8 week-old female SJL mice (purchased from Beijing Viton Lihua Experimental Animal Technology Co., Ltd.) or Balb/c mice (purchased from Shanghai Slake Experimental Animal Co., Ltd.), and incomplete Freund's adjuvant (IFA, purchased from SIGMA, Catalog. F5506) and CpGODN1826 (synthesized by Shanghai Biotechnology) were used as adjuvants for the last three immunization. In particular, the first and second immunization were performed on the rear foot pad and the back, and the third and fourth immunization were performed on the tail subcutaneous and the back, to obtain antiserum and antigen-specific immune cells with high titer, high affinity and high specificity. On the 7th day after the last immunization (the fourth immunization), the mice were euthanized and the spleens were taken out aseptically. The spleen lymphocytes of the mice were isolated aseptically, aliquoted and frozen in liquid nitrogen, and thawed when needing to be used. TNFR2-specific single B cells in spleen or lymph nodes of the immunized mice were sorted into 96-well plates by BD ARIA III flow sorter, and mRNA of the single cells was reverse transcribed into cDNA. Then nested PCR was carried out using cDNA as template to amplify the heavy chain and light chain of antibodies, respectively. The heavy chain variable region and light chain variable region were amplified and cloned into a heavy chain expression vector and light chain expression vector respectively by the homologous recombination method. Constant regions of the heavy chain expression vector and light chain expression vector are derived from human IgG1. The complete heavy chain expression sequence is signal peptide-VH-CH1-hinge region-CH2-CH3, and the complete light chain expression sequence is signal peptide-Vκ-Cκ. The cloning and expression of the above-mentioned single B cell antibodies were all carried out in a 96-well plate to achieve rapid identification and discovery in a high throughput manner. After a series of physico-chemical and functional screening of 523 pairs of cloned antibody heavy and light chains, 11 positive candidate antibody molecules were obtained. CDRs of the candidate antibody molecules were analyzed by IMGT and KABAT, respectively, and the corresponding sequence information is shown in Tables 1 to 3 below, wherein Table 1 shows VH and VL sequences of the candidate antibody molecules, Table 2 shows IMGT analysis results of the CDRs of candidate antibody molecules, and Table 3 shows KABAT analysis results of the CDRs of candidate antibody molecules.

TABLE 1

VH and VL sequences of the candidate antibody molecules

| Antibody ID | SEQ ID NO. | Sequence |
|---|---|---|
| TNFR2 antibody: VH | | |
| 1 | SEQ ID No. 1 | EVQLQESGGGLVQPGGSLNLSCAASGFAFSTYDLSWVRQTPEKRLEWVAYINNG GISTYYSDTVKGRFTISRDNAKNTLYLQMSSLKSEDTAMYYCVRGPFYGSANYFD YWGQGTTVTVSS |
| 88 | SEQ ID No. 3 | EVQLQESGGGLVQPGGSLNLSCAASGFAFSTYDLSWVRQTPEKRLEWVAYINNG GISTYYSDTVKGRFTISRDNAKNTLYLQMSSLKSEDTAMYYCVRGPFYGSANYFD YWGQGTTVTVSS |
| 125 | SEQ ID No. 5 | EVQLQESGGGLVQPGGSLNLSCAASGFAFSiYDLSWVRQTPEKRLEWVAYINNG GISTYYSDTVKGRFTISRDNAKNTLYLQMSSLKSEDTAMYYCVRGPFYGSANYFD YWGQGTTVTVSS |
| 133 | SEQ ID No. 7 | EVQLQESGAELVRSGASVKLSCTASGFNIKDYYIQWVKQRPEQGLEWIGWIDPES GNTKYAPKFQDKATMTADTSSNTAYLQLSGLTSEDSAVYYCNAYYDYDGSMDY WGQGTTVTVSS |
| 219 | SEQ ID No. 9 | EVQLQESGAELVRPGASVKLSCKASGYSFTNYWMNWVKQRPGQGLEWIGMIHP SDTETRLNQNFKDKATLTVDKSSSTSYMQLSSPTSEDSAVYYCARGEGLGAARSV SMDYQGQGTTVTVSS |
| 224 | SEQ ID No. 11 | EVQLQESGPEIVHPGASVKLSCTASGFNNKDIYMHWVKQRPEQGLEWIGRIDPAT GNTKHDPKFQDKATLSSDTSSNTAYLQFSSLTSEDAVYYCAHSPYGDFGAMDY WGQGTTVTVSS |

TABLE 1-continued

VH and VL sequences of the candidate antibody molecules

| 226 | SEQ ID No. 13 | EVQLQESGAELVRPGASVKLSCKASGYSFTNYWMNWVKQRPGQGLEWIGMIHP SDSETRLNQKFKDKATLTVDKSSSTAYMQLSSPTSEDSAVYYCARGEGLGAARS VSMDYWGQGTTVTVSS |
| 309 | SEQ ID No. 15 | EVQLQESGAELVKPGASVKLSCKASGYTFTSYWIHWVKLRPGQGFEWIGEINPNN GGTDYNEKFKRKATLTVDKSSSTAYMELSSLTSEDSAIYYCTIDSMITTTWFAYW GQGTTVTVSS |
| 352 | SEQ ID No. 17 | EVQLQESGPGLVAPSQSLSITCTVSGFSLTSYGVHWVRQPPGKGLEWLVVIWSDG GTTYNSALKSRLSISKDNSKSQVFLKMNSLQTDDTAMYYCARHDDDGYYAMDY WGQGTTVTVSS |
| 365 | SEQ ID No. 19 | EVQLQESGPGLVQPSQSLSITCTVSGFSLTSYGVHWVRQSPGKGLEWLGLIWSDG SPDYSAAFISRLSINKDNSKQVFFKMNSLQADDTAIYYCARNDDGGDYVMDYW GQGTTVTVSS |
| 395 | SEQ ID No. 21 | EVQLQESGPGLVQPSQSLSITCTVSGFSLTSYGVHWVRQSPGKGLEWLGVIWSDG GTDYSAAFISRLSISKDNSKQVFFKMNSLQADDTAIYYCARNDDGGDYAMDYW GQGTTVTVSS |

TNFR2 antibody: VL

| 1 | SEQ ID No. 2 | EIVMTQSPASLSLSVGETVTITCRTSESIYSNLPWYQQKQGKSPQLLVYDATKLAE GVPSRFSGSESGTQYSLKINSLQSEDFGTYYCQHFWVTPWTFGGGTKLEIK |
| 88 | SEQ ID No. 4 | DILMTQSPASLSLFVGETVTITCRASENIYSNLAWYQQKQGKSPQLLVYDATKLA EGVPSRFSGSESGTQYSLKINSLQSEDFGTYYCQHFWVTPWTFGGGTKLEIK |
| 125 | SEQ ID No. 6 | DIQMTQSPASLSLSVGETVTITCRASENIYSNLAWYQQKQGKSPQLLVYDATKLA EGVPSRFSGSESGTQYSLKINSLQSEDFGTYYCQHFWVTPWTFGGGTKLEIK |
| 133 | SEQ ID No. 8 | DIVMTQSPLSLPVSLGDQASISCRSSQSLVHSNGNTYLHWYLQKPGQSPKLLIYKV SNRFSGVPDRFSGSGSGTDFTLKISRVETDDLGVYFCSQSTHVPTWTFGGGTKLEI K |
| 219 | SEQ ID No. 10 | DILMTQSPSSLSASLGDRVTISCRASQDISNYLNWYQQKPDGTVKVLIYYTAILHS GVPSRFSGSGSGTDYSLTISNLEQEDIATYFCQQGNTLPWTFGGGTKLEIK |
| 224 | SEQ ID No. 12 | DIQMTQSPAIMSASLGERVTMTCTASSSVSSNYLHWYQQKPGSSPKLWIYSTSNL PSGVPARFSGSGSTSYSLTISSMEAEDAATYYCHQYHRSPWTFGGGTKLEIK |
| 226 | SEQ ID No. 14 | DIQMTQSPSSLSASLGDRVTISCRASQDISNYLNWYQQKPDGTVKVLIYYTALLHS GVPSRFSGSGSTDYSLTISNLEQEDIATYFCQQGNTLPWTFGGGTKLEIK |
| 309 | SEQ ID No. 16 | EIVMTQSQKLMSTVVGDRVSVTCKASQNVGTNVAWFQQKPGQSPKALINSASYR YSGVPDRFTGSGSGTDFTLTISSVQSEDLAEYFCQQYNSYPFTFGSGTKLEIK |
| 352 | SEQ ID No. 18 | DIVLTQSPSLMSASPGEKVTNITCSASSSVGYMYWYQQKPRSSPKPWIYLTSNLAS GVPARFSGSGSGTSYSLTISSMEVEDAATYYCQQWSSDPFTFGSGTKLEIK |
| 365 | SEQ ID No. 20 | EIVLTQSPALMSASPGEKVTNITCSASSSVSYMYWYQQKPRSSPKPWIYLTSNLAS GVPARFSGSGSGTSYSLTISSMEAEDAATYYCQQWTSNPLTFGAGTKLEIK |
| 395 | SEQ ID No. 22 | EIVLTQSPALMSASPGEKVTNITCSASSSVSYMYWYQQKPRSSPKPWIYLTSNLAS GVPARFSGSGSGTSYSLTISSMEAEDAATYYCQQWSSNPLTFGAGTKLEIK |

TABLE 2

IMGT analysis results of the candidate antibodies

TNFR2 antibody: IMGT analysis of heavy chain CDR region

| Antibody ID | SEQ ID NO. | CDR1-VH | SEQ ID NO. | CDR2-VH | SEQ ID NO. | CDR3-VH |
|---|---|---|---|---|---|---|
| 1 | 26 | GFAFSTYD | 27 | INNGGIST | 28 | VRGPFYGSANYFDY |
| 88 | 38 | GFAFSTYD | 39 | INNGGIST | 40 | VRGPFYGSANYFDY |
| 125 | 50 | GFAFSIYD | 51 | INNGGIST | 52 | VRGPFYGSANYFDY |
| 133 | 62 | GFNIKDYY | 63 | TDPESGNT | 64 | NAYYDYDGSMDY |

TABLE 2-continued

IMGT analysis results of the candidate antibodies

| Antibody ID | SEQ ID NO. | CDR1 | SEQ ID NO. | CDR2 | SEQ ID NO. | CDR3 |
|---|---|---|---|---|---|---|
| 219 | 74 | GYSFTNYW | 75 | IHPSDTET | 76 | ARGEGLGAARSVSNEDY |
| 224 | 86 | GFNNKDIY | 87 | IDPATGNT | 88 | AHSPYGDFGAMDY |
| 226 | 98 | GYSFTNYW | 99 | IHPSDSET | 100 | ARGEGLGAARSVSMDY |
| 309 | 110 | GYTFTNYW | 111 | INPNNGGT | 112 | TIDSMITTTWFAY |
| 352 | 122 | GFSLTSYG | 123 | IWSDGGT | 124 | ARHDDDGYYAMDY |
| 365 | 134 | GFSLTSYG | 135 | IWSDGSP | 136 | ARNDDGGDYVMDY |
| 395 | 146 | GFSLTSYS | 147 | IWSDGGT | 148 | ARHDDGGDYAMDY |

TNFR2 antibody: IMGT analysis of light chain CDR region

| Antibody ID | SEQ ID NO. | CDR1-VL | SEQ ID NO. | CDR2-VL | SEQ ID NO. | CDR3-VL |
|---|---|---|---|---|---|---|
| 1 | 32 | ESIYSN | 33 | DAT | 34 | QHFWVTPVIT |
| 88 | 44 | ENIYSN | 45 | DAT | 46 | QHFWVTPWT |
| 125 | 56 | ENIYSN | 57 | DAT | 58 | QHFWVTPWT |
| 133 | 68 | QSLVHSNGNTY | 69 | KVS | 70 | SQSTHVPTWT |
| 219 | 80 | QDISNY | 81 | YTA | 82 | QQGNTLPWT |
| 224 | 92 | SSVSSNY | 93 | STS | 94 | HQYHRSPWT |
| 226 | 104 | QDISNY | 105 | YTA | 106 | QQGNTLPWT |
| 309 | 116 | QNVGTN | 117 | SAS | 118 | QQYNSYPFT |
| 352 | 128 | SSVGY | 129 | LTS | 130 | QQWSSDPFT |
| 365 | 140 | SSVSY | 141 | LTS | 142 | QQWTSNPLT |
| 395 | 152 | SSVSY | 153 | LTS | 154 | QQWSSNPLT |

TABLE 3

KABAT analysis results of candidate antibodies

TNFR2 antibody: KABAT analysis of heavy chain CDR region

| Antibody ID | SEQ ID NO. | CDR1-VH | SEQ ID NO. | CDR2-VH | SEQ ID NO. | CDR3-VH |
|---|---|---|---|---|---|---|
| 1 | 23 | TYDLS | 24 | YINNGGISTYYSDIVKG | 25 | GPFYGSANYFDY |
| 88 | 35 | TYDLS | 36 | YINNGGISTYYSDTVKG | 37 | GPFYGSANYFDY |
| 125 | 47 | IYDLS | 48 | YINNGGISTYYSDTVKG | 49 | GPFYGSANYFDY |
| 133 | 59 | DYYIQ | 60 | WIDPESGNTKYAPKFQD | 61 | YYDYDGSMDY |
| 219 | 71 | NYWMN | 72 | MIHPSDSETRLNQKFKD | 73 | GEGLGAARSVSMDY |
| 224 | 83 | DIYMH | 84 | RIDPATGNTKHDPKFQD | 85 | SPYGDFGAMDY |
| 226 | 95 | NYWMN | 96 | MIHPSDSETRLNQKFKD | 97 | GEGLGAARSVSDY |
| 309 | 107 | SYWIH | 108 | EINPNNGGIDYNEKFKR | 109 | DSMITTTWFAY |
| 352 | 119 | SYGVH | 120 | VIWSDGGTTYNSALKS | 121 | HDDDGYYAMDY |
| 365 | 131 | SYGVH | 132 | LIWSDGSPDYSAAFIS | 133 | NDDGGDYVMDY |
| 395 | 143 | SYSVH | 144 | VIWSDGGIDYSAAFIS | 145 | NDDGGDYAMDY |

TABLE 3-continued

KABAT analysis results of candidate antibodies

TNFR2 antibody: KABAT analysis of light chain CDR region

| Antibody ID | SEQ ID NO. | CDR1-VL | SEQ ID NO. | CDR2-VL | SEQ ID NO. | CDR3-VL |
|---|---|---|---|---|---|---|
| 1 | 29 | RTSESIYSNLP | 30 | DATKLAE | 31 | QHFWVTPWT |
| 88 | 41 | RASENIYSNLA | 42 | DATKLAE | 43 | QHFWVTPWT |
| 125 | 53 | RASENTYSNLA | 54 | DATKLAE | 55 | QHFWVTPWT |
| 133 | 65 | RSSQSLVHSNGNTYLH | 66 | KVSNRFS | 67 | SQSTHVPTWT |
| 219 | 77 | RASQDISNYLN | 78 | YTAILHS | 79 | QQGNTLPWT |
| 224 | 89 | TASSSVSSNYLH | 90 | STSNLPS | 91 | HQYHRSPWT |
| 226 | 101 | RASQDISNYLN | 102 | YTALLHS | 103 | QQGNTLPWT |
| 309 | 113 | KASQNVGTNVA | 114 | SASYRYS | 115 | QQYNSYPFT |
| 352 | 125 | SASSSVGYMY | 126 | LTSNLAS | 127 | QQWSSDPFT |
| 365 | 137 | SASSSVSYMY | 138 | LTSNLAS | 139 | QQWTSNPLT |
| 395 | 149 | SASSSVSYMY | 150 | LTSNLAS | 151 | QQWSSNPLT |

Example 2 FACS Assessment of TNFR2 Expression in Tumor Cell Lines

Well-growing cells were collected, and $2\times10^6$ cells were obtained after counting from each tumor cell and used in an isotype control group and a TNFR2 staining group ($1\times10^6$ cells/test) respectively. The cells were washed twice with PBS and centrifuged for 300 g×5 min to discard the supernatant, 1×Live/Dead working solution (Zombie violet L/D, Biolegend, Catalog No. 423114) 100 μl/test was added, and the cells were stained at room temperature for 20 minutes. After 20 minutes, the cells were washed twice with FACS buffer (DPBS+2% FBS) and centrifuged for 300 g×5 min to discard the supernatant, 1×staining antibody working solution at 100 μl/test was added as follows, and the cells were incubated at 4° C. for 30 minutes avoiding from light.

For human tumor cells: 1) the isotype control group: 1 μl PE rat IgG2b, κ isotype control (BD Pharmingen, Catalog No. 553989)/100 μl FACS buffer/test was added; 2) the TNFR2 staining group: 8 μl PE Rat anti-human CD120b (BD Pharmingen, Catalog No. 552418)/100 μl FACS buffer/test was added into human tumor cells. After incubation, the cells were washed twice with the FACS buffer, centrifuged for 300 g×5 min to discard the supernatant and resuspended with 300 μl FACS buffer, and the cell suspension was analyzed by using a flow cytometer (Invitrogen, Attune NxT). Data was then exported and analyzed by Flowjo software (TreeStar), as shown in FIG. 1, wherein different tumor cells expressed different levels of TNFR2, and the results are summarized in Table 4.

TABLE 4

TNFR2 expression results of 13 human tumor cell lines

| No. | Tumor cell lines | Tumor type | iso-PE (%) | TNFR2-PE (%) | Percent fold to iso | MFI fold to iso |
|---|---|---|---|---|---|---|
| 1 | THP-1 | Human Acute monocytic leukemia | 2.52 | 17.7 | 7 | 1.6 |
| 2 | K562 | Human Chronic myelogenic leukemia | 8.36 | 59.8 | 7.2 | 2.7 |
| 3 | HH | Human T lymphocyte | 0.14 | 0.05 | 0.4 | 0.2 |
| 4 | HUT102 | Human Cutaneous T lymphocyte | 1 | 4.35 | 4.4 | 1.2 |
| 5 | HUT78 | Human Cutaneous T lymphocyte | 1.77 | 80.6 | 45.5 | 79.4 |
| 6 | CAPAN-2 | Human Pancreas adenocarcinoma | 2.74 | 51.3 | 18.7 | 2.6 |
| 7 | OVCAR3 | Human Ovary adenocarcinoma | 0.71 | 1.55 | 2.2 | 1.1 |
| 8 | Myla | Human cutaneous T lymphocyte | 0.1 | 0.1 | 1.0 | 2.1 |
| 9 | SW620 | Human Colon cancer | 6.02 | 23.9 | 4 | 1.5 |
| 10 | SW480 | Human Colon cancer | 3.5 | 83.1 | 23.7 | 11.6 |
| 11 | 8226 | Human Multiple myeloma | 7.09 | 85.8 | 12.1 | 1.1 |
| 12 | MCF-7 | Human Breast cancer | 1.1 | 0.14 | 0.1 | 0.3 |
| 13 | MDA-MB-231 | Human Breast cancer | 0.84 | 3.49 | 4.2 | 1.4 |

Example 3 FACS Assessment of TNFR2 Expression Levels on Different Human T Cells

Commercial frozen human PBMC (Hemacare) or anti-CD3/CD28 Dynabeads (Gibco, Catalog No. 11129D) activated and expanded Treg cells were resuscitated, and cultured overnight. The next day, human PBMC was centrifuged at 300×g for 10 min to discard supernatant. $2\times10^6$ PBMC cells were obtained after counting and were used in an isotype control group and a TNFR2 staining group ($1\times10^6$ cells/test), respectively. Cells were washed twice with PBS and centrifuged for 5 min at 300 g to discard the supernatant, 1×Live/Dead working solution (Zombie violet L/D, Biolegend, Catalog No. 423114) 100 μl/test was added, and the cells were stained at room temperature for 20 minutes. After 20 minutes, the cells were washed twice with the FACS buffer (DPBS+2% FBS) and centrifuged for 5 min at 300 g to discard the supernatant, 1× staining antibody working solution 100 μl/test was added as follows, and the cells were incubated at 4° C. for 30 minutes avoiding from light.

For PBMC cells: 1) Fluorescence Minus One control (FMO control) group: 1 μl of the antibody shown in the following table/100 μl FACS buffer/test was added;

| Product No. | Fluorescent dyes/markers | Clones |
|---|---|---|
| BD Pharmingen-557943 | Alexa fluor 700 CD3 | UCHT1 |
| BD Bioscience-560650 | PerCP/Cy5.5 CD4 | RPA-T4 |
| BD Bioscience-335789 | PE/Cy7 CD25 | 2A3 |
| BD Bioscience-557714 | Alexa fluor 647 mouse IgG1, κ | MOPC-21 |
| Bioleegend-423114 | Zombie violet Live/Dead | |
| Biolegend-300926 | APC/Cy7 CD8 | HIT8a |
| BD/R&D | PE rat IgG2b, κ | A95-1; |

2) TNFR2 staining group: 1 μl of the antibody shown in the following table/100 μl FACS buffer/test was added;

| Product No. | Fluorescent dyes/markers | Clones |
|---|---|---|
| BD Pharmingen-557943 | Alexa fluor 700 CD3 | UCHT1 |
| BD Bioscience-560650 | PerCP/Cy5.5 CD4 | RPA-T4 |
| BD Bioscience-335789 | PE/Cy7 CD25 | 2A3 |
| BD Bioscience-560045 | Alexa fluor 647 FoxP3 | 259D/C7 |
| Bioleegend-423114 | Zombie violet Live/Dead | |
| Biolegend-300926 | APC/Cy7 CD8 | HIT8a |
| BD/R&D | PE TNFR2 | hTNFR-M1. |

For Treg cells: 1) FMO control group: 1 μl of the antibody shown in the following table/100 μl FACS buffer/test was added;

| Product No. | Fluorescent dyes/markers | Clones |
|---|---|---|
| BD Pharmingen-557943 | Alexa fluor 700 CD3 | UCHT1 |
| BD Bioscience-560650 | PerCP/Cy5.5 CD4 | RPA-T4 |
| BD Bioscience-335789 | PE/Cy7 CD25 | 2A3 |
| BD Bioscience-557714 | Alexa fluor 647 mouse IgG1, κ | MOPC-21 |
| Bioleegend-423114 | Zombie violet Live/Dead | |
| BD/R&D | PE rat IgG2b, κ | A95-1; |

2) TNFR2 staining group: 1 μl of the antibody shown in the following table/100 μl FACS buffer/test was added;

| Product No. | Fluorescent dyes/markers | Clones |
|---|---|---|
| BD Pharmingen-557943 | Alexa fluor 700 CD3 | UCHT1 |
| BD Bioscience-560650 | PerCP/Cy5.5 CD4 | RPA-T4 |
| BD Bioscience-335789 | PE/Cy7 CD25 | 2A3 |
| BD Bioscience-560045 | Alexa fluor 647 FoxP3 | 259D/C7 |
| Bioleegend-423114 | Zombie violet Live/Dead | |
| BD/R&D | PE TNFR2 | hTNFR-M1. |

Figure 2A:
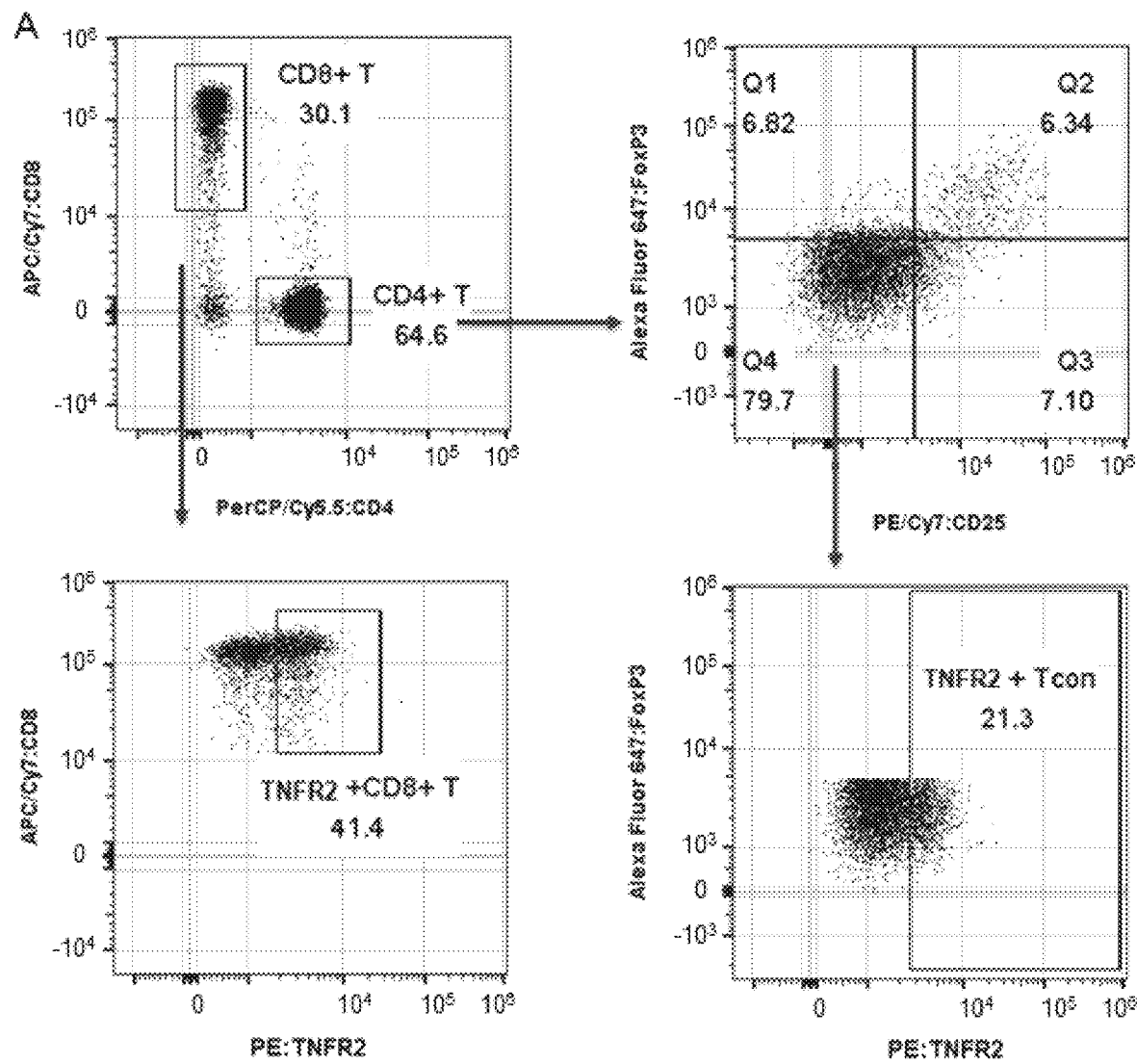
FIG. 2A shows a scatter plot of flow cytometry staining and gating strategy of Treg cells, $CD8^+$ T cells and Tcon cells, and the expression level of TNFR2 on those cells.
Figure 2B:
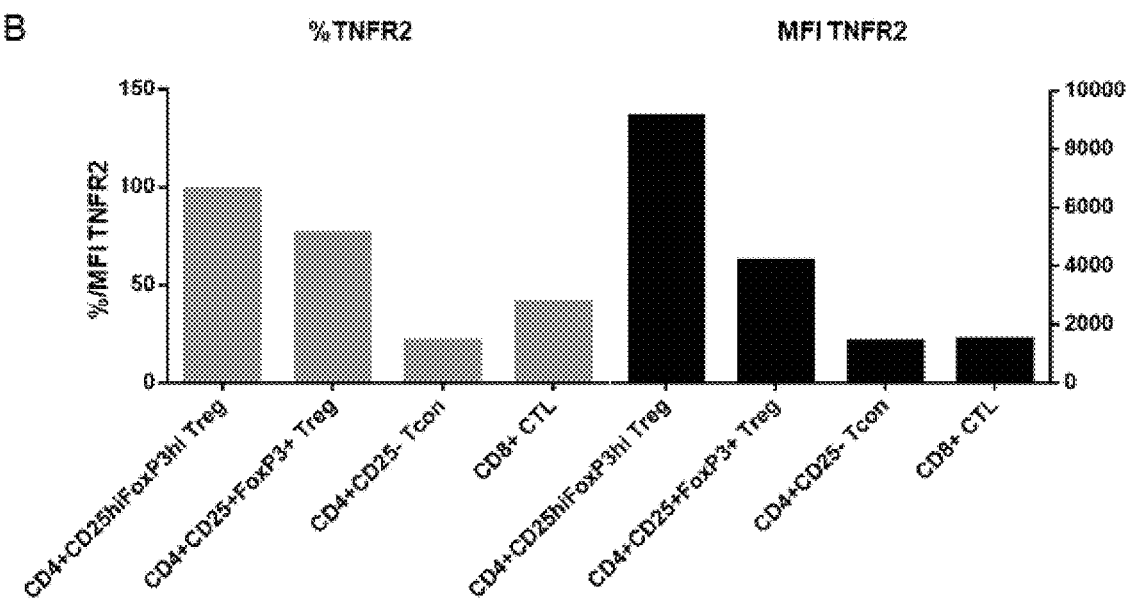
FIG. 2B shows the proportion and mean fluorescence intensity (MFI) value of TNFR2 expression in activated Tregs ($CD4^+CD25^{hi}FoxP3^{hi}$Treg), inactivated Tregs ($CD4^+CD25^{hi}FoxP3^+$Treg), Tcon ($CD4^+CD25^-$T cells) and $CD8^+$ T cells.

After incubation, the cells were washed twice with the FACS buffer, centrifuged at 300 g for 5 min to discard the supernatant and resuspended with 300 μl FACS buffer, and the cell suspension was analyzed using a flow cytometer (Invitrogen, Attune NxT). Data was then exported and analyzed by Flowjo software as shown in FIG. 2, wherein the expression level of TNFR2 on $CD4^+CD25^-$Tcon cells and $CD8^+$ T cells was much lower than that on both inactivated and activated Treg cells with the highest expression level in the latter.

Example 4 BIAcore Assay of Specific Binding of the TNFR2 Antibody to Human and Cynomolgus TNFR2 Proteins Biacore was used to detect the specific binding of 11 TNFR2 antibody clones from Example 1 to human and cynomolgus TNFR2 proteins. In this experiment, Protein A chip was used, and the time required for the chip to capture the diluted antibody was determined by manual run, so that the Rmax of the saturated binding antigen was 50 RU. Human TNFR2 (Sino 10417-H08H) and cynomolgus TNFR2 (Sino 90102-C08H) were diluted to 32, 16, 8, 4, 2 nM. The affinity of antibody and antigen was measured by multi-cycle kinetics. In each cycle, anti-TNFR2 antibodies were injected prior to the injection of gradient concentrations of TNFR2 protein allowing the occurrence of antibody-antigen association and dissociation. After each cycle, the Protein A chip was regenerated with Glycine pH1.5 (to remove the protein on the chip). BIAcore T200 analysis software was used to calculate the affinity KD of antibody binding to antigen.

TABLE 5

Biacore results of specific binding of the TNFR2 antibody to human or cynomolgus TNFR2 proteins

| Antibody | Ag | KD (M) | Ka (1/Ms) | Kd (1/s) | Ag | KD (M) | Ka (1/Ms) | Kd (1/s) |
|---|---|---|---|---|---|---|---|---|
| # 001 | Human | 1.61E-10 | 5.56E+05 | 8.95E-05 | Cynomolgus | 2.79E-10 | 6.62E+05 | 1.85E-04 |
| # 088 | TNFR2 | 1.07E-10 | 5.10E+05 | 5.46E-05 | TNFR2 | 2.86E-10 | 6.01E+05 | 1.72E-04 |
| # 125 | | 6.81E-11 | 8.17E+05 | 5.57E-05 | | 1.51E-10 | 1.02E+06 | 1.55E-04 |
| # 133 | | 2.94E-09 | 1.32E+06 | 3.88E-03 | | 3.61E-09 | 2.82E+06 | 1.02E-02 |
| # 219 | | 2.34E-10 | 3.58E+05 | 8.40E-05 | | 8.63E-10 | 5.58E+05 | 4.81E-04 |
| # 224 | | 1.01E-10 | 2.33E+05 | 2.36E-05 | | 2.73E-10 | 4.25E+05 | 1.16E-04 |
| # 226 | | 1.94E-10 | 3.69E+05 | 7.14E-05 | | 5.77E-10 | 5.51E+05 | 3.18E-04 |
| # 309 | | 1.44E-09 | 5.19E+05 | 7.48E-04 | | 2.48E-09 | 8.54E+05 | 2.12E-03 |
| # 352 | | 1.41E-09 | 1.59E+06 | 2.25E-03 | | 9.43E-10 | 2.57E+06 | 2.43E-03 |
| # 365 | | 9.52E-10 | 2.20E+06 | 2.09E-03 | | 7.52E-10 | 4.10E+06 | 3.08E-03 |
| # 395 | | 1.40E-10 | 1.70E+06 | 2.37E-04 | | 9.77E-11 | 2.83E+06 | 2.76E-04 |

As shown in Table 5, 11 anti-TNFR2 antibodies from Example 1 specifically bind to human and cynomolgus TNFR2 proteins with high affinity.

Example 5 ELISA Assay of Specific Binding of the TNFR2 Antibody to Human and Cynomolgus TNFR2 Proteins An microplate was pre-coated with 100 μl/well of 0.5 μg/ml human TNFR2 or cynomolgus TNFR2 (the same antigen protein as in Example 4). Purified anti-TNFR2 antibodies from Example 1 were diluted to 28 ng/ml (corresponding to the EC80 of the binding curve of antibody #1), added at 100 μl/well, and incubated with shaking at room temperature for 1.5 h. A mouse anti-human IgG Fc-HRP working solution (1:10000 dilution) was added to the plate at 100 μl/well after plate washing, and incubated with shaking at room temperature for 1.0 h. The plate was washed again, a HRP substrate TMB was added for color development prior to the termination of the reaction by adding termination solution. An microplate reader was used to read the absorption value. Data in Table 6 show that the 11 antibodies can specifically bind to human and cynomolgus TNFR2 proteins, but not to mouse TNFR2 or a control human CREG-His protein.

TABLE 6

ELISA results of specific binding of the TNFR2 antibody to human and cynomolgus TNFR2 proteins

| Antibodies | ELISA OD (28 ng/ml) | |
| --- | --- | --- |
| | hTNFR2 (His tag) | CynoTNFR2 (His tag) |
| 002 # (control) | 3.223 | 3.276 |
| # 001 | 2.812 | 2.642 |
| # 088 | 1.312 (12 ng/ml) | 1.435 (12 ng/ml) |
| # 125 | 3.318 | 3.249 |
| # 133 | 3.119 | 3.181 |
| # 219 | 3.371 | 3.409 |
| # 224 | 2.235 | 2.657 |
| # 226 | 3.343 | 3.283 |
| # 309 | 1.899 (12 ng/ml) | 2.273 (12 ng/ml) |
| # 352 | 3.121 | 3.124 |
| # 365 | 3.194 | 3.155 |
| # 395 | 3.175 | 3.154 |

Note:
1. 002# is a tool antibody (SBT-002 from WO2017/083525 A1)

2. Only a single concentration of each antibody was measured, which is expressed by OD value, wherein the concentration of antibody #088 and #309 was 12 ng/mL, and the concentration of other antibodies was 28 ng/mL.

Figure 3A:
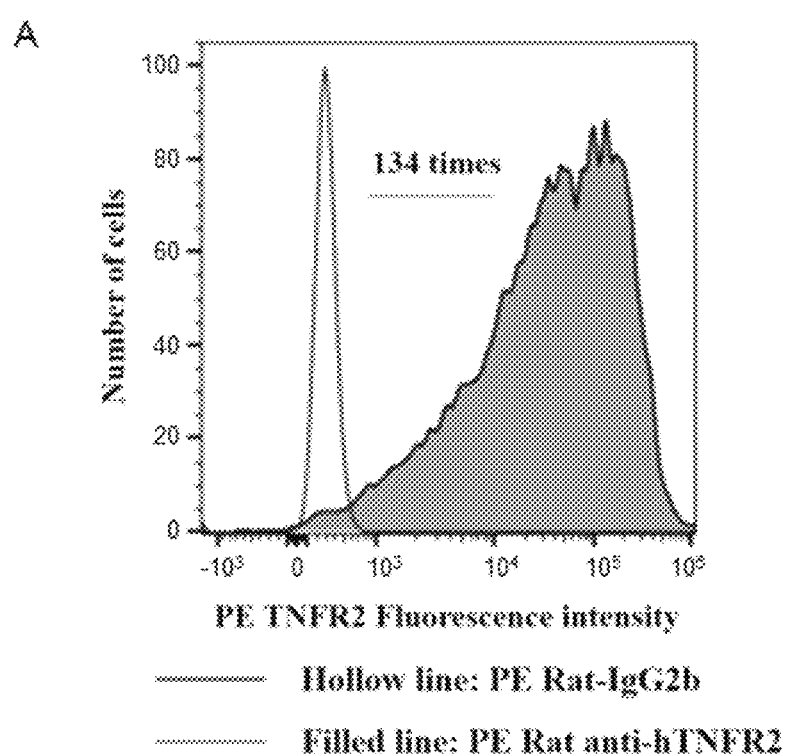
FIG. 3A shows a confirmation of the expression of human TNFR2 on the surface of CHO-TNFR2 cells.
Figure 3B:
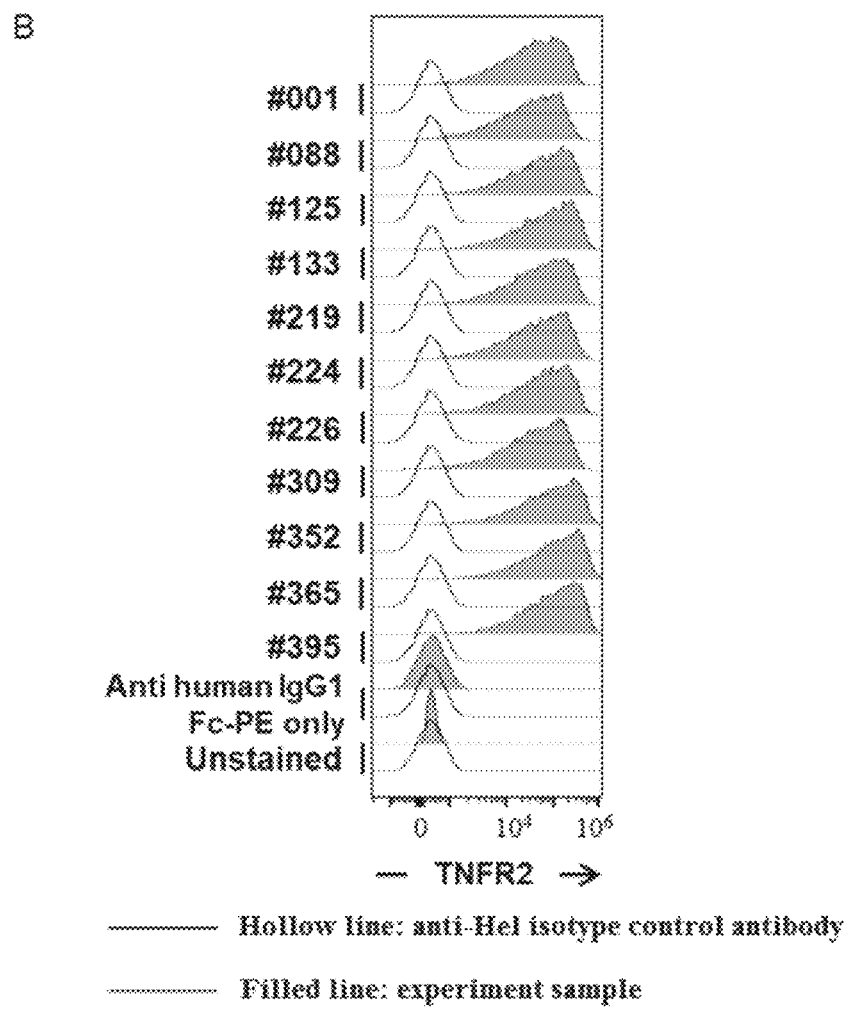
FIG. 3B shows binding of 11 test antibodies of the invention to TNFR2 overexpressed on CHO cells, among them, anti-human IgG1 Fc-PE only and anti-Hel isotype control antibody (egg white lysozyme is an intracellular antigen and does not exist in human body, which is a good unrelated control antibody, purchased from Biotron) are all negative controls in this experiment, while Unstained is a blank cell control without any antibody staining.

Example 6 FACS Assessment of Binding of the Antibody to Human TNFR2 on the Surface of CHO-TNFR2 Cells CHO cells that stably overexpressed human TNFR2 were constructed by cells transfecting with a TNFR2 plasmid (purchased from Sino Biological, Catalog No. HG10417-UT). All binding experiments were carried out with a cell density not exceeding 80%. Culture medium was discarded and cells were washed with PBS and digested with 1 ml trypsin for 2 minutes. HamFBS culture medium containing 10% FBS was used to terminate the digestion and acquire cell suspension. Appropriate amount of the cell suspension was taken after counting and centrifuged at 350×g. Supernatant was discarded, and the cells were resuspended to a density of $1 \times 10^7$ cells/ml by adding blocking buffer (10% FBS+PBS), and incubated at 4° C. for 30 minutes. After incubation, the supernatant was discarded after centrifugation at 350×g, and the cells were resuspended to a density of $2 \times 10^6$ cells/ml with a staining buffer (2% FBS+PBS) and then placed in a 96-well plate at 50 μl per well for later use. The antibodies were diluted to 80 ng/ml with PBS, and the diluted antibodies were then added to the well with 50 μl of the cell suspension. The plate was placed on a microplate shaker and shaked at 500 rpm for 1 minute to fully mix the cells and antibodies followed by incubating at 4° C. for 1 hour. After incubation, the cells were washed twice with the staining buffer at 100 μl per well, and centrifuged at 350×g for 5 minutes followed by discarding the supernatant. PE goat anti-Human IgG Fc antibody (ebioscience, Catalog No. 12-4998-82) was diluted 250-fold with the staining buffer, added to the wells with washed cell in a volume of 100 μl per well, evenly mixed, and stained at 4° C. for 30 minutes. After staining, the cells were also washed twice with the staining buffer and resuspended with 200 μl staining buffer. A flow cytometry was used to detect the signal intensity. The stronger the signal means the stronger of the binding ability of the antibodies to TNFR2 over expressing cells. As shown in FIG. 3A, PE Rat-IgG2b PE Rat-IgG2b (Biolegend, Catalog No. 400636) and PE Rat anti-hTNFR2 (BD Biosciences, Catalog No. 552418) were used to quantify TNFR2 expression and it was found that the expression intensity of TNFR2 on the surface of CHO-TNFR2 cell was about 134 fold more than that of the isotype stained cells. Based on this TNFR2 expression level, the ability of 11 TNFR2 antibodies from Example 1 to bind to TNFR2 on the cell surface was detected, and the results were all positive, as shown in FIG. 3B.

Figure 4A:
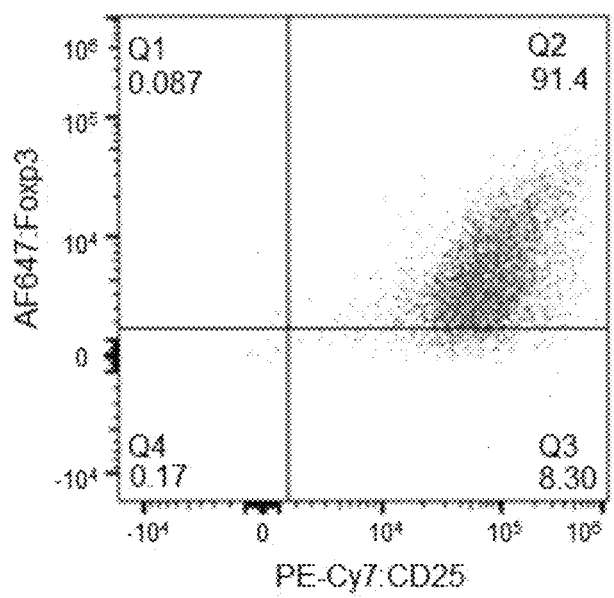
FIG. 4A shows the purity of $Foxp3^+$ Treg cells used in the experiment is 91.4%, and the expression ratio of TNFR2 is 99.5% (hollow peak diagram means the anti-Hel isotype control antibody, solid peak diagram means the anti-TNFR2 PE antibody)
Figure 4A:
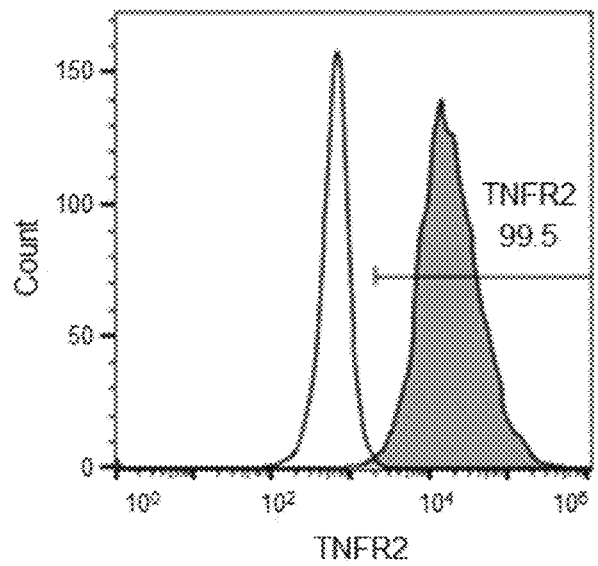
Figure 4B:
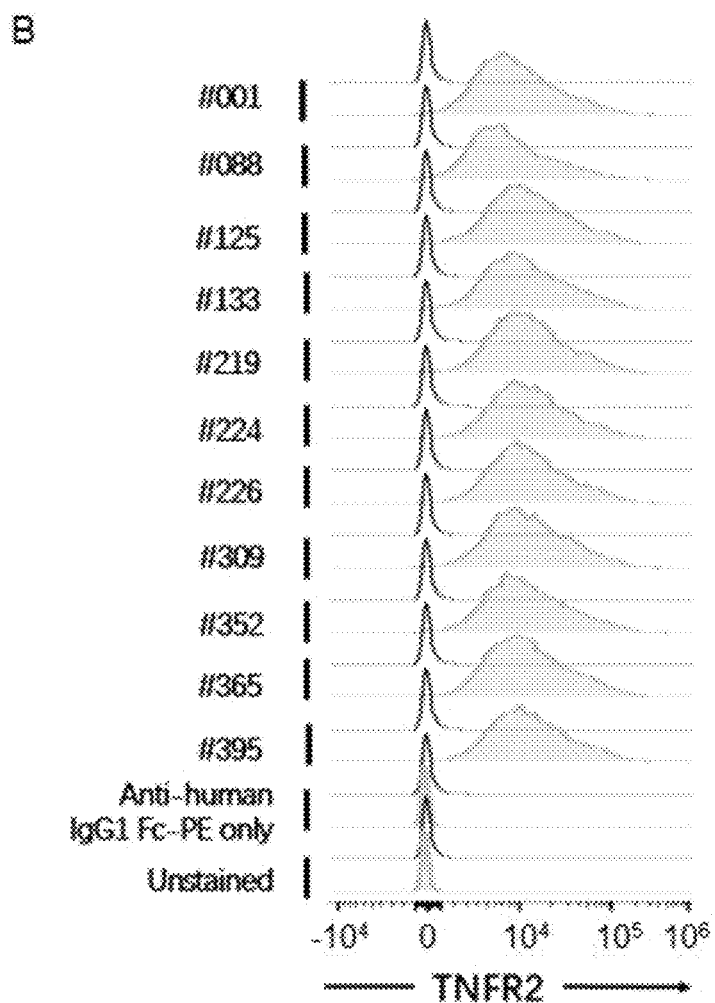
FIG. 4B shows the binding ability of each of the 11 antibodies of the invention on Treg cells (solid peaks), human IgG1 Fc-PE only and Unstained (blank cell control without any antibody added) are negative controls, and the antibody concentration is 200 ng/ml.

Example 7 FACS Assessment of Binding of the Antibody to Human TNFR2 on the Surface of Treg Cells Human Treg cells were isolated from human PBMC using a sorting kit (Stemcell, Catalog No. 18063), expanded in vitro by Dynabeads Human Treg Expander (Gibco, Catalog No. 11129D) for 17 days, aliquoted and cryopreserved for later use. The Treg cells isolated and expanded in vitro were recoveryed overnight, centrifuged at 300×g for 5 minutes the next day, resuspended with DPBS and counted. The amount of cells required for the experiment were added into centrifuge tubes, centrifuged at 300×g for 5 min and supernatant was discarded. Cell density was adjust to $1 \times 10^7$ cells/ml with blocking solution followed by incubation at 4° C. for 30 min. Supernatant was discarded after centrifugation at 300×g for 5 min followed by adjusting cell density to $2 \times 10^6$/ml with the staining buffer. Cells were then placed in the 96-well plate at 50 µl per well. Load 11 antibodies #001, #088, #125, #133, #219, #224, #226, #309, #352, #365, and #395 from Example 1 and the isotype control anti-Hel antibody (diluted to 200 ng/ml with PBS respectively, with the total amount of 100 µl) to each well at 50 µl per well. The plate with the cell suspension and the antibodies was placed on the microplate shaker and shaked at a speed of 500 rpm for 1 min to fully mix the cells and antibodies followed by incubation at 4° C. for 60 min. After incubation, 100 µl of the staining buffer was added to each well, the cells were centrifuged at 350×g for 5 min resuspended by adding 200 µl of the staining buffer to each well and centrifuged again at 350×g for 5 min. The staining buffer solution was added into PE goat anti-Human IgG Fc according with a ratio of 250:1 (staining buffer: dye) to prepare a staining solution, which was mixed evenly and added with a volume of 100 µl per well. The plate was placed on the microplate shaker and shaked at a speed of 500 rpm for 1 min to fully mix the cells with the staining solution followed by incubation at 4° C. for 30 min. Cells were washed twice resuspended with 200 µl PBS for FACS analysis. $CD25^+FoxP3^+$ cells shown in FIG. 4A are human Treg cells, 99.5% of gated Treg cells express TNFR2 indicating that human Treg cells highly express TNFR2. FIG. 4B shows that the isotype control anti-Hel antibody does not bind to Treg, while all 11 antibodies from Example 1 can effectively bind to Treg cells.

Example 8 ELISA Evaluation of TNFα/TNFR2 Interaction Blocking by Anti-TNFR2 Antibody A microplate was pre-coated with 100 µl/well of 1 µg/ml human TNFR2 (Novoprotein, Catalog No. C830). Each TNFR2 antibody from Example 1 was diluted to 40 nM and 4 nM. The diluted antibodies were mixed with 15 ng/ml human TNFa (Acro Biosystem, Catalog No. TNA-H82E3) in equal volumes, respectively, added to the microplate at 100 µl/well, and incubated with shaking at room temperature for 2.0 h. After washing the plate, a Streptavidin-HRP working solution (1:10000 dilution) was added at 100 µl/well, and incubated with shaking at room temperature for 40 min. The plate was washed again, the HRP substrate TMB was added for color development, the termination solution was added to terminate the reaction, and the microplate reader was used to read the absorption value. The lower the OD value, the stronger of the ability of the antibodies to inhibit the binding of TNFa to TNFR2. In the end, the OD values of all antibodies were normalized to the OD value of the tool antibody 002#, and the higher the percentage value means the stronger the inhibition ability. Data in Table 7 show that the 11 antibodies from Example 1 have the activity to inhibit the binding of TNFa to TNFR2 at both 20 nM and 2 nM (Table 7a-7b).

TABLE 7a

ELISA results-1, part of the test antibodies block binding of TNFα to TNFR2

| Antibodies | ELISA OD of antibodies to be tested | | ELISA OD of control antibody 002# | | % to 002# OD | |
|---|---|---|---|---|---|---|
| | (20 nM) | (2 nM) | (20 nM) | (2 nM) | (20 nM) | (2 nM) |
| # 001 | 0.198 | 0.805 | 0.249 | 0.678 | 125.9% | 84.2% |
| # 125 | 0.161 | 0.599 | 0.249 | 0.678 | 154.3% | 113.2% |
| # 219 | 0.280 | 0.756 | 0.249 | 0.678 | 89.0% | 89.7% |
| # 226 | 0.237 | 0.709 | 0.249 | 0.678 | 104.9% | 95.7% |

TABLE 7b

ELISA results-2, part of the test antibodies block binding of TNFα to TNFR2

| Antibodies | ELISA OD of antibodies to be tested | | ELISA OD of control antibody 002# | | % to 002# OD | |
|---|---|---|---|---|---|---|
| | (20 nM) | (2 nM) | (20 nM) | (2 nM) | (20 nM) | (2 nM) |
| # 088 | 0.350 | 2.341 | 0.329 | 1.622 | 94.1% | 69.3% |
| # 133 | 0.454 | 2.107 | 0.501 | 1.572 | 110.4% | 74.6% |
| # 224 | 0.123 | 1.442 | 0.340 | 1.452 | 276.8% | 100.7% |
| # 309 | 0.340 | 2.136 | 0.329 | 1.622 | 96.6% | 75.9% |
| # 352 | 0.474 | 1.782 | 0.501 | 1.572 | 105.7% | 88.2% |
| # 365 | 0.418 | 1.265 | 0.501 | 1.572 | 119.8% | 124.3% |
| # 395 | 0.282 | 1.142 | 0.501 | 1.572 | 177.6% | 137.7% |

Note:
1. 002# is the tool antibody;
2. % to 002# OD = ELISA OD for 002# (20 nM or 2 nM)/ELISA OD for antibody (20 nM or 2 nM) × 100.

Example 9 Anti-TNFR2 Antibodies Block Binding of TNFα to TNFR2 Overexpressed on CHO Cells CHO cells that stably overexpressed human TNFR2 were used for experiments. The cells were resuscitated and passaged until in good state, and the expression level of human TNFR2 on the cells was assessed by FACS. Compared to the isotype control, the assay could be carried out when the fold change of mean fluorescence intensity (MFI) was more than 100 times.

CHO-TNFR2 cells were digested, washed twice with DPBS and stained with Live/Dead (L/D) at room temperature for 20 min, and then seeded at $1\times10^5$ cells/50 µl/well. The anti-TNFR2 antibodies from Example 1 were diluted with the staining buffer to 40 nM as the initial concentration, and diluted with a 3-fold gradient, for a total of 7 concentration points. The diluted antibodies were added 50 µl/well into wells pre-seeded with cells, and gently blown and mixed to make the final concentrations of the antibodies to 20, 6.67, 2.22, 0.74, 0.247, 0.08, 0.027 and 0 nM, respectively followed by incubation at 4° C. for 30 min. 100 µl/well of human TNFα-biotin at a concentration of 100 ng/ml was then added, gently blown and mixed, and incubated for 30 min at 4° C. After washing twice with the staining buffer, 100 µl/well of PE-streptavidin was added and incubated at 4° C. for 30 min. After additional washing with the staining buffer twice, 150 µl resuspended cells was analyzed using an flow cytometry. Taking the logarithmic value of the antibody concentrations as abscissa and the corresponding MFI value as ordinate, the inhibition curve of the antibody was drawn, and the IC50 value was calculated by four parameters fitting. The lower the IC50 value, the stronger the ability of the antibody to inhibit the binding of human TNFα to human TNFR2. As the blocking curve shapes of some antibodies were different, the blocking effect of all antibodies was normalized to 002# using area under curve (AUC). The higher the percentage value, the better the antibody inhibition effect. The inhibition curves of the 11 antibodies are shown in FIG. 5, and the inhibitory activities are shown in Table 8.

Figure 5:
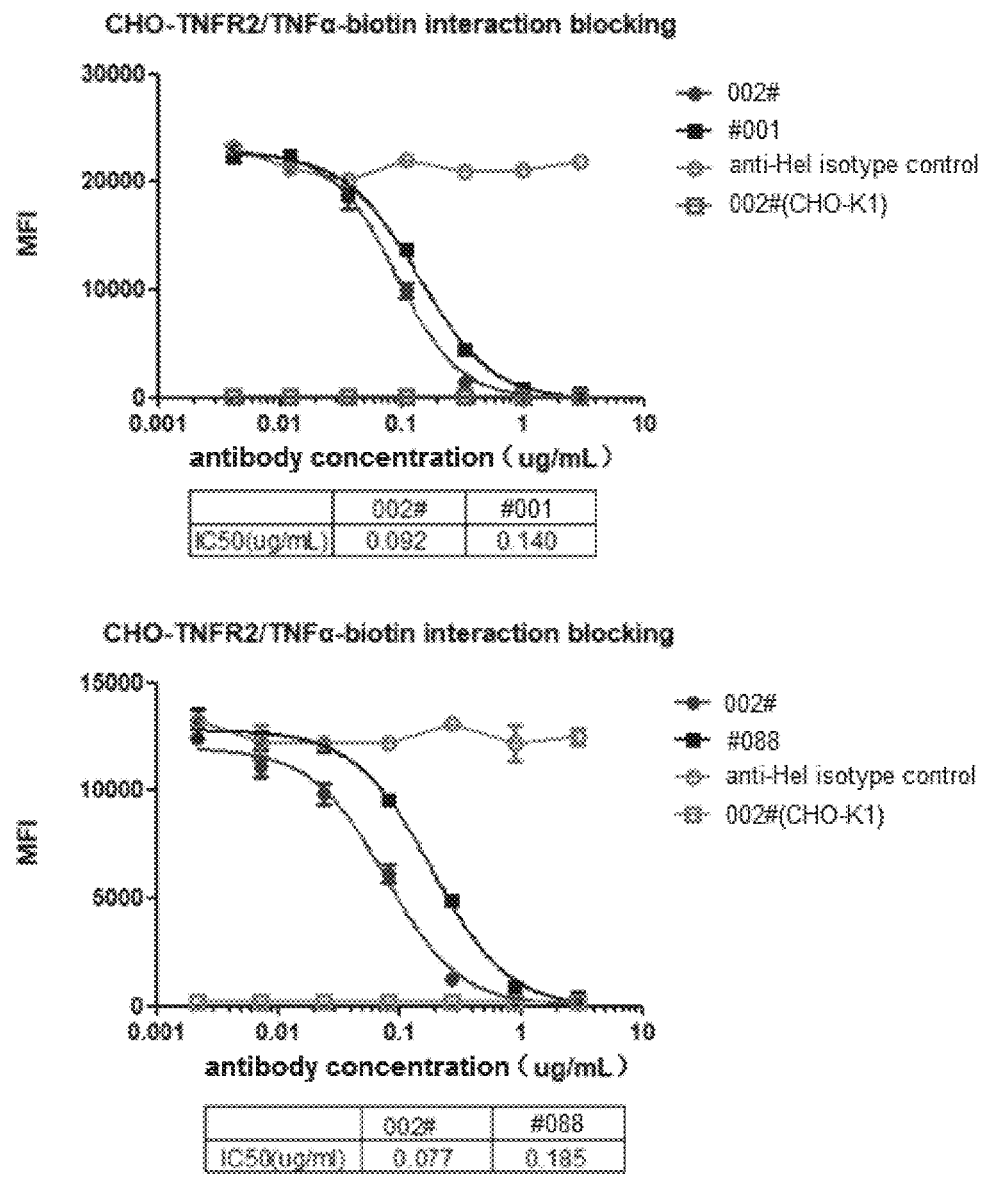
FIG. 5 shows that the test antibodies of the invention block the interaction between human TNFα and human TNFR2 expressed on CHO-TNFR2 cells. 002#Ab is a tool antibody, which is a positive control antibody in this experiment; anti-Hel isotype control is a negative control antibody; the cell control is CHO-K1 (used to construct the mother cell of CHO-TNFR2, which does not express human TNFR2).
Figure 5:
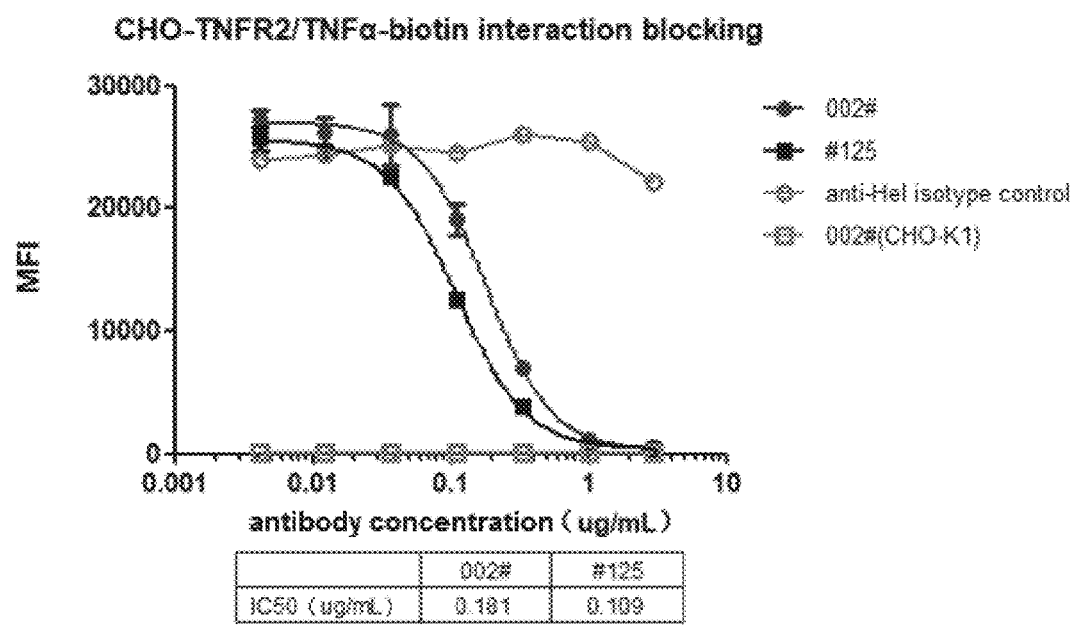
Figure 5:
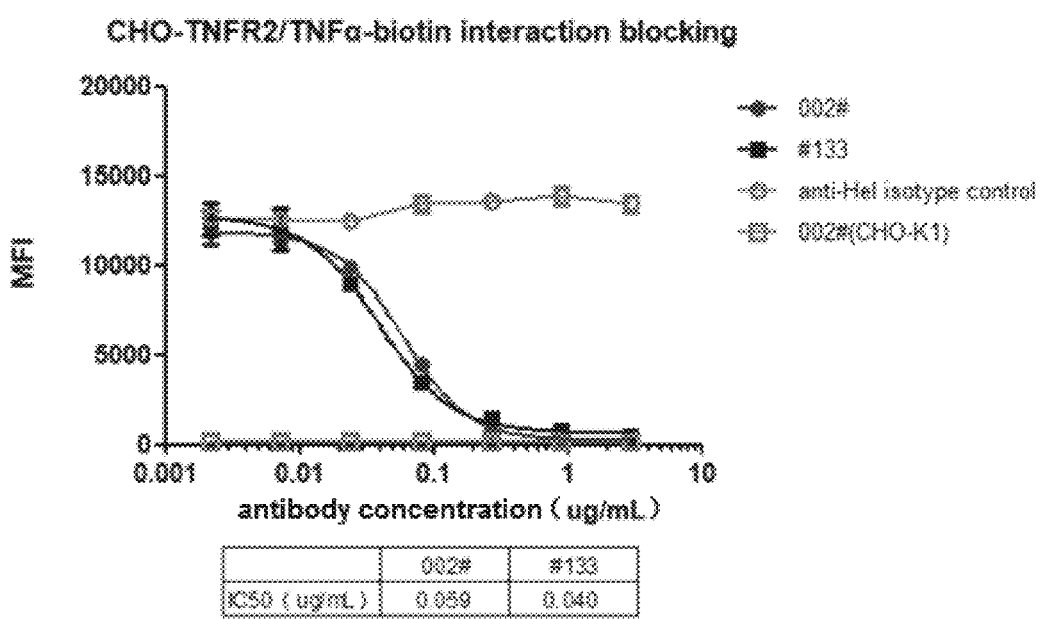
Figure 5:
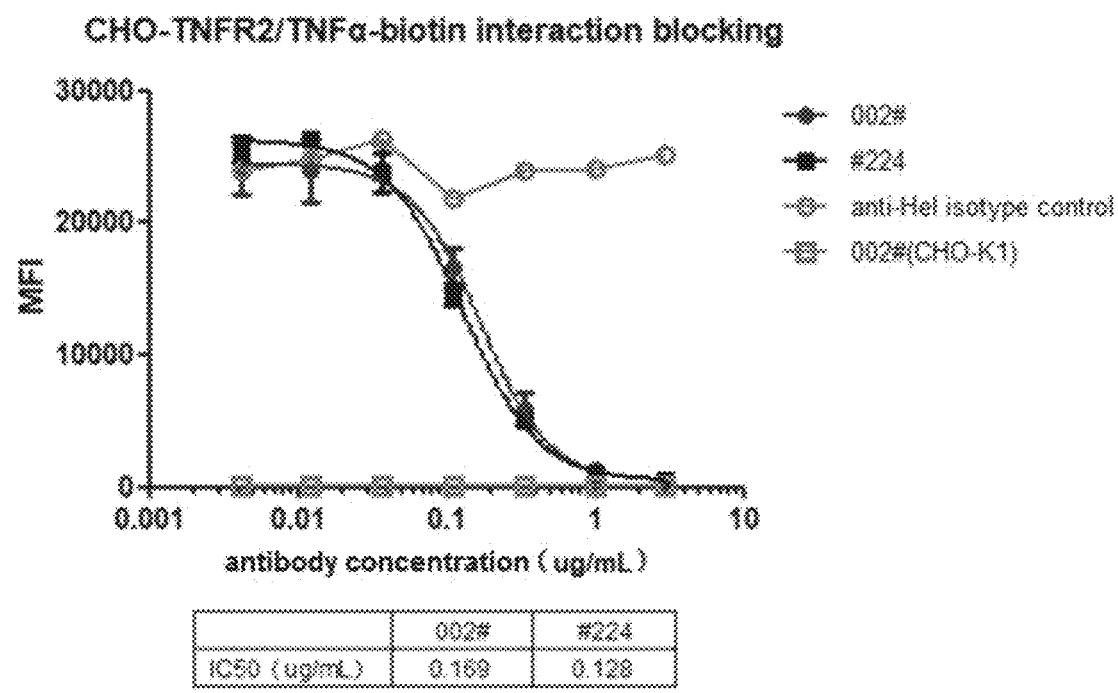
Figure 5:
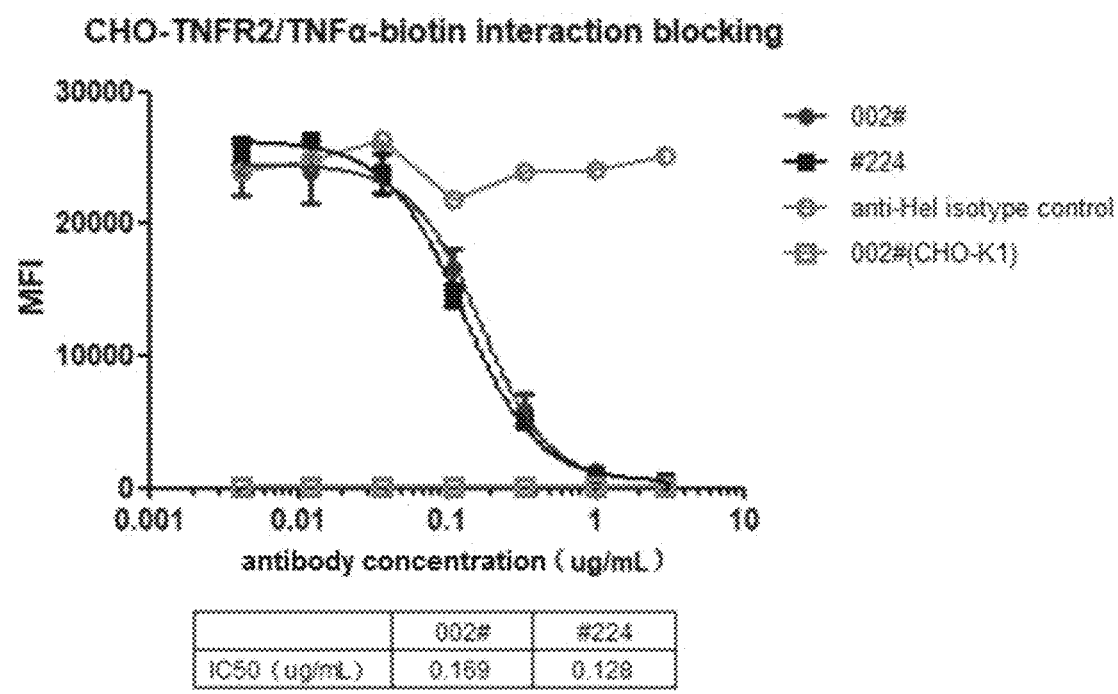
Figure 5:
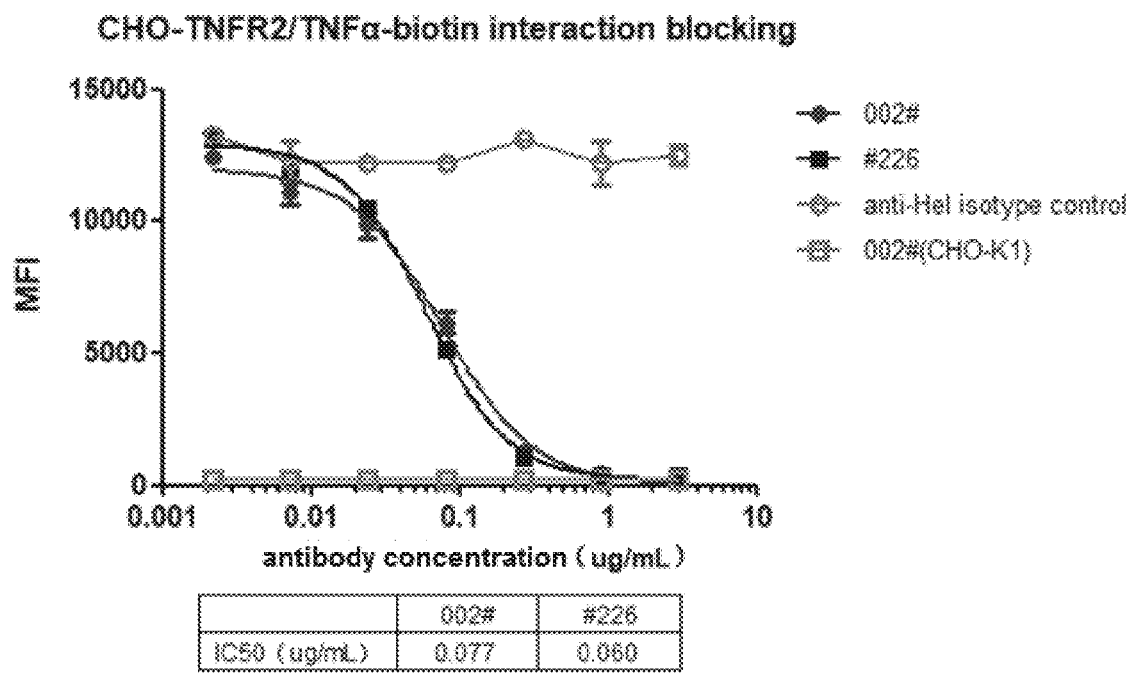
Figure 5:
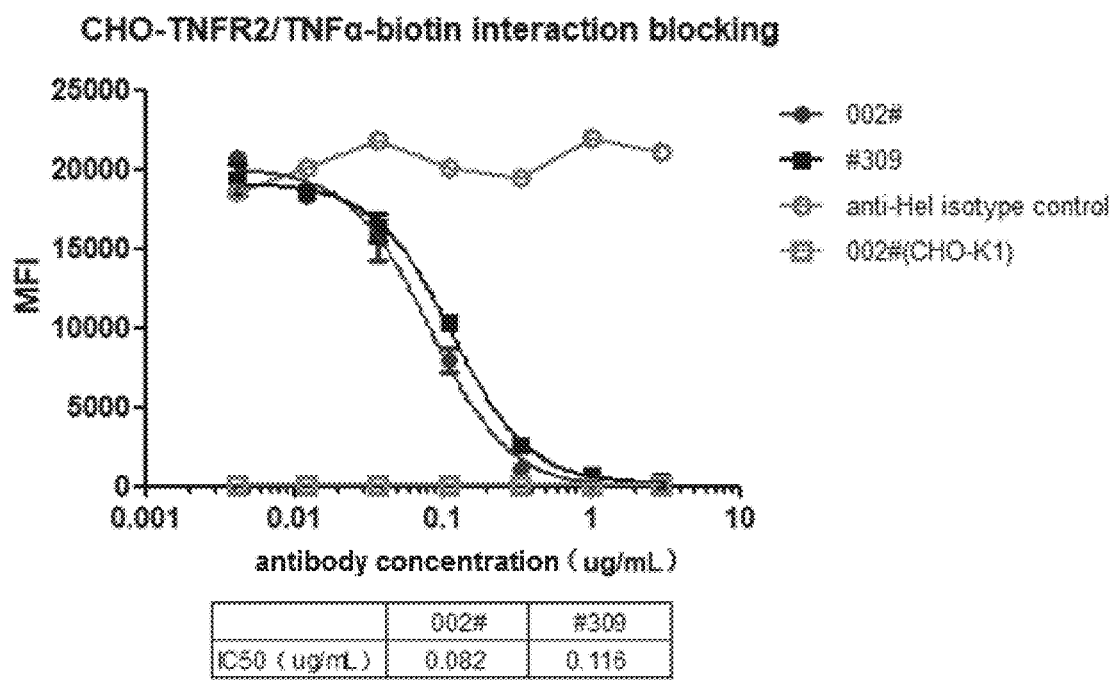
Figure 5:
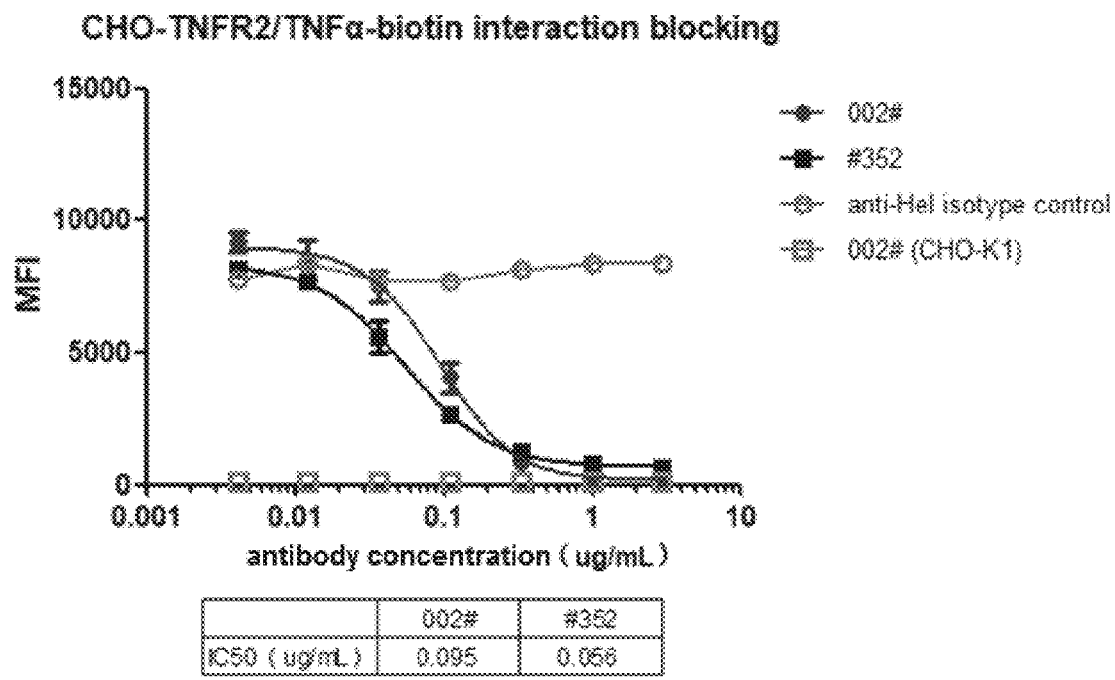
Figure 5:
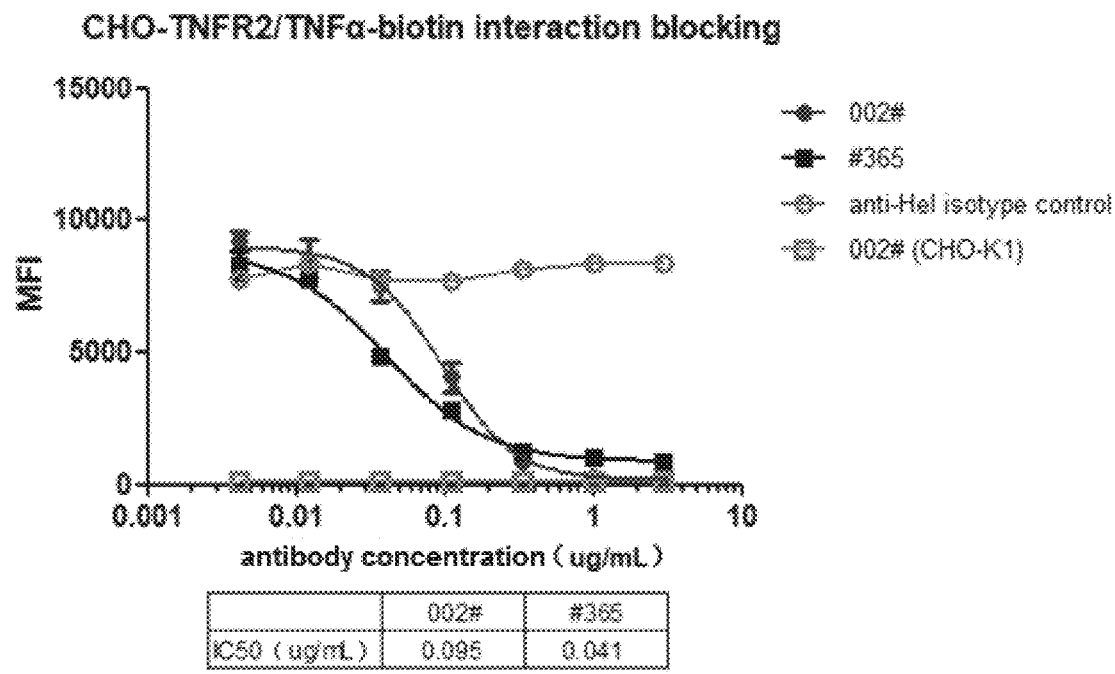
Figure 5:
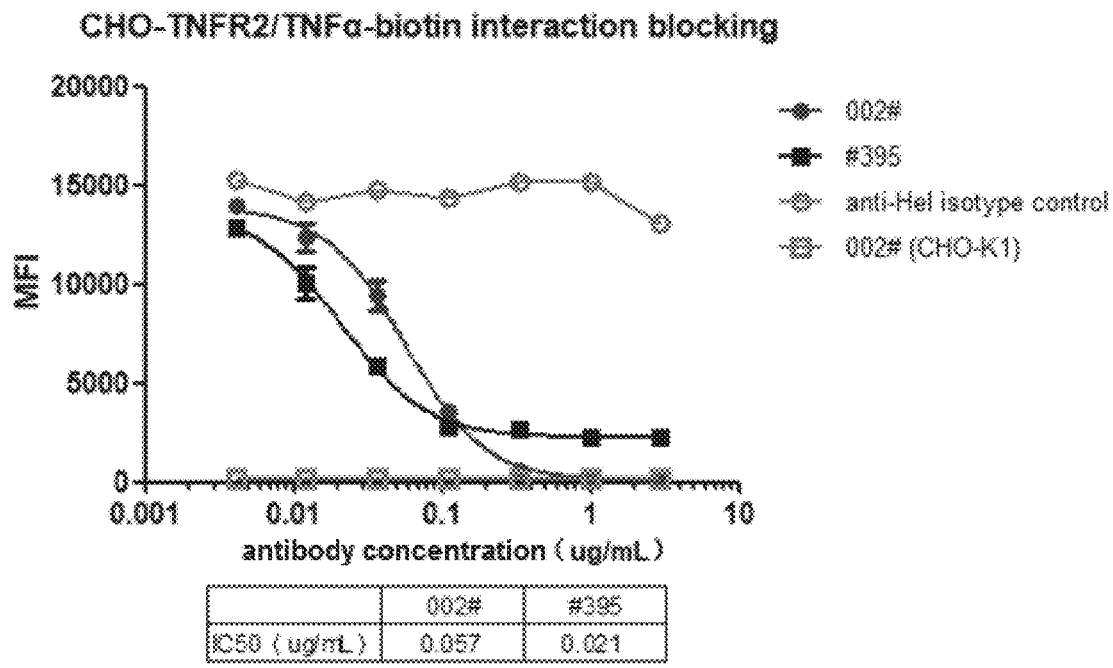

As can be seen from FIG. 5 and Table 8, all 11 antibodies from Example 1 can significantly inhibit the binding of TNFα to TNFR2 expressed on CHO-TNFR2 cells.

Example 10 Inhibition of Treg Function by Anti-TNFR2 Antibody

Figure 6:
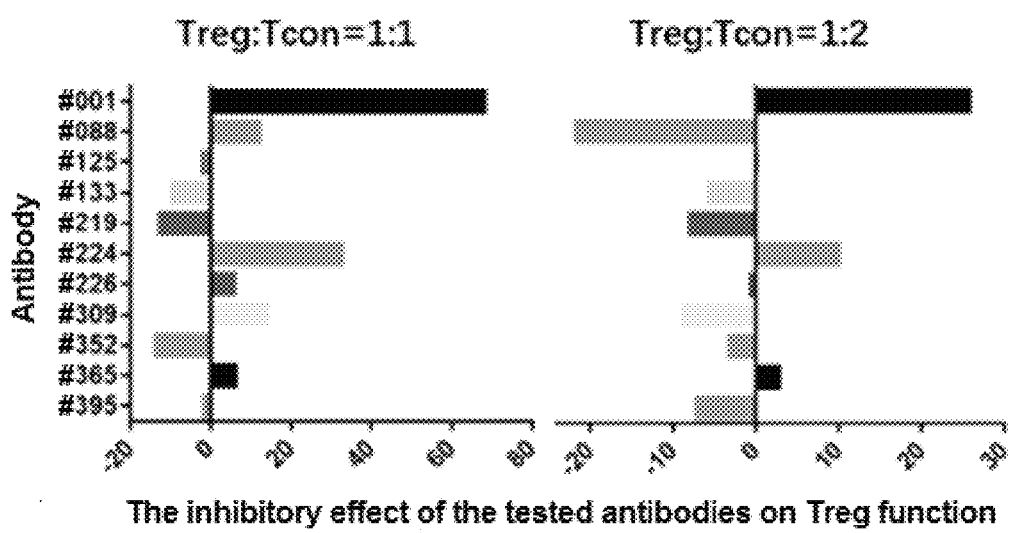
FIG. 6 shows the inhibitory effect of the test antibodies of the invention on Treg's inhibitory activity on Tcon cell proliferation. The ordinate shows different antibodies, the abscissa shows (proliferation ratio of responder cells under each antibody−proliferation ratio of responder cells under control antibody)/proliferation ratio of responder cells under control antibody×100%, the control antibody is anti-Hel, the experimental concentration of each antibody is 12.5 μg/ml, and the responder cells used are $CD4^+CD25^-$Tcon cells.

The interference of the antibody on the inhibitory effects of Treg cells was assessed by detecting the inhibitory effects of Treg cells on responder T cells under the condition of containing TNFR2 antibody. Treg ($CD4^+CD25^+FoxP3^+$ T cells) and Tcon responder cells ($CD4^+CD25^-$ T cells) were resuscitated and recovered overnight, centrifuged at 400×g for 5 minutes the next day. Cell were then resuspended with RPMI1640 medium (Gibco, Catalog No. 72400047) and counted for later use. Tcon cells were stained with CellTrace CFSE cell proliferation kit (Biolegend Catalog No. 423801) of which 1 ml of staining solution was prepared using 1 µl of storage solution for every $4\times10^6$ cells. Tcon cells were stained for 5 min, the staining process was quenched by adding the same volume of serum. Stained cells were then allowed to stand for 5 min, and centrifuged at 400×g for 5 min. The cells were resuspended and washed with the medium, and centrifuged again to discard the supernatant followed by seeding cells in 96-well plates at a density of $1\times10^5$ cells per well. Every $1\times10^5$ cells were resuspended with 50 µl medium and transferred to a 50 mL centrifuge tube. In the meantime, Treg cells were prepared. Treg cells and Tcon cells were co-cultured at ratios of 1:1, 1:2, 1:4 and 1:8. Each well of each 96-well plate corresponded to a different Treg cell density, and the cells in each well were resuspended with 50 µl medium. According to the total number of Tcon cells, corresponding anti-CD3/CD28 Dynabeads (Gibco, Catalog No. 11129D) were prepared at a ratio of ⅛, and added to the medium containing Treg and Tcon in a volume of 50 µl per well. Test antibodies were added to each well to make the final concentration of each test antibody to 12.5 g/ml. Replicate wells were set up for each condition. The above-mentioned plates were then put into a 37° C. incubator for 4 days for FACS analysis. The results show that antibody #001 and antibody #224 could in particular significantly suppress the inhibitory effect of Treg on Tcon cells and promote Tcon proliferation under different Treg/Tcon ratios (FIG. 6).

A formula for calculating the effect of the test antibodies from Example 1 on the inhibitory function of Treg cells compared to the isotype control anti-Hel antibody is as

TABLE 8

| | TNFR2 antibodies block binding of TNFα to TNFR2-CHO cell | | | | | |
|---|---|---|---|---|---|---|
| Antibodies | Sample IC50 (g/ml) | 002# IC50 (g/ml) | IC50 Relative Value % | Antibody AUC | 002# AUC | AUC % |
| 1 | 0.140 | 0.092 | 65.6 | 34295 | 30287 | 88.3 |
| 88 | 0.185 | 0.077 | 41.5 | 24346 | 18359 | 75.4 |
| 125 | 0.109 | 0.181 | 165.3 | 36957 | 44586 | 120.6 |
| 133 | 0.04 | 0.059 | 149.9 | 17313 | 17291 | 99.9 |
| 219 | 0.101 | 0.072 | 71.4 | 14928 | 13992 | 93.7 |
| 224 | 0.128 | 0.169 | 131.8 | 39967 | 40118 | 100.4 |
| 226 | 0.06 | 0.077 | 128.6 | 18592 | 18359 | 98.7 |
| 309 | 0.116 | 0.082 | 70.7 | 27790 | 25666 | 92.4 |
| 352 | 0.056 | 0.095 | 171.4 | 10662 | 12413 | 116.4 |
| 365 | 0.041 | 0.095 | 232.4 | 10618 | 12413 | 116.9 |
| 395 | 0.021 | 0.057 | 269.5 | 14851 | 15899 | 107.1 |

Note:
AUC % = AUC for 002 # ÷ AUG for antibody × 100.

follows: (proliferative capacity of responder T cells in the presence of the antibodies tested−proliferative capacity of responder T cells in the presence of anti-Hel antibody)/proliferative capacity of responder T cells in the presence of anti-Hel antibody×100%.

Figure 7:
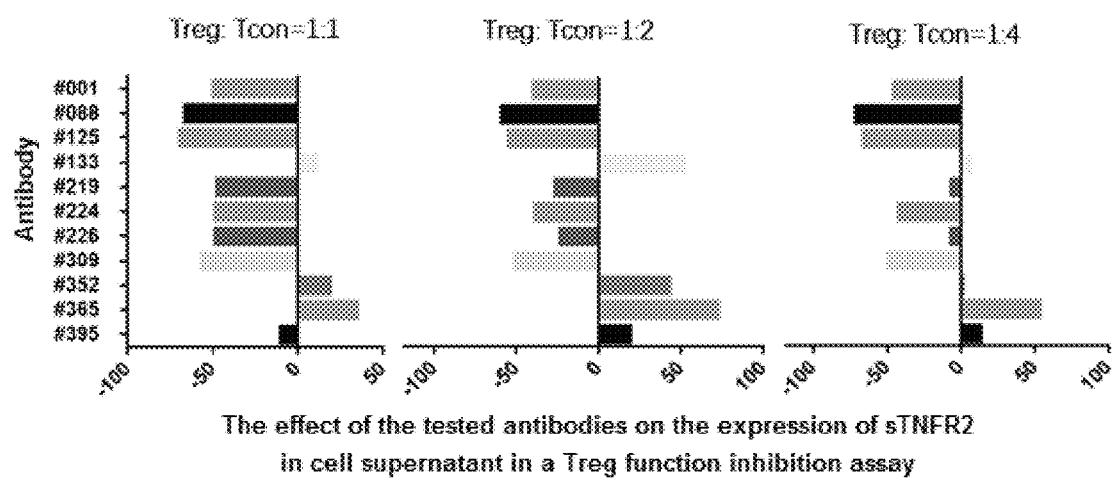
FIG. 7 shows the effect of the test antibodies of the invention on the expression of sTNFR2 in the cell supernatant in a Treg function inhibition assay. The ordinate shows different antibodies, the abscissa shows (the expression level of sTNFR2 in the cell supernatant of each test antibody−the expression level of sTNFR2 in the cell supernatant of control antibody)/the expression level of sTNFR2 in the cell supernatant of the control antibody×100%, the control antibody is anti-Hel antibody, and the experimental concentration of each antibody is 12.5 μg/ml.

Example 11. The Effect of TNFR2 Antibody on the Production of sTNFR2 in Cell Supernatant in a Treg Function Inhibition Assay The inhibitory effect of TNFR2 antibody on Treg function was assessed by measuring the level of sTNFR2 in the cell supernatant. Treg and responder T cells were treated with the antibodies from Example 1 for 4 days, 100 μl supernatant per well was collected as testing sample. Collected supernatant was then diluted 5 times for sTNFR2 assessment. Detailed detection method of sTNFR2 can refer to the instruction of human TNFRII/TNFRSF1B kit (Catalog No. DRT200) from R&D Company. Results show that #001, #088, #125, #219, #224, #226 and #309 can significantly down-regulate the level of sTNFR2 in the cell supernatant under different Treg:Tcon ratios (FIG. 7).

Figure 8:
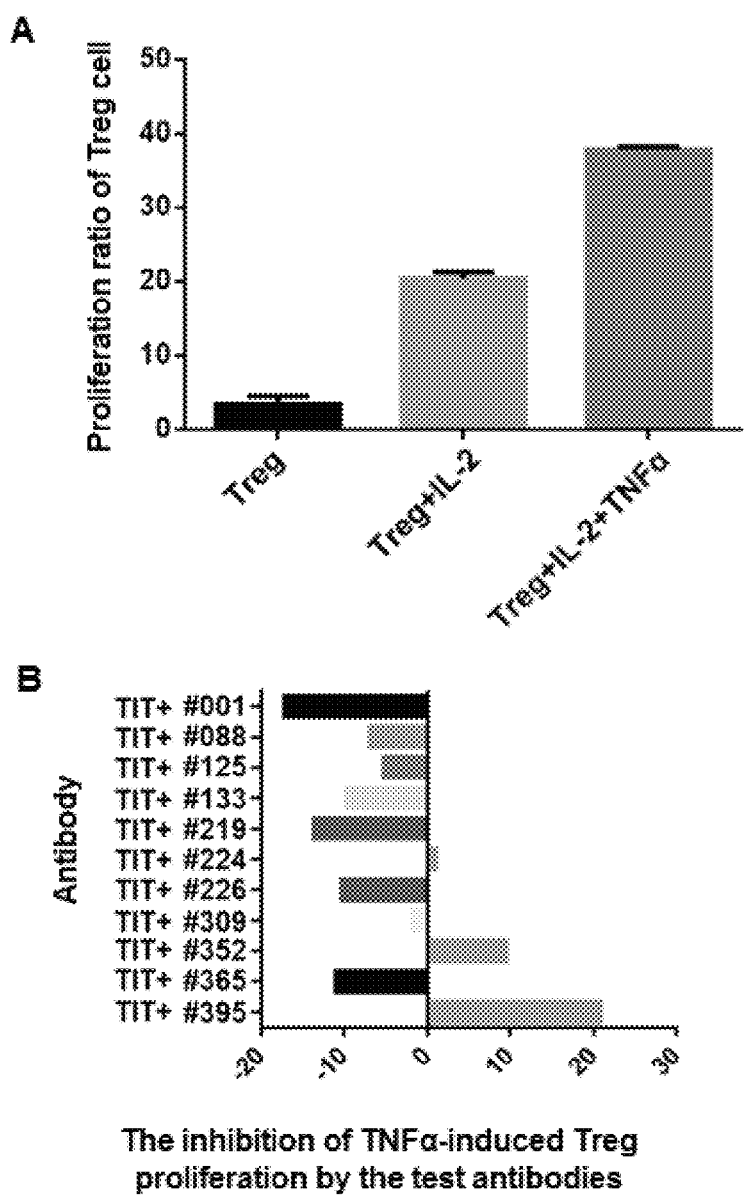
FIG. 8 shows the inhibition of TNFα-induced proliferation of Treg cells by the test antibodies of the invention.

Example 12 Inhibition of TNFR2 Antibody on the TNFα-Induced Proliferation of Treg Cells The inhibitory effect of TNFR2 antibody on TNFα-induced Treg cell proliferation was determined by measuring TNFα-induced proliferation of Treg cells in the presence of TNFR2 antibody (Zaragoza B et al., Nat Med. 2016 January; 22 (1): 16-7). Treg cells cryopreserved after in vitro expansion were resuscitated and recovered overnight, centrifuged at 400×g for 5 minutes the next day, resuspended with culture medium, and counted for later use. Treg were stained with CFSE, and 1 ml of staining solution was prepared using 1 μl of storage solution for every $4\times10^6$ cells. Treg cells were stained for 5 min, the staining process was quenched by adding the same volume of serum. Stained cells were allowed to rest for 5 min, and centrifuged at 400×g for 5 min. The cells were resuspended, washed once with medium, and centrifuged again to discard the supernatant. The cells were then seeded into 96-well plates at a density of $1\times10^5$ cells per well. $1\times10^5$ cells were resuspended with 50 μl medium and transferred to 96-well plates. Test antibodies from Example 1 were seeded to each well to make the final concentration of the antibody to 12.5 g/ml. The plates were then placed in an incubator for 30 minutes. Subsequently, 50 μl medium containing IL-2 (final concentration 300 IU) and another 50 μl medium containing TNFα with a final concentration of 50 ng/ml were added per well. Final volume is toped up to 200 μl per well with culture medium. Triplicate wells were set for each condition. The abovementioned wells were mixed and then put into a 37° C. incubator for 3 days prior to FACS analysis. The inhibitory effect of the antibody on TNFα-induced Treg proliferation was assessed by the percentage of Treg proliferation. As shown in FIG. 8, the following antibodies effectively inhibited TNFα-induced Treg cell proliferation compared to the control anti-Hel antibody: #001 (proliferation inhibition 17.1%), #088 (proliferation inhibition 6.9%), #125 (proliferation inhibition 5.2%), #133 (proliferation inhibition 9.7%), #219 (proliferation inhibition 13.6%), #226 (proliferation inhibition 10.3%), and #365 (proliferation inhibition 11.0%). Compared to the control antibody, the calculation formula for the ratio of the test antibody inhibiting the proliferation of Treg cells induced by TNFα is as follows: (proportion of TNFα-induced Treg proliferation in the presence of test antibody−proportion of TNFα-induced Treg proliferation in the presence of anti-Hel isotype antibody)/proportion of TNF-induced Treg proliferation in the presence of anti-Hel isotype antibody×100%. FIG. 8A shows a significant increase in the proliferation of Treg after the addition of IL-2 (20% vs. 4%) and a further increase in the proliferation ratio after the addition of TNFα (40% vs. 20%). FIG. 8B shows the inhibitory effect of 11 antibodies on the inducibility of Treg proliferation after the addition of IL-2 and TNFα, and 8 candidate antibodies except #224, #352 and #395 could inhibit IL-2 and TNFα-induced Treg proliferation.

Example 13 ELISA Detection of the Effect of TNFR2 Antibody on the Production of sTNFR2 in $CD4^+$ T Cell Culture Supernatant Commercial cryopreserved human PBMCs were resuscitated and rested overnight. After overnight resting, the human PBMCs were centrifuged at 300×g for 10 min to discard supernatant, and washed twice with a kit isolation Easybuffer, and then counted for later use. Human $CD4^+$ T cell isolation was performed according to the instructions of the human $CD4^+$ T cell isolation kit (Stemcell, EasySep™ Human $CD4^+$ T cell Isolation Kit, Catalog No. 17952). The isolated $CD4^+$ T cells were re-counted and resuspended to a suitable concentration followed by seeding into a 96-well round bottom plate at a density of $4\times10^5$ cells/well and a volume of 50 μl/well. An antibody working solution (50 μg/ml, 4×) was prepared and added to the plate at 50 μl/well followed by incubation at 37° C. with 5% $CO_2$ for 30 min. IL-2 working solution (800 IU/ml, 4×) and TNFα working solution (200 ng/ml, 4×) were then prepared and added to the plate at a volume of 50 μl/well, respectively. The experimental groups are: non-stimulation group, IL-2 stimulation group, TNF stimulation group, IL-$2^+$TNF co-stimulation group, and antibody+IL-$2^+$TNF co-stimulation group (i.e. the group to be tested). The plate with these experimental groups was put into an incubator and cultured for 3 days under the conditions of 37° C. and 5% $CO_2$. 3 days later, the culture supernatant was collected for sTNFR2 detection.

The human sTNFR2 standard was prepared, cell supernatant from the abovementioned experiment was taken, and assay was performed according to the instructions of the sTNFR2 ELISA kit (R&D System, Soluble TNF Receptor II Human ELISA Kit, Catalog No. DRT200). Experimental steps were as follows: 1) adding the cell supernatant and the standard 100 μl/well into the high affinity plate, and incubating for 2.5 h under slight shaking at room temperature (18-25° C.); 2) discarding the supernatant and washing the plate 4 times at 300 μl/well with wash buffer; 3) adding 100 μl/well of 1× Biotin labeled soluble human TNFR2 antibody after drying the plate, and incubating for 1 h under slight shaking at room temperature (18-25° C.); 4) discarding the supernatant and washing the plate 4 times at 300 μl/well with wash buffer; 5) adding 100 μl/well of 1×HRP-Streptavidin solution after drying the plate, and incubating for 45 min under slight shaking at room temperature (18-25° C.); 6) discarding the supernatant and washing the plate 4 times at 300 μl/well with wash buffer; 7) adding 100 μl/well of a TMB substrate solution after drying the plate, and incubating for 30 min under slight shaking at room temperature (18-25° C.) protecting from light, and 8) adding 50 μl/well of the reaction termination solution, and immediately detecting the OD450 value in a microplate reader.

Figure 9:
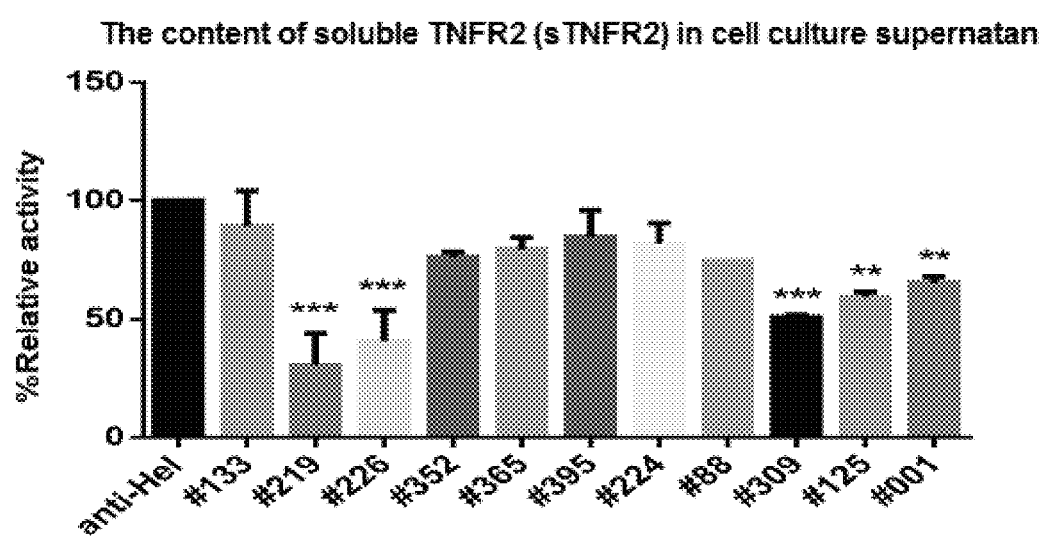
FIG. 9 shows ELISA result of the blocking effect of the test antibodies of the invention on sTNFR2 secretion of IL-2 and TNFα-induced $CD4^+$ T cells. The statistical analysis method is as follow: Graphpad prism 6, One-way ANOVA, $P<0.01$, * $P<0.001$.

As shown in FIG. 9, all 11 antibodies from Example 1 inhibit the secretion of sTNFR2 in the cell supernatant as compare to the negative control anti-Hel antibody group. Production of sTNFR2 in the culture supernatant increases while CD4+ T cells are activated under the co-stimulation of IL-2 and TNFα. All 11 antibodies can block the activation effect of IL-2 and TNFα on CD4+ T cells to varying degrees, among which the antibodies numbered #88, #219, #001 ($P<0.001$), #125, #224 ($P<0.01$) have particularly significant inhibitory effects, with statistically significant differences. The lower the value of OD450, the lower the expression level of sTNFR2, i.e. the stronger the antagonistic activity of the antibody.

Figure 10A:
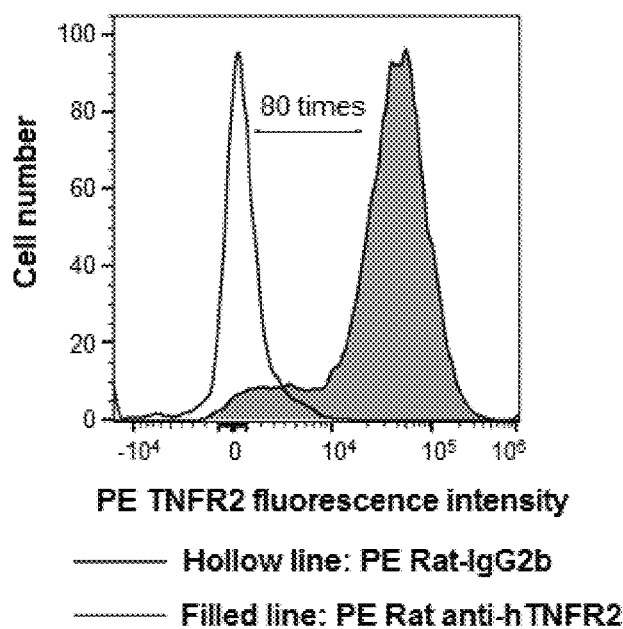
FIG. 10A shows the expression of TNFR2 on the target cell, i.e. Treg.
Figure 10B:
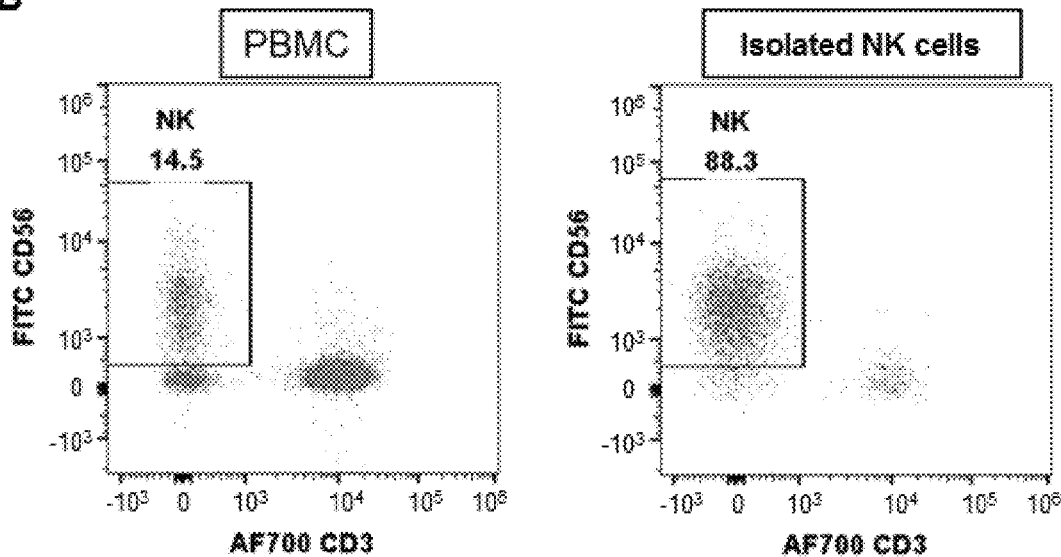
FIG. 10B shows a verification of the purity of effector NK cells isolated and enriched from human peripheral blood cells PBMC.
Figure 10C:
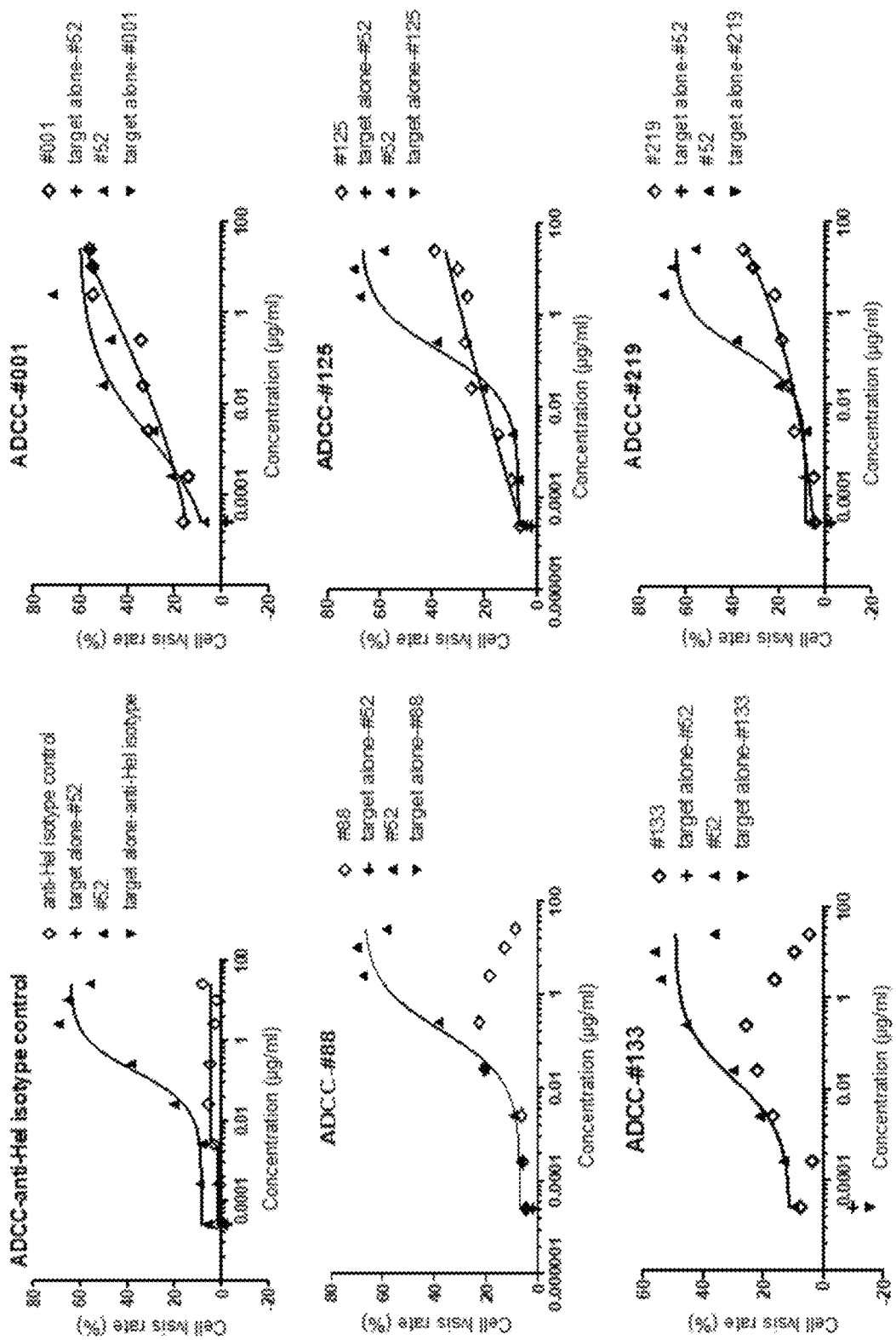
FIG. 10C shows the potency of the ADCC function of the test antibodies, wherein sample #52 is the ADCC positive control antibody interanally screened against the TNFR2 target, and the anti-Hel isotype control is the isotype negative control.
Figure 10C:
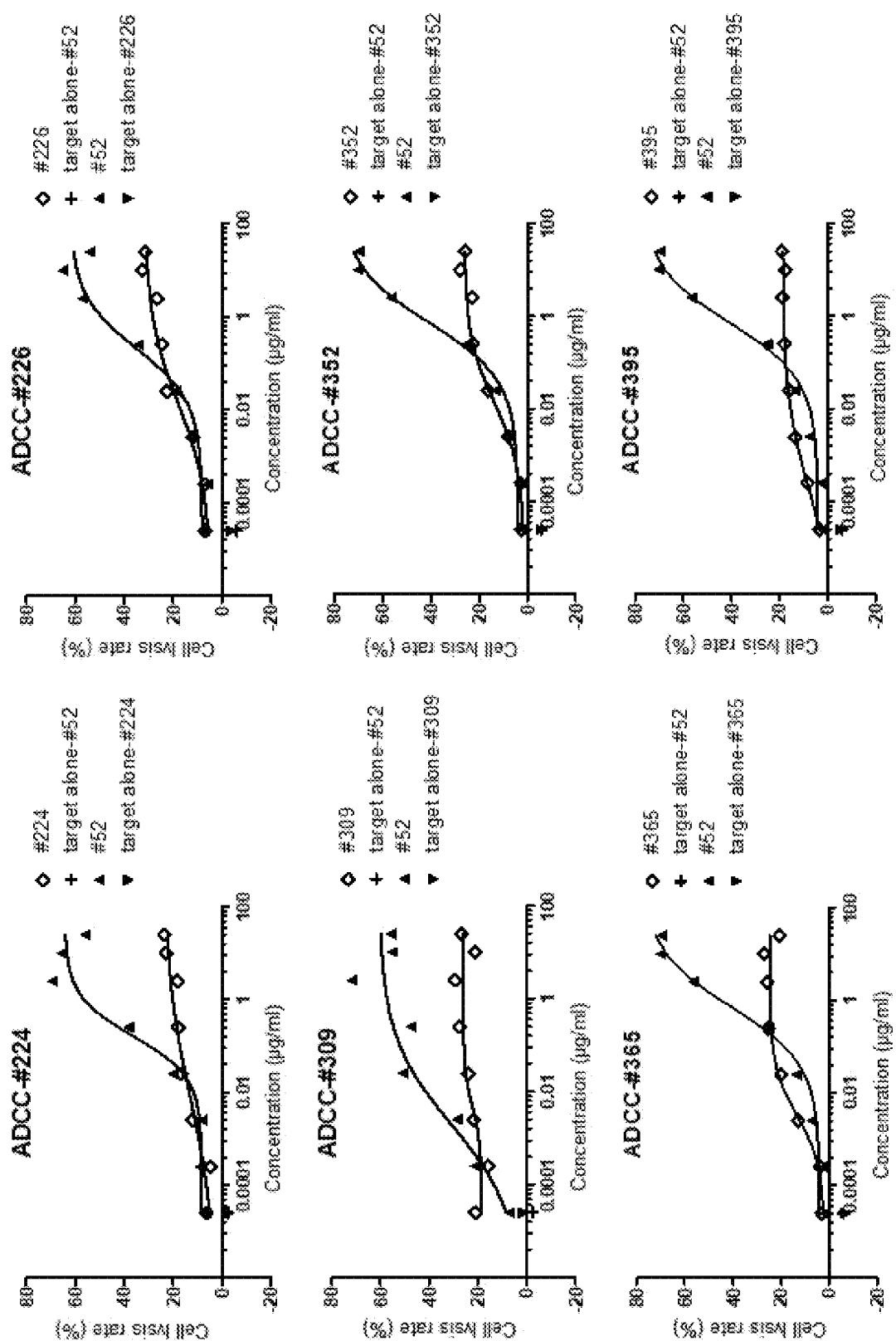

Example 14 FACS Assessment of TNFR2 Antibody-Mediated ADCC Activity Against Treg Cells PBMC and cryopreserved Treg cells were resuscitated one day in advance in complete medium (RPMI1640-Glutamax+10% FBS+1 XP/S+1×ITS+50 μl MPM mercaptoethanol), wherein 100 IU/ml IL-2 was added into PBMC cultures. On the experiment day, NK cells were isolated from PBMC according to the instructions of an isolation kit (Stemcell, Catalog No. 17955) and resuspended with the complete medium (without IL-2) at a density of $0.45×10^6$/ml. Treg cells were labeled with a Cell Trace violet reagent, and the cell density was adjusted to $0.3×10^6$/ml after labeling. 11 candidate antibodies were prepared in 4-fold gradient dilution with the complete medium. Target cells were seeded into the plate at a volume of 50 μl/well according to plate map followed by the addition of diluted antibodies to corresponding wells and incubated for 30 minutes at 37° C. After incubation, 100 μl of effector cell suspension was added to the required wells whereas the non-required wells were filled with 100 μl culture medium and incubated for 4 h at 37° C. 1 μl of PI dye was added to each well prior to detection in a FACS machine. The stronger the PI signal in the target cells, the more significant the ADCC effect was. ADCC test results (FIG. 10 and Table 9) show that the negative control anti-Hel isotype has no ADCC killing effect whereas the positive control #52 shows significant ADCC function. All 11 test antibodies show limited ADCC activity. FIG. 10A shows that human Tregs overexpress TNFR2, with an 80-fold MFI shift compared to the staining of the anti-Hel isotype control antibody. FIG. 10B shows that the ratio of NK cells in PBMC before isolation with the kit is 14.5%, and the purity of NK cells after isolation reaches 88.3%. FIG. 10C shows the ADCC effect of 11 antibodies, with #52 antibody being a positive control antibody, anti-Hel isotype antibody being a negative control antibody, and Target alone being a cell negative control with no NK cells but only the target Treg cells.

TABLE 9

Comparison of ADCC curve AUC (area under the ROC curve) of test antibodies against Treg

| ID | % AUC versus positive control (#52) |
|---|---|
| 1 | 80.80 |
| 88 | 45.32 |
| 125 | 69.56 |
| 133 | 46.63 |
| 219 | 52.72 |
| 224 | 48.07 |
| 226 | 69.03 |
| 309 | 56.02 |
| 352 | 61.40 |
| 395 | 59.33 |
| 365 | 70.65 |

Note:
Relative ADCC activity is calculated as the AUC value of the ADCC curve of the tested antibody divided by that of the positive control #52 antibody.

Figure 11:
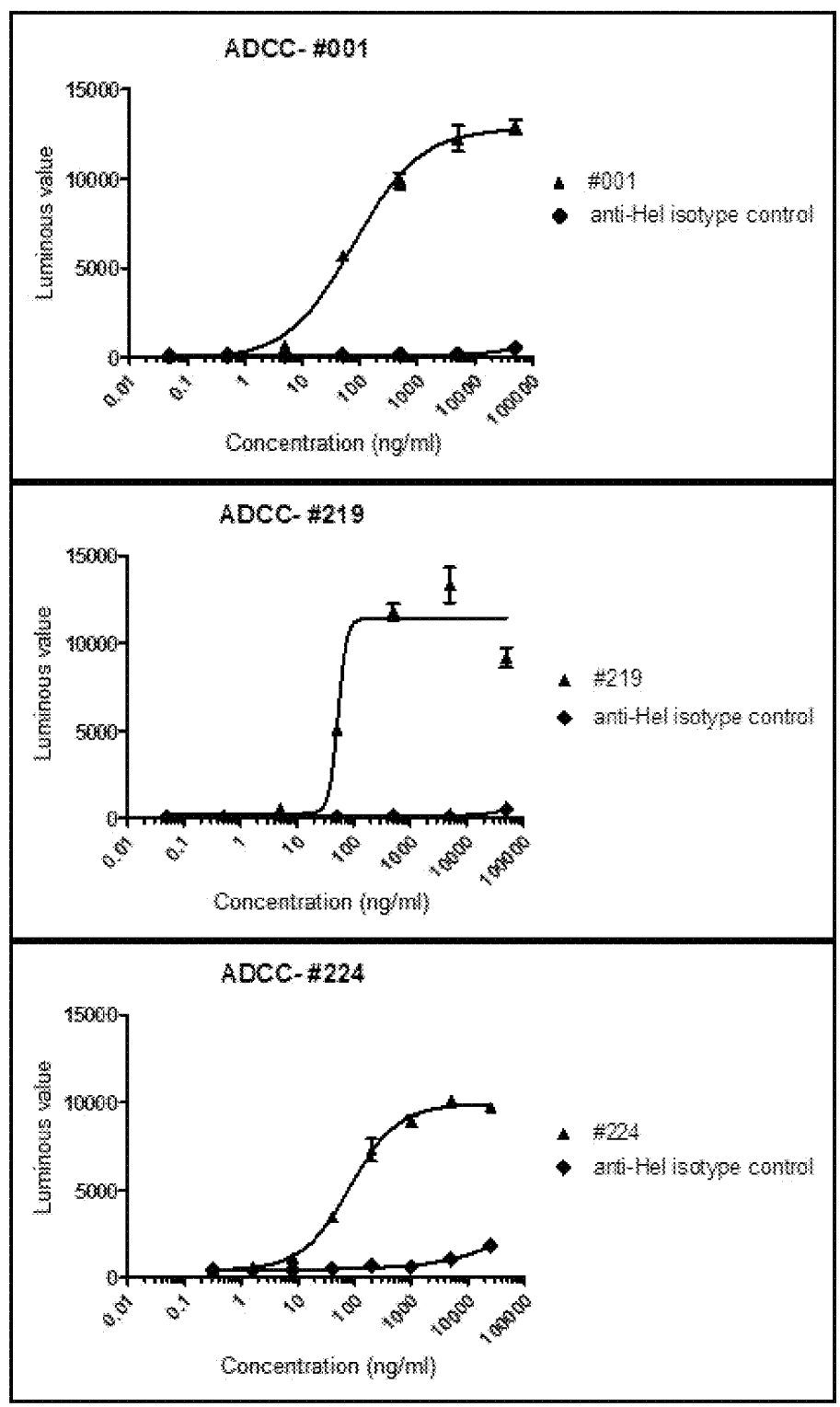
FIG. 11 shows the ADCC killing effect of the test antibodies of the invention on CHO-TNFR2 cells overexpressing human TNFR2. Among them, #219, #224 and #001 are the test antibodies, and anti-Hel isotype control is the negative control antibody.

Example 15 A Reporter Gene Assay for the Assessment of TNFR2 Antibody-Mediated ADCC Activity Against CHO-TNFR2 Cells Target cells (CHO-TNFR2) were seeded into a white transparent-bottom 96-well plate (Corning, Catalog No. 3610) with detection buffer (RPMI1640 (Gibco, Catalog No. 22400105)+0.5% FBS (Gibco, Catalog No. 10099141)+1× P/S (Gibco, Catalog No. 15140-122)) at a cell number of 10,000 cells per well one day in advance allowing the cells to be well adherent to the plate bottom. On the next day, the drug was gradiently diluted to 2 fold of the final concentration with the detection buffer for latter use. The detection buffer in the plate was discarded, 25 μl new detection buffer was added to each well followed by the addition of diluted drug into corresponding wells with a volume of 25 μl per well, and incubated with the target cells for 1 hour at 37° C. After incubation, 25 μl of 2× drug was added to the corresponding wells followed by the addition of 25 μl ADCC cell suspension (BPS, Catalog No. 60541) in 75000 cells per well. 100 μl mixed cell suspensions per well were then incubated in an incubator for 6 hours. After incubation, the plate was put at room temperature for 10 minutes, to which a Bright-Glo (Promega, Catalog No. 2620) reagent pre-warmed to room temperature was added in 100 μl per well, and placed on a shaker for shaking at 500 rpm for 10 minutes. The luminescence value was recorded with the use of a microplate reader. The stronger the luminescence signal, the more significant the ADCC effect. The results of ADCC experiment show that the negative control anti-Hel isotype control antibody does not have ADCC killing effect as it has no binding to the target, however, the detected anti-TNFR2 antibodies #001, #219 and #224 all have ADCC effects (FIG. 11).

Example 16 Epitope Binning of Candidate Anti-TNFR2 Antibodies

Biacore was used to detect antibody competition among candidate anti-TNFR2 antibodies to group the antibodies, and preliminarily determined how many epitope bins they belonged to (Abdiche Y N et al., Plos One. Mar. 20, 2014). Amino coupling was used to immobilize human TNFR2 protein. Selected antibodies were injected first followed by the injection of secondary antibodies until all test antibodies were alternated. By comparing whether there was a difference in the binding signals of the first injected antibodies and secondly injected antibodies and vice versa to human TNFR2, the binding epitope relationship among those antibodies on human TNFR2 protein could be determined. Specifically, in each cycle, all antibodies were determined by injection at a concentration of 300 nM for 180 s, and the antibodies to be tested were eluted with 650 mM HCl solution.

Results from Table 10 show that antibody 224 binds to different epitope with other 10 test antibodies.

TABLE 10

Biacore results of epitope binning of
TNFR2 antibody on human TNFR2 protein
Summary of Epitope binding results

|  | # 001 | # 088 | # 125 | # 133 | # 219 | # 224 | # 226 | # 309 | # 352 | # 365 | # 395 |
|---|---|---|---|---|---|---|---|---|---|---|---|
| # 001 | Y | Y | Y | Y | Y | N | Y | Y | Y | Y | Y |
| # 088 | Y | Y | Y | Y | Y | N | Y | Y | Y | Y | Y |
| # 125 | Y | Y | Y | Y | Y | N | Y | Y | Y | Y | Y |
| # 133 | Y | Y | Y | Y | Y | N | Y | Y | Y | Y | Y |
| # 219 | Y | Y | Y | Y | Y | N | Y | Y | Y | Y | Y |
| # 224 | N | N | N | N | N | Y | N | N | N | N | N |
| # 226 | Y | Y | Y | Y | Y | N | Y | Y | Y | Y | Y |
| # 309 | Y | Y | Y | Y | Y | N | Y | Y | Y | Y | Y |
| # 352 | Y | Y | Y | Y | Y | N | Y | Y | Y | Y | Y |
| # 365 | Y | Y | Y | Y | Y | N | Y | Y | Y | Y | Y |
| # 395 | Y | Y | Y | Y | Y | N | Y | Y | Y | Y | Y |

Note:
Y: with epitope competition;
N: without epitope competition

Example 17 In Vivo Efficacy Evaluation of
Anti-Murine TNFR2 Surrogate Antibody

Since the 11 anti-human TNFR2 antibodies from Example 1 specifically bound to human and cynomolgus TNFR2, but not mouse TNFR2, anti-mouse TNFR2 antibody was used as surrogate antibody to perform TNFR2 target-related efficacy experiments in a PD-1/PD-L1 therapy relatively resistant CT26 WT mouse colon cancer model which derived from Balb/c mouse. The surrogate antibody anti-mTNFR2 was purchased from BioXcell (Catalog No. BE0247). Mice were subcutaneously inoculated with $1 \times 10^5$ ct26 colon cancer cells on the right flank (set as day 0 of the experiment). When the tumor volume reached ~110 mm$^3$, mice with proper tumor volume were selected and randomly divided into 4 experimental groups using an EXCEL random number method (G1 as a control group, G2 as an anti-mTNFR2 surrogate antibody group, G3 as an anti-mPD-L1 (BioXcell, Catalog No. BE0101) antibody group, G4 as an anti-mPD-1 (BioXcell, Catalog No. BE0146) antibody group), with 8 mice in each group. The antibodies were administered intraperitoneally twice a week starting on the day of grouping (day 13) with doses of anti-mTNFR2 5 mg/kg (mpk), anti-mPD-L1 10 mg/kg (mpk) and anti-mPD-1 10 mg/kg (mpk). The tumor volume and body weight were measured three times a week at a fixed time.

Figure 12:
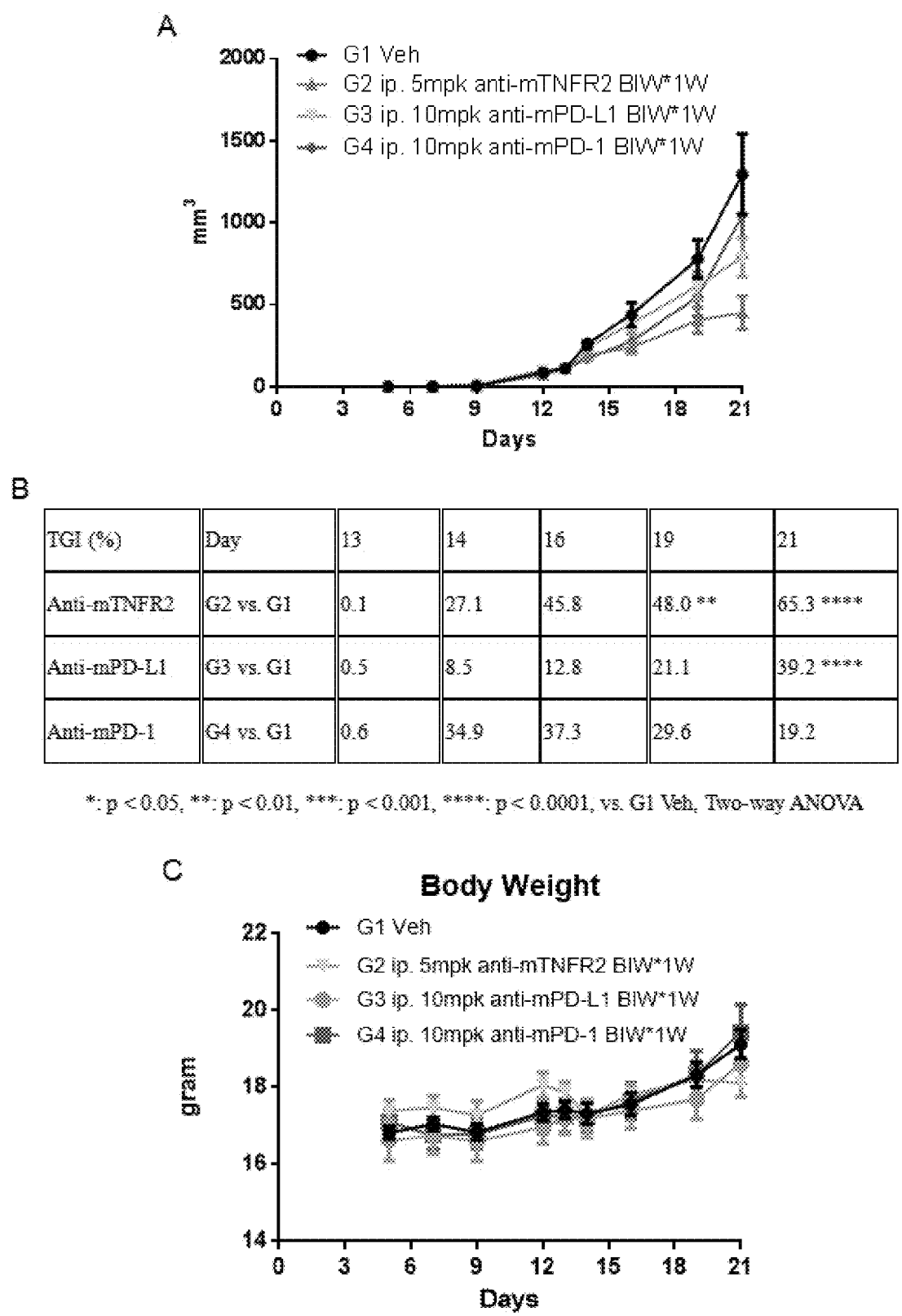
FIG. 12 shows the in vivo efficacy result of PD-1 antibody-resistant CT26 tumor cells, including change of tumor growth curves ($mm^3$, 12A), tumor growth inhibition % (TGI %) (12B) and the change of mouse body weight (12C) of each dosing group.

On the 21st day after tumor inoculation, compared to the control group, the tumor growth in the anti-mTNFR2 antibody treated group and the anti-mPD-L1 antibody treated group were significantly inhibited (P<0.05) within which the anti-mTNFR2 group showed a larger tumor growth inhibition (TGI) value than that of the anti-mPD-L1 group. The results show that the anti-mTNFR2 antibody has better efficacy on the CT26 tumor model than either the anti-PD-1 or anti-PD-L1 antibody treatments (FIGS. 12A-B).

During the administration period, the experimental animals in each group were in good activity and eating state, and their body weight increased to a certain extent. The results show that the anti-mTNFR2 antibody treatment is well tolerated (FIG. 12C).

Figure 13A:
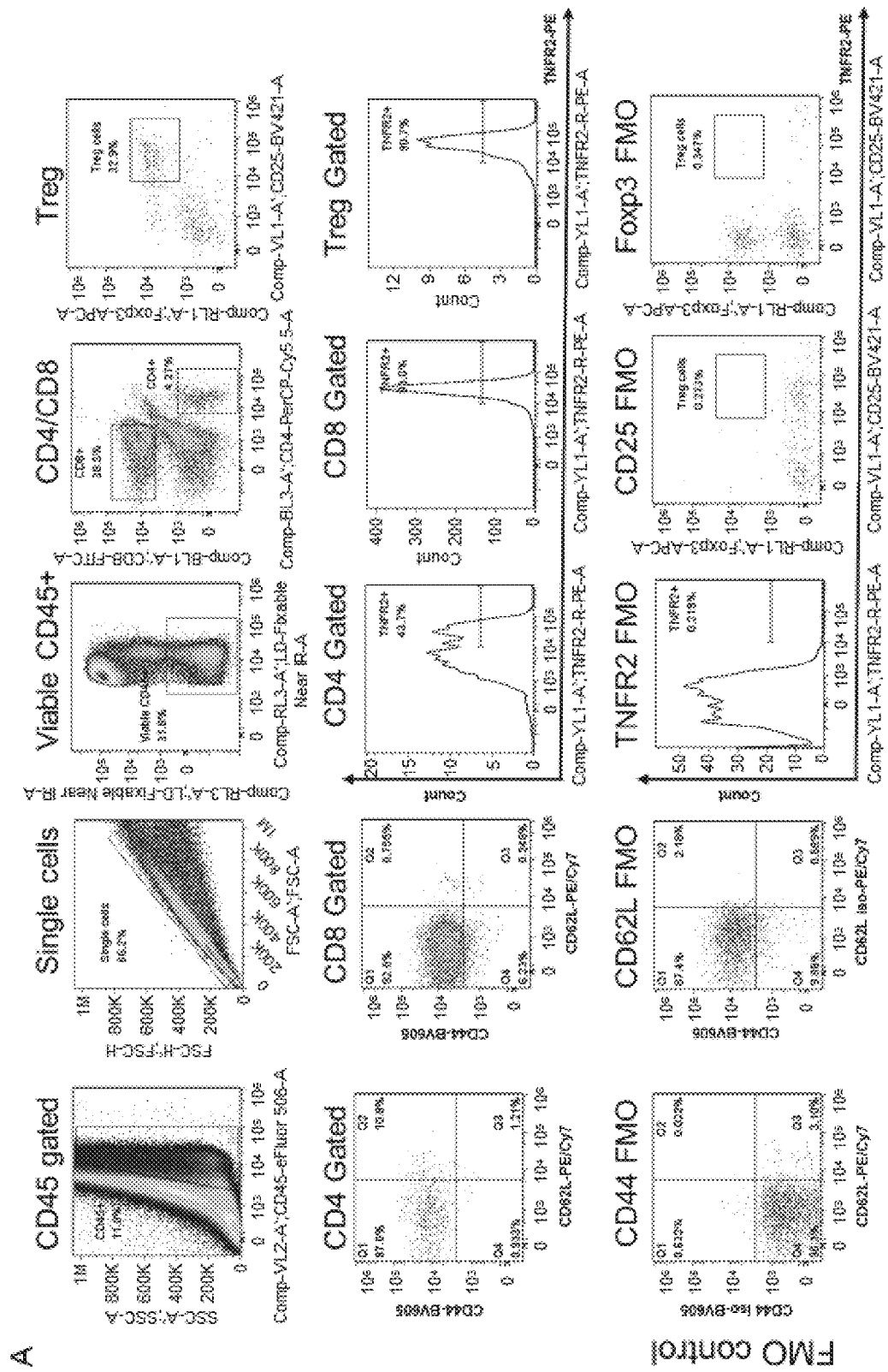
FIG. 13 shows the analysis of each immune cell subset in tumor infiltrated lymphocytes (TIL) in tumor tissues of mice for the CT26 in vivo efficacy experiment. 13A and 13B are the gating strategies of panel 1 and panel 2 in FACS immunophenotyping.
FIG. 13C shows the study on the percentages of $CD4^+$ T, $CD8^+$ T and Treg Cells in FACS immunophenotyping.
FIG. 13D shows the study of the ratio of total $CD8^+$ T cells to Treg cells in FACS immunophenotyping.
FIG. 13E shows the study of the ratio of memory $CD8^+$ T cells to Treg cells in FACS immunophenotyping.
FIG. 13F shows the study of the level of PD-1, LAG-3 and TNFR2 expressed on CD8+T in FACS immunophenotyping.
Figure 13B:
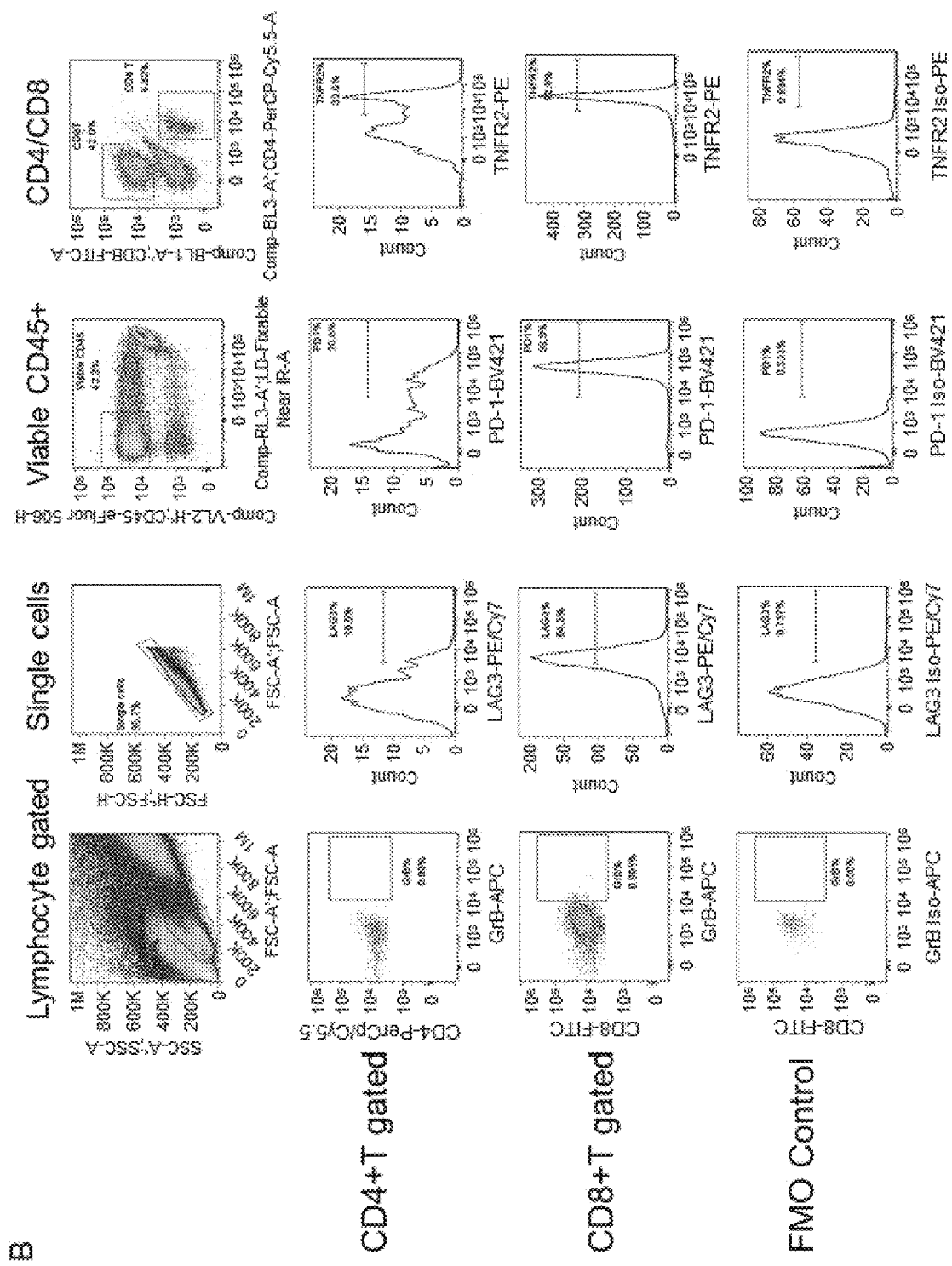
Figure 13C:
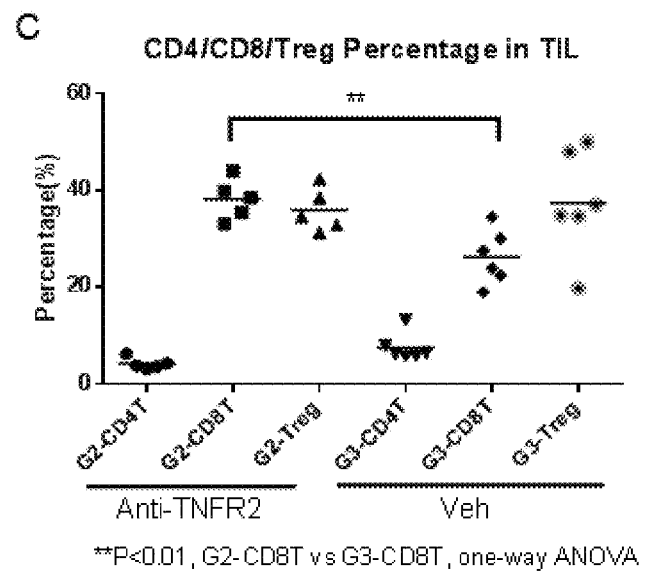
Figure 13D:
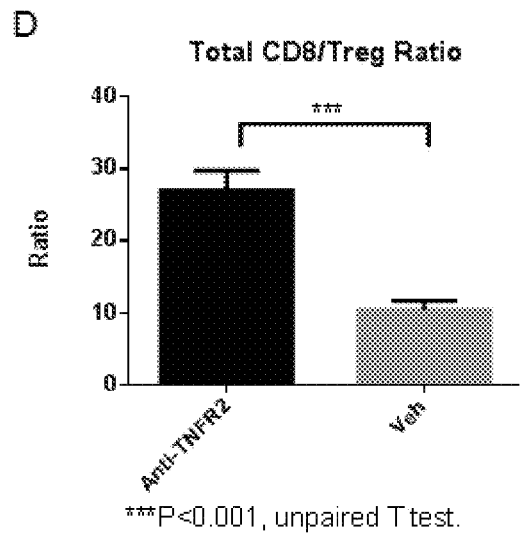
Figure 13E:
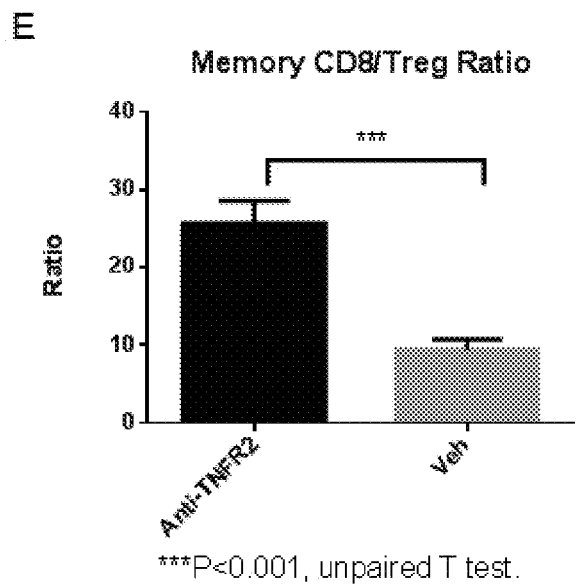
Figure 13F:
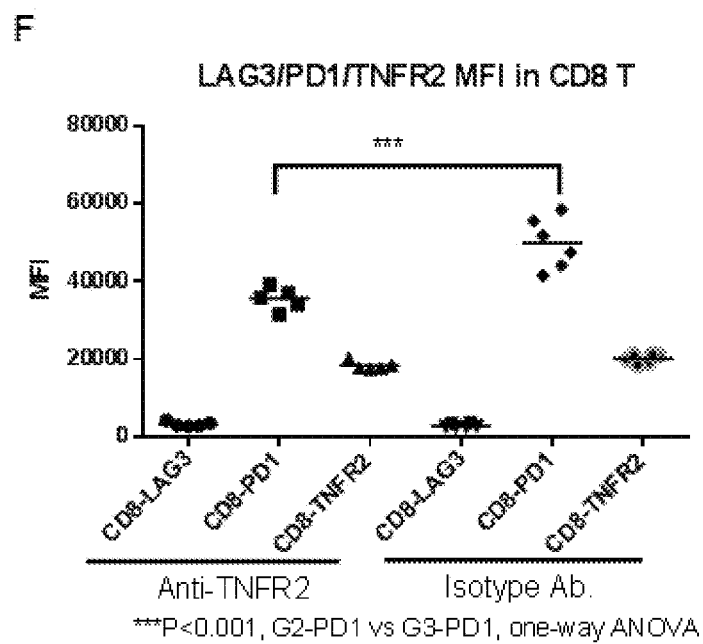

24 hours after the final dosing, most mice in the G1 control group and the G2 anti-mTNFR2 antibody group were selected for TIL FACS analysis. All cell populations were gated according to FMO controls (FIG. 13A-B). The result shows that CD8$^+$ T percentage in the anti-mTNFR2 surrogate treated group is significantly higher than that in the control group (P<0.01) (FIG. 13C). In the meantime, the ratios of total CD8$^+$ T and memory CD8$^+$ T cells to Treg cells (CD8$^+$ T/Treg) in the anti-mTNFR2 treatment group are also significantly higher than those in the control group (p<0.001) (FIG. 13D-E). The mean fluorescence intensity of PD-1 expressed on CD8$^+$ T in the anti-mTNFR2 antibody treated group is evidentially lower than that in the isotype control group (p<0.001) (FIG. 13F). The abovementioned data suggest that the anti-tumor effect of anti-mTNFR2 antibody may be explained by the increased ratio of CD8$^+$ T/Treg and partially reversed exhausted status of CD8$^+$ T cells.

The calculation formula of tumor volume (TV) is: $V=\frac{1}{2} \times a \times b^2$, where a and b represent length and width, respectively. The relative tumor volume (RTV) was calculated based on the measured results, and the calculation formula is: RTV=Vt/V0, where V0 is the tumor volume measured at the time of grouping (i.e. day 0), and Vt is the tumor volume measured at each time points. TGI %=[1−RTV (experimental group)/RTV (control group)]×100%.

Example 18 In Vivo Efficacy Assessment of
Anti-Murine TNFR2 Surrogate Antibody in
Combination with Anti-Murine PD-1 Surrogate
Antibody Mice were subcutaneously inoculated with $1 \times 10^5$ CT26 colon cancer cells on the right flank (set as day 0 of the experiment). When the tumor volume reached ~100 mm$^3$, mice with proper tumor volume were selected and randomly divided into 6 experimental groups using an EXCEL random number method (G1 as a control group, G2 as an anti-mTNFR2 antibody group, G3 as an anti-mPD-1 antibody group, G4 as an anti-mTNFR2+anti-mPD-1 antibody group), with 9 mice in each group. The antibodies were administered intraperitoneally twice a week starting on the day of grouping (day 14) with doses of anti-mTNFR2 5 mpk and anti-mPD-1 10 mpk. The tumor volume and body weight were measured three times a week at a fixed time.

Figures 14A, 14B:
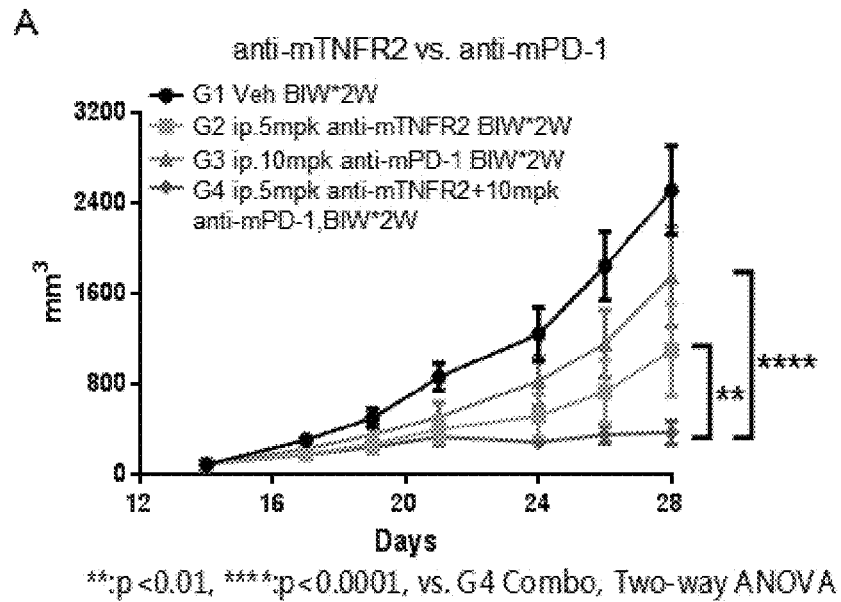
FIG. 14 shows the CT26 in vivo efficacy experiment result of 4 experimental groups which are performed with vehicle, anti-TNFR2 antibody alone, anti-PD-1 antibody alone or combination of the abovementioned two antibodies. 14A shows the change of tumor growth curves ($mm^3$), 14B shows the change of tumor growth inhibition rate (TGI %) and the 14C shows the survival curve of mice.

On the 28th day after tumor inoculation, compared to the control group, the tumor growth in the G2 anti-mTNFR2 group and the G3 anti-mPD-L1 group were significantly inhibited (P<0.05) within which the anti-mTNFR2 group showed a larger tumor growth inhibition (TGI) value than that of the anti-mPD-L1 group. The results show that the anti-mTNFR2 antibody has better efficacy on this animal model. The G4 combination treatment group has the best efficacy among all treatment groups (p<0.01, p<0.001), indicating efficacy synergy can be achieved when combine the anti-mTNFR2 and anti-mPD-1 treatments. (FIGS. 14A-B).

Figure 14C:
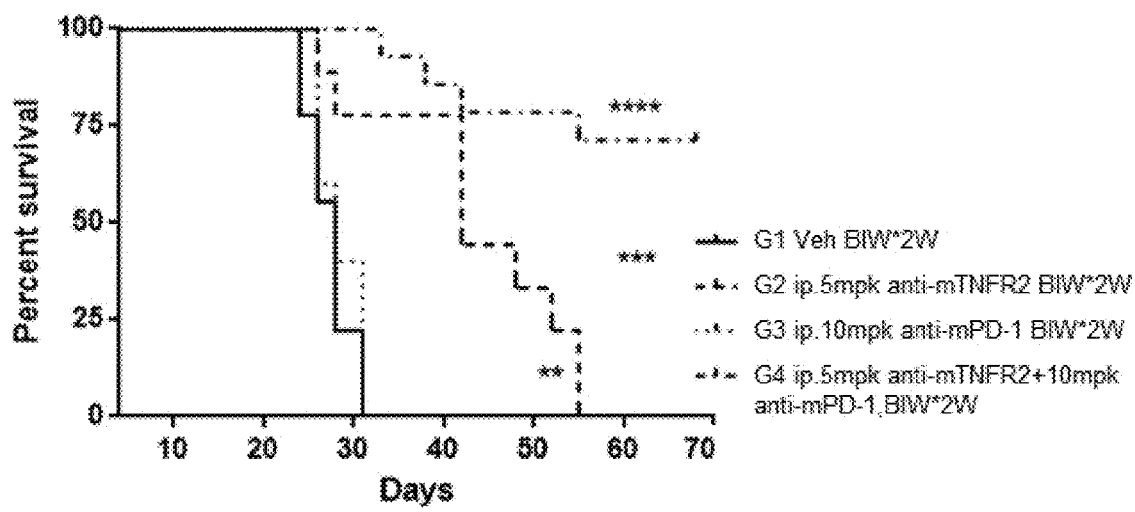

28 days after the last dose, all mice within the four groups were in the observation phase, and tumor volumes for each mice were recorded at least once a week. The tumor volume of the mice in the G2 anti-mTNFR2 group and the G3 anti-mPD-L1 group gradually grow and the mice in the two groups eventually died on day 55, while some mice in the G4 combination treatment group were still alive on day 68, and the survival rate of this group was higher than 50% (55.6%). 3 mice in the G4 combination treatment group demonstreated complete tumor regression until the end of the experiment which is significant better compared to the single drug treated groups and the control group (p<0.001, p<0.0001) indicating better efficacy of the combination treatment compared to either of the single drug treatment (FIG. 14C).

The invention claimed is:

1. An antibody or antigen binding fragment thereof which specifically binds to TNFR2, comprising:
   (i) heavy chain CDR combinations of CDR1-VH, CDR2-VH, and CDR3-VH, wherein CDR1-VH comprises the sequence of SEQ ID NO: 74, CDR2-VH comprises the sequence of SEQ ID NO: 75, and CDR3-VH comprises the sequence of SEQ ID NO: 76 by IMGT numbering; and
   light chain CDR combinations of CDR1-VL, CDR2-VL, and CDR3-VL, wherein CDR1-VL comprises the sequence of SEQ ID NO: 80, CDR2-VL comprises the sequence of SEQ ID NO: 81, and CDR3-VL comprises the sequence of SEQ ID NO: 82 by IMGT numbering; or
   (ii) heavy chain CDR combinations of CDR1-VH, CDR2-VH, and CDR3-VH, wherein CDR1-VH comprises the sequence of SEQ ID NO: 71, CDR2-VH comprises the sequence of SEQ ID NO: 72, and CDR3-VH comprises the sequence of SEQ ID NO: 73 by KABAT numbering; and
   light chain CDR combinations of CDR1-VL, CDR2-VL, and CDR3-VL, wherein CDR1-VL comprises the sequence of SEQ ID NO: 77, CDR2-VL comprises the sequence of SEQ ID NO: 78, and CDR3-VL comprises the sequence of SEQ ID NO: 79 by KABAT numbering.

2. The antibody or antigen binding fragment thereof of claim 1, comprising a heavy chain variable region and a light chain variable region having the sequence shown in SEQ ID NO: 9 and SEQ ID NO: 10, respectively.

3. The antibody or antigen-binding fragment thereof of claim 1, wherein the antibody or antigen-binding fragment comprises a chimeric antibody or a humanized antibody.

4. The antibody or antigen-binding fragment thereof of claim 1, comprising a constant region selected from the group consisting of human IgG1, IgG2, IgG3, IgG4, IgA, IgM, IgE and IgD, wherein the antibody or antigen-binding fragment:
   1) Specifically binds to cells that express TNFR2 on cell surface;
   2) specifically binds to Treg cells;
   3) inhibits the binding of TNFa to TNFR2 protein;
   4) inhibits the binding of TNFa to TNFR2 expressed on the cell surface;
   5) inhibits TNFa-mediated Treg proliferation and/or Treg function;
   6) Mediates ADCC function against TNFR2-expressing cell; or/and
   7) inhibits tumor growth.

5. The antibody or antigen-binding fragment thereof of claim 1, wherein the antigen-binding fragment is selected from the group consisting of F(ab)2, Fab', Fab, Fv, scFv, and bispecific antibodies.

6. A polynucleotide encoding the antibody or antigen-binding fragment thereof or any combination thereof as claimed in claim 1.

7. A pharmaceutical composition, comprising the antibody or antigen binding fragment thereof of claim 1, and a pharmaceutically acceptable carrier.

8. The pharmaceutical composition of claim 7, further comprising additional anti-tumor agents.

9. A method for lessening, delaying, or eliminating an immune abnormality-related disease, comprising administering to a subject in need the antibody or antigen binding fragment thereof of claim 1, wherein the immune abnormality-related disease is a TNFR2-related tumor.

10. The method of claim 9, further comprising administering to the subject an additional anti-tumor therapy, wherein the additional anti-tumor therapy is an anti-PD-1 antibody.

11. The method of claim 9, wherein the TNFR2-related tumor is selected from the group consisting of:
   1) ovarian cancer, advanced epidermal T cell lymphoma, stage III/IV metastatic colorectal cancer, triple negative breast cancer and/or pancreatic cancer; and
   2) advanced solid tumors resistant to CTLA-4 and PD-1 therapy.

12. A method for detecting soluble TNFR2 (sTNFR2), comprising contacting a sample suspected of containing sTNFR2 with the antibody or antigen binding fragment thereof of claim 1.

* * * * *

```
SEQUENCE LISTING

<160> NUMBER OF SEQ ID NOS: 154

<210> SEQ ID NO 1
<211> LENGTH: 121
<212> TYPE: PRT
<213> ORGANISM: Artificial Sequence
<220> FEATURE:
<223> OTHER INFORMATION: Positive candidate Clone ID 1 VH

<400> SEQUENCE: 1

Glu Val Gln Leu Gln Glu Ser Gly Gly Gly Leu Val Gln Pro Gly Gly
1               5                   10                  15

Ser Leu Asn Leu Ser Cys Ala Ala Ser Gly Phe Ala Phe Ser Thr Tyr
            20                  25                  30

Asp Leu Ser Trp Val Arg Gln Thr Pro Glu Lys Arg Leu Glu Trp Val
        35                  40                  45

Ala Tyr Ile Asn Asn Gly Gly Ile Ser Thr Tyr Tyr Ser Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Val Arg Gly Pro Phe Tyr Gly Ser Ala Asn Tyr Phe Asp Tyr Trp Gly
            100                 105                 110

Gln Gly Thr Thr Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: Positive candidate Clone ID 1 VL

<400> SEQUENCE: 2

Glu Ile Val Met Thr Gln Ser Pro Ala Ser Leu Ser Leu Ser Val Gly
1               5                   10                  15

Glu Thr Val Thr Ile Thr Cys Arg Thr Ser Glu Ser Ile Tyr Ser Asn
            20                  25                  30

Leu Pro Trp Tyr Gln Gln Lys Gln Gly Lys Ser Pro Gln Leu Leu Val
        35                  40                  45

Tyr Asp Ala Thr Lys Leu Ala Glu Gly Val Pro Ser Arg Phe Ser Gly
    50                  55                  60

Ser Glu Ser Gly Thr Gln Tyr Ser Leu Lys Ile Asn Ser Leu Gln Ser
65                  70                  75                  80

Glu Asp Phe Gly Tyr Tyr Cys Gln His Phe Trp Val Thr Pro Trp
                85                  90                  95
```

Thr Phe Gly Gly Gly Thr Lys Leu Glu Ile Lys
            100                 105

<210> SEQ ID NO 3
<211> LENGTH: 121
<212> TYPE: PRT
<213> ORGANISM: Artificial Sequence
<220> FEATURE:
<223> OTHER INFORMATION: Positive candidate Clone ID 88 VH

<400> SEQUENCE: 3

Glu Val Gln Leu Gln Glu Ser Gly Gly Gly Leu Val Gln Pro Gly Gly
1               5                   10                  15

Ser Leu Asn Leu Ser Cys Ala Ala Ser Gly Phe Ala Phe Ser Thr Tyr
            20                  25                  30

Asp Leu Ser Trp Val Arg Gln Thr Pro Gly Lys Arg Leu Glu Trp Val
        35                  40                  45

Ala Tyr Ile Asn Asn Gly Gly Ile Ser Thr Tyr Tyr Ser Asp Thr Val
    50                  55                  60

Lys Gly Arg Phe Thr Ile Thr Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Val Arg Gly Pro Phe Tyr Gly Ser Ala Asn Tyr Phe Asp Tyr Trp Gly
            100                 105                 110

Gln Gly Thr Thr Val Thr Val Ser Ser
        115                 120

<210> SEQ ID NO 4
<211> LENGTH: 107
<212> TYPE: PRT
<213> ORGANISM: Artificial Sequence
<220> FEATURE:
<223> OTHER INFORMATION: Positive candidate Clone ID 88 VL

<400> SEQUENCE: 4

Asp Ile Leu Met Thr Gln Ser Pro Ala Ser Leu Ser Leu Phe Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Asp Ala Thr Lys Leu Ala Glu Gly Val Pro Ser Arg Phe Ser Gly
    50                  55                  60

Ser Glu Ser Gly Thr Gln Tyr Ser Leu Lys Ile Asn Ser Leu Gln Ser
65                  70                  75                  80

Glu Asp Phe Gly Thr Tyr Tyr Cys Gln His Phe Trp Val Thr Pro Trp
                85                  90                  95

Thr Phe Gly Gly Gly Thr Lys Leu Glu Ile Lys
            100                 105

<210> SEQ ID NO 5
<211> LENGTH: 121
<212> TYPE: PRT
<213> ORGANISM: Artificial Sequence
<220> FEATURE:
<223> OTHER INFORMATION: Positive candidate Clone ID 125 VH

<400> SEQUENCE: 5

Glu Val Gln Leu Gln Glu Ser Gly Gly Gly Leu Val Gln Pro Gly Gly

```
              1               5                  10                  15
            Ser Leu Asn Leu Ser Cys Ala Ala Ser Gly Phe Ala Phe Ser Ile Tyr
                            20                  25                  30

Asp Leu Ser Trp Val Arg Gln Thr Pro Glu Lys Arg Leu Glu Trp Val
                            35                  40                  45

Ala Tyr Ile Asn Asn Gly Gly Ile Ser Thr Tyr Tyr Ser Asp Thr Val
                            50                  55                  60

Lys Gly Arg Phe Thr Ile Ser Arg Asp Asn Ala Lys Asn Thr Leu Tyr
             65                 70                  75                  80

Leu Gln Met Ser Ser Leu Lys Ser Glu Asp Thr Ala Met Tyr Tyr Cys
                            85                  90                  95

Val Arg Gly Pro Phe Tyr Gly Ser Ala Asn Tyr Phe Asp Tyr Trp Gly
                            100                 105                 110

Gln Gly Thr Thr Val Thr Val Ser Ser
                            115                 120
```

<210> SEQ ID NO 6
<211> LENGTH: 107
<212> TYPE: PRT
<213> ORGANISM: Artificial Sequence
<220> FEATURE:
<223> OTHER INFORMATION: Positive candidate Clone ID 125 VL

<400> SEQUENCE: 6

```
            Asp Ile Gln Met Thr Gln Ser Pro Ala Ser Leu Ser Leu Ser Val Gly
             1              5                  10                  15

Glu Thr Val Thr Ile Thr Cys Arg Ala Ser Glu Asn Ile Tyr Ser Asn
                            20                  25                  30

Leu Ala Trp Tyr Gln Gln Lys Gln Gly Lys Ser Pro Gln Leu Leu Val
                            35                  40                  45

Tyr Asp Ala Thr Lys Leu Ala Glu Gly Val Pro Ser Arg Phe Ser Gly
                            50                  55                  60

Ser Glu Ser Gly Thr Gln Tyr Ser Leu Lys Ile Asn Ser Leu Gln Ser
             65                 70                  75                  80

Glu Asp Phe Gly Thr Tyr Tyr Cys Gln His Phe Trp Val Thr Pro Trp
                            85                  90                  95

Thr Phe Gly Gly Gly Thr Lys Leu Glu Ile Lys
                            100                 105
```

<210> SEQ ID NO 7
<211> LENGTH: 119
<212> TYPE: PRT
<213> ORGANISM: Artificial Sequence
<220> FEATURE:
<223> OTHER INFORMATION: Positive candidate Clone ID 133 VH

<400> SEQUENCE: 7

```
            Glu Val Gln Leu Gln Glu Ser Gly Ala Glu Leu Val Arg Ser Gly Ala
             1              5                  10                  15

Ser Val Lys Leu Ser Cys Thr Ala Ser Gly Phe Asn Ile Lys Asp Tyr
                            20                  25                  30

Tyr Ile Gln Trp Val Lys Gln Arg Pro Glu Gln Gly Leu Glu Trp Ile
                            35                  40                  45

Gly Trp Ile Asp Pro Glu Ser Gly Asn Thr Lys Tyr Ala Pro Lys Phe
                            50                  55                  60

Gln Asp Lys Ala Thr Met Thr Ala Asp Thr Ser Ser Asn Thr Ala Tyr
             65                 70                  75                  80
```

```
Leu Gln Leu Ser Gly Leu Thr Ser Glu Asp Ser Ala Val Tyr Tyr Cys
                85                  90                  95

Asn Ala Tyr Tyr Asp Tyr Asp Gly Ser Met Asp Tyr Trp Gly Gln Gly
            100                 105                 110

Thr Thr Val Thr Val Ser Ser
        115

<210> SEQ ID NO 8
<211> LENGTH: 113
<212> TYPE: PRT
<213> ORGANISM: Artificial Sequence
<220> FEATURE:
<223> OTHER INFORMATION: Positive candidate Clone ID 133 VL

<400> SEQUENCE: 8

Asp Ile Val Met Thr Gln Ser Pro Leu Ser Leu Pro Val Ser Leu Gly
1               5                   10                  15

Asp Gln Ala Ser Ile Ser Cys Arg Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Asp Asp Leu Gly Val Tyr Phe Cys Ser Gln Ser
                85                  90                  95

Thr His Val Pro Thr Trp Thr Phe Gly Gly Gly Thr Lys Leu Glu Ile
            100                 105                 110

Lys

<210> SEQ ID NO 9
<211> LENGTH: 123
<212> TYPE: PRT
<213> ORGANISM: Artificial Sequence
<220> FEATURE:
<223> OTHER INFORMATION: Positive candidate Clone ID 219 VH

<400> SEQUENCE: 9

Glu Val Gln Leu Gln Glu Ser Gly Ala Glu Leu Val Arg Pro Gly Ala
1               5                   10                  15

Ser Val Lys Leu Ser Cys Lys Ala Ser Gly Tyr Ser Phe Thr Asn Tyr
            20                  25                  30

Trp Met Asn Trp Val Lys Gln Arg Pro Gly Gln Gly Leu Glu Trp Ile
        35                  40                  45

Gly Met Ile His Pro Ser Asp Thr Glu Thr Arg Leu Asn Gln Asn Phe
    50                  55                  60

Lys Asp Lys Ala Thr Leu Thr Val Asp Lys Ser Ser Ser Thr Ser Tyr
65                  70                  75                  80

Met Gln Leu Ser Ser Pro Thr Ser Glu Asp Ser Ala Val Tyr Tyr Cys
                85                  90                  95

Ala Arg Gly Glu Gly Leu Gly Ala Ala Arg Ser Val Ser Met Asp Tyr
            100                 105                 110

Trp Gly Gln Gly Thr Thr Val Thr Val Ser Ser
        115                 120

<210> SEQ ID NO 10
<211> LENGTH: 107
```

```
<212> TYPE: PRT
<213> ORGANISM: Artificial Sequence
<220> FEATURE:
<223> OTHER INFORMATION: Positive candidate Clone ID 219 VL

<400> SEQUENCE: 10

Asp Ile Leu Met Thr Gln Ser Pro Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Val Leu Ile
        35                  40                  45

Tyr Tyr Thr Ala Ile Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 11
<211> LENGTH: 120
<212> TYPE: PRT
<213> ORGANISM: Artificial Sequence
<220> FEATURE:
<223> OTHER INFORMATION: Positive candidate Clone ID 224 VH

<400> SEQUENCE: 11

Glu Val Gln Leu Gln Glu Ser Gly Pro Glu Ile Val Lys Pro Gly Ala
1               5                   10                  15

Ser Val Lys Leu Ser Cys Thr Ala Ser Gly Phe Asn Asn Lys Asp Ile
            20                  25                  30

Tyr Met His Trp Val Lys Gln Arg Pro Glu Gln Gly Leu Glu Trp Ile
        35                  40                  45

Gly Arg Ile Asp Pro Ala Thr Gly Asn Thr Lys His Asp Pro Lys Phe
50                  55                  60

Gln Asp Lys Ala Thr Leu Ser Ser Asp Thr Ser Ser Asn Thr Ala Tyr
65                  70                  75                  80

Leu Gln Phe Ser Ser Leu Thr Ser Glu Asp Thr Ala Val Tyr Tyr Cys
                85                  90                  95

Ala His Ser Pro Tyr Gly Asp Phe Gly Ala Met Asp Tyr Trp Gly Gln
            100                 105                 110

Gly Thr Thr Val Thr Val Ser Ser
        115                 120

<210> SEQ ID NO 12
<211> LENGTH: 108
<212> TYPE: PRT
<213> ORGANISM: Artificial Sequence
<220> FEATURE:
<223> OTHER INFORMATION: Positive candidate Clone ID 224 VL

<400> SEQUENCE: 12

Asp Ile Gln Met Thr Gln Ser Pro Ala Ile Met Ser Ala Ser Leu Gly
1               5                   10                  15

Glu Arg Val Thr Met Thr Cys Thr Ala Ser Ser Ser Val Ser Ser Asn
            20                  25                  30

Tyr Leu His Trp Tyr Gln Gln Lys Pro Gly Ser Ser Pro Lys Leu Trp
```

```
              35                  40                  45

Ile Tyr Ser Thr Ser Asn Leu Pro Ser Gly Val Pro Ala Arg Phe Ser
         50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys His Gln Tyr His Arg Ser Pro
                 85                  90                  95

Trp Thr Phe Gly Gly Gly Thr Lys Leu Glu Ile Lys
            100                 105

<210> SEQ ID NO 13
<211> LENGTH: 123
<212> TYPE: PRT
<213> ORGANISM: Artificial Sequence
<220> FEATURE:
<223> OTHER INFORMATION: Positive candidate Clone ID 226 VH

<400> SEQUENCE: 13

Glu Val Gln Leu Gln Glu Ser Gly Ala Glu Leu Val Arg Pro Gly Ala
 1               5                  10                  15

Ser Val Lys Leu Ser Cys Lys Ala Ser Gly Tyr Ser Phe Thr Asn Tyr
                 20                  25                  30

Trp Met Asn Trp Val Lys Gln Arg Pro Gly Gln Gly Leu Glu Trp Ile
             35                  40                  45

Gly Met Ile His Pro Ser Asp Ser Glu Thr Arg Leu Asn Gln Lys Phe
         50                  55                  60

Lys Asp Lys Ala Thr Leu Thr Val Asp Lys Ser Ser Ser Thr Ala Tyr
 65                  70                  75                  80

Met Gln Leu Ser Ser Pro Thr Ser Glu Asp Ser Ala Val Tyr Tyr Cys
                 85                  90                  95

Ala Arg Gly Glu Gly Leu Gly Ala Ala Arg Ser Val Ser Met Asp Tyr
            100                 105                 110

Trp Gly Gln Gly Thr Thr Val Thr Val Ser Ser
        115                 120

<210> SEQ ID NO 14
<211> LENGTH: 107
<212> TYPE: PRT
<213> ORGANISM: Artificial Sequence
<220> FEATURE:
<223> OTHER INFORMATION: Positive candidate Clone ID 226 VL

<400> SEQUENCE: 14

Asp Ile Gln Met Thr Gln Ser Pro Ser Ser Leu Ser Ala Ser Leu Gly
 1               5                  10                  15

Asp Arg Val Thr Ile Ser Cys Arg Ala Ser Gln Asp Ile Ser Asn Tyr
                 20                  25                  30

Leu Asn Trp Tyr Gln Gln Lys Pro Asp Gly Thr Val Lys Val Leu Ile
             35                  40                  45

Tyr Tyr Thr Ala Leu Leu His Ser Gly Val Pro Ser Arg Phe Ser Gly
         50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Trp
                 85                  90                  95

Thr Phe Gly Gly Gly Thr Lys Leu Glu Ile Lys
            100                 105
```

<210> SEQ ID NO 15
<211> LENGTH: 120
<212> TYPE: PRT
<213> ORGANISM: Artificial Sequence
<220> FEATURE:
<223> OTHER INFORMATION: Positive candidate Clone ID 309 VH

<400> SEQUENCE: 15

Glu Val Gln Leu Gln Glu Ser Gly Ala Glu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile His Trp Val Lys Leu Arg Pro Gly Gln Gly Phe Glu Trp Ile
        35                  40                  45

Gly Glu Ile Asn Pro Asn Asn Gly Gly Thr Asp Tyr Asn Glu Lys Phe
    50                  55                  60

Lys Arg Lys Ala Thr Leu Thr Val Asp Lys Ser Ser Thr Ala Tyr
65                  70                  75                  80

Met Glu Leu Ser Ser Leu Thr Ser Glu Asp Ser Ala Ile Tyr Tyr Cys
                85                  90                  95

Thr Ile Asp Ser Met Ile Thr Thr Trp Phe Ala Tyr Trp Gly Gln
            100                 105                 110

Gly Thr Thr Val Thr Val Ser Ser
        115                 120

<210> SEQ ID NO 16
<211> LENGTH: 107
<212> TYPE: PRT
<213> ORGANISM: Artificial Sequence
<220> FEATURE:
<223> OTHER INFORMATION: Positive candidate Clone ID 309 VL

<400> SEQUENCE: 16

Glu Ile Val Met Thr Gln Ser Gln Lys Leu Met Ser Thr Val Val Gly
1               5                   10                  15

Asp Arg Val Ser Val Thr Cys Lys Ala Ser Gln Asn Val Gly Thr Asn
            20                  25                  30

Val Ala Trp Phe Gln Gln Lys Pro Gly Gln Ser Pro Lys Ala Leu Ile
        35                  40                  45

Asn Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Ser Val Gln Ser
65                  70                  75                  80

Glu Asp Leu Ala Glu Tyr Phe Cys Gln Gln Tyr Asn Ser Tyr Pro Phe
                85                  90                  95

Thr Phe Gly Ser Gly Thr Lys Leu Glu Ile Lys
            100                 105

<210> SEQ ID NO 17
<211> LENGTH: 119
<212> TYPE: PRT
<213> ORGANISM: Artificial Sequence
<220> FEATURE:
<223> OTHER INFORMATION: Positive candidate Clone ID 352 VH

<400> SEQUENCE: 17

Glu Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr

```
                    20                  25                  30
Gly Val His Trp Val Arg Gln Pro Pro Gly Lys Gly Leu Glu Trp Leu
            35                  40                  45

Val Val Ile Trp Ser Asp Gly Thr Thr Tyr Asn Ser Ala Leu Lys
 50                  55                  60

Ser Arg Leu Ser Ile Ser Lys Asp Asn Ser Lys Ser Gln Val Phe Leu
 65                  70                  75                  80

Lys Met Asn Ser Leu Gln Thr Asp Asp Thr Ala Met Tyr Tyr Cys Ala
                85                  90                  95

Arg His Asp Asp Asp Gly Tyr Tyr Ala Met Asp Tyr Trp Gly Gln Gly
                100                 105                 110

Thr Thr Val Thr Val Ser Ser
            115

<210> SEQ ID NO 18
<211> LENGTH: 106
<212> TYPE: PRT
<213> ORGANISM: Artificial Sequence
<220> FEATURE:
<223> OTHER INFORMATION: Positive candidate Clone ID 352 VL

<400> SEQUENCE: 18

Asp Ile Val Leu Thr Gln Ser Pro Ser Leu Met Ser Ala Ser Pro Gly
 1               5                  10                  15

Glu Lys Val Thr Met Thr Cys Ser Ala Ser Ser Ser Val Gly Tyr Met
                20                  25                  30

Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Ala Arg Phe Ser Gly Ser
 50                  55                  60

Gly Ser Gly Thr Ser Tyr Ser Leu Thr Ile Ser Ser Met Glu Val Glu
 65                  70                  75                  80

Asp Ala Ala Thr Tyr Tyr Cys Gln Gln Trp Ser Asp Pro Phe Thr
                85                  90                  95

Phe Gly Ser Gly Thr Lys Leu Glu Ile Lys
            100                 105

<210> SEQ ID NO 19
<211> LENGTH: 119
<212> TYPE: PRT
<213> ORGANISM: Artificial Sequence
<220> FEATURE:
<223> OTHER INFORMATION: Positive candidate Clone ID 365 VH

<400> SEQUENCE: 19

Glu Val Gln Leu Gln Glu Ser Gly Pro Gly Leu Val Gln Pro Ser Gln
 1               5                  10                  15

Ser Leu Ser Ile Thr Cys Thr Val Ser Gly Phe Ser Leu Thr Ser Tyr
                20                  25                  30

Gly Val His Trp Val Arg Gln Ser Pro Gly Lys Gly Leu Glu Trp Leu
            35                  40                  45

Gly Leu Ile Trp Ser Asp Gly Ser Pro Asp Tyr Ser Ala Ala Phe Ile
 50                  55                  60

Ser Arg Leu Ser Ile Asn Lys Asp Asn Ser Lys Ser Gln Val Phe Phe
 65                  70                  75                  80

Lys Met Asn Ser Leu Gln Ala Asp Asp Thr Ala Ile Tyr Tyr Cys Ala
                85                  90                  95
```

-continued

Arg Asn Asp Asp Gly Gly Asp Tyr Val Met Asp Tyr Trp Gly Gln Gly
            100                 105                 110

Thr Thr Val Thr Val Ser Ser
        115

<210> SEQ ID NO 20
<211> LENGTH: 106
<212> TYPE: PRT
<213> ORGANISM: Artificial Sequence
<220> FEATURE:
<223> OTHER INFORMATION: Positive candidate Clone ID 365 VL

<400> SEQUENCE: 20

Glu Ile Val Leu Thr Gln Ser Pro Ala Leu Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Thr Ser Asn Pro Leu Thr
                85                  90                  95

Phe Gly Ala Gly Thr Lys Leu Glu Ile Lys
            100                 105

<210> SEQ ID NO 21
<211> LENGTH: 119
<212> TYPE: PRT
<213> ORGANISM: Artificial Sequence
<220> FEATURE:
<223> OTHER INFORMATION: Positive candidate Clone ID 395 VH

<400> SEQUENCE: 21

Glu Val Gln Leu Gln Glu Ser Gly Pro Val Leu Val Gln Pro Ser Gln
1               5                   10                  15

Ser Leu Ser Ile Thr Cys Thr Val Ser Gly Phe Ser Leu Thr Ser Tyr
            20                  25                  30

Ser Val His Trp Val Arg Gln Ser Pro Gly Lys Gly Leu Glu Trp Leu
        35                  40                  45

Gly Val Ile Trp Ser Asp Gly Thr Asp Tyr Ser Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Thr Ala Ile Tyr Tyr Cys Ala
                85                  90                  95

Arg Asn Asp Asp Gly Gly Asp Tyr Ala Met Asp Tyr Trp Gly Gln Gly
            100                 105                 110

Thr Thr Val Thr Val Ser Ser
        115

<210> SEQ ID NO 22
<211> LENGTH: 106
<212> TYPE: PRT
<213> ORGANISM: Artificial Sequence
<220> FEATURE:
<223> OTHER INFORMATION: Positive candidate Clone ID 395 VL

```
<400> SEQUENCE: 22

Glu Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Ile Lys
            100                 105

<210> SEQ ID NO 23
<211> LENGTH: 5
<212> TYPE: PRT
<213> ORGANISM: Artificial Sequence
<220> FEATURE:
<223> OTHER INFORMATION: Positive candidate Clone ID 1 CDR1-VH analysed
      by KABAT

<400> SEQUENCE: 23

Thr Tyr Asp Leu Ser
1               5

<210> SEQ ID NO 24
<211> LENGTH: 17
<212> TYPE: PRT
<213> ORGANISM: Artificial Sequence
<220> FEATURE:
<223> OTHER INFORMATION: Positive candidate Clone ID 1 CDR2-VH analysed
      by KABAT

<400> SEQUENCE: 24

Tyr Ile Asn Asn Gly Gly Ile Ser Thr Tyr Tyr Ser Asp Thr Val Lys
1               5                   10                  15

Gly

<210> SEQ ID NO 25
<211> LENGTH: 12
<212> TYPE: PRT
<213> ORGANISM: Artificial Sequence
<220> FEATURE:
<223> OTHER INFORMATION: Positive candidate Clone ID 1 CDR3-VH analysed
      by KABAT

<400> SEQUENCE: 25

Gly Pro Phe Tyr Gly Ser Ala Asn Tyr Phe Asp Tyr
1               5                   10

<210> SEQ ID NO 26
<211> LENGTH: 8
<212> TYPE: PRT
<213> ORGANISM: Artificial Sequence
<220> FEATURE:
<223> OTHER INFORMATION: Positive candidate Clone ID 1 CDR1-VH analysed
      by IMGT

<400> SEQUENCE: 26

Gly Phe Ala Phe Ser Thr Tyr Asp
```

```
<210> SEQ ID NO 27
<211> LENGTH: 8
<212> TYPE: PRT
<213> ORGANISM: Artificial Sequence
<220> FEATURE:
<223> OTHER INFORMATION: Positive candidate Clone ID 1 CDR2-VH analysed
      by IMGT

<400> SEQUENCE: 27

Ile Asn Asn Gly Gly Ile Ser Thr
1               5

<210> SEQ ID NO 28
<211> LENGTH: 14
<212> TYPE: PRT
<213> ORGANISM: Artificial Sequence
<220> FEATURE:
<223> OTHER INFORMATION: Positive candidate Clone ID 1 CDR3-VH analysed
      by IMGT

<400> SEQUENCE: 28

Val Arg Gly Pro Phe Tyr Gly Ser Ala Asn Tyr Phe Asp Tyr
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Positive candidate Clone ID 1 CDR1-VL analysed
      by KABAT

<400> SEQUENCE: 29

Arg Thr Ser Glu Ser Ile Tyr Ser Asn Leu Pro
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Positive candidate Clone ID 1 CDR2-VL analysed
      by KABAT

<400> SEQUENCE: 30

Asp Ala Thr Lys Leu Ala Glu
1               5

<210> SEQ ID NO 31
<211> LENGTH: 9
<212> TYPE: PRT
<213> ORGANISM: Artificial Sequence
<220> FEATURE:
<223> OTHER INFORMATION: Positive candidate Clone ID 1 CDR3-VL analysed
      by KABAT

<400> SEQUENCE: 31

Gln His Phe Trp Val Thr Pro Trp Thr
1               5

<210> SEQ ID NO 32
<211> LENGTH: 6
<212> TYPE: PRT
<213> ORGANISM: Artificial Sequence
<220> FEATURE:
<223> OTHER INFORMATION: Positive candidate Clone ID 1 CDR1-VL analysed
``` by IMGT

<400> SEQUENCE: 32

Glu Ser Ile Tyr Ser Asn
1               5

<210> SEQ ID NO 33
<211> LENGTH: 3
<212> TYPE: PRT
<213> ORGANISM: Artificial Sequence
<220> FEATURE:
<223> OTHER INFORMATION: Positive candidate Clone ID 1 CDR2-VL analysed
      by IMGT

<400> SEQUENCE: 33

Asp Ala Thr
1

<210> SEQ ID NO 34
<211> LENGTH: 9
<212> TYPE: PRT
<213> ORGANISM: Artificial Sequence
<220> FEATURE:
<223> OTHER INFORMATION: Positive candidate Clone ID 1 CDR3-VL analysed
      by IMGT

<400> SEQUENCE: 34

Gln His Phe Trp Val Thr Pro Trp Thr
1               5

<210> SEQ ID NO 35
<211> LENGTH: 5
<212> TYPE: PRT
<213> ORGANISM: Artificial Sequence
<220> FEATURE:
<223> OTHER INFORMATION: Positive candidate Clone ID 88 CDR1-VH analysed
      by KABAT

<400> SEQUENCE: 35

Thr Tyr Asp Leu Ser
1               5

<210> SEQ ID NO 36
<211> LENGTH: 17
<212> TYPE: PRT
<213> ORGANISM: Artificial Sequence
<220> FEATURE:
<223> OTHER INFORMATION: Positive candidate Clone ID 88 CDR2-VH analysed
      by KABAT

<400> SEQUENCE: 36

Tyr Ile Asn Asn Gly Gly Ile Ser Thr Tyr Tyr Ser Asp Thr Val Lys
1               5                   10                  15

Gly

<210> SEQ ID NO 37
<211> LENGTH: 12
<212> TYPE: PRT
<213> ORGANISM: Artificial Sequence
<220> FEATURE:
<223> OTHER INFORMATION: Positive candidate Clone ID 88 CDR3-VH analysed
      by KABAT

<400> SEQUENCE: 37

Gly Pro Phe Tyr Gly Ser Ala Asn Tyr Phe Asp Tyr
1               5                   10

<210> SEQ ID NO 38
<211> LENGTH: 8
<212> TYPE: PRT
<213> ORGANISM: Artificial Sequence
<220> FEATURE:
<223> OTHER INFORMATION: Positive candidate Clone ID 88 CDR1-VH analysed
      by IMGT

<400> SEQUENCE: 38

Gly Phe Ala Phe Ser Thr Tyr Asp
1               5

<210> SEQ ID NO 39
<211> LENGTH: 8
<212> TYPE: PRT
<213> ORGANISM: Artificial Sequence
<220> FEATURE:
<223> OTHER INFORMATION: Positive candidate Clone ID 88 CDR2-VH analysed
      by IMGT

<400> SEQUENCE: 39

Ile Asn Asn Gly Gly Ile Ser Thr
1               5

<210> SEQ ID NO 40
<211> LENGTH: 14
<212> TYPE: PRT
<213> ORGANISM: Artificial Sequence
<220> FEATURE:
<223> OTHER INFORMATION: Positive candidate Clone ID 88 CDR3-VH analysed
      by IMGT

<400> SEQUENCE: 40

Val Arg Gly Pro Phe Tyr Gly Ser Ala Asn Tyr Phe Asp Tyr
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Positive candidate Clone ID 88 CDR1-VL analysed
      by KABAT

<400> SEQUENCE: 41

Arg Ala Ser Glu Asn Ile Tyr Ser Asn Leu Ala
1               5                   10

<210> SEQ ID NO 42
<211> LENGTH: 7
<212> TYPE: PRT
<213> ORGANISM: Artificial Sequence
<220> FEATURE:
<223> OTHER INFORMATION: Positive candidate Clone ID 88 CDR2-VL analysed
      by KABAT

<400> SEQUENCE: 42

Asp Ala Thr Lys Leu Ala Glu
1               5

<210> SEQ ID NO 43
<211> LENGTH: 9
<212> TYPE: PRT
<213> ORGANISM: Artificial Sequence
<220> FEATURE:
<223> OTHER INFORMATION: Positive candidate Clone ID 88 CDR3-VL analysed
      by KABAT

```
<400> SEQUENCE: 43

Gln His Phe Trp Val Thr Pro Trp Thr
1               5

<210> SEQ ID NO 44
<211> LENGTH: 6
<212> TYPE: PRT
<213> ORGANISM: Artificial Sequence
<220> FEATURE:
<223> OTHER INFORMATION: Positive candidate Clone ID 88 CDR1-VL analysed
      by IMGT

<400> SEQUENCE: 44

Glu Asn Ile Tyr Ser Asn
1               5

<210> SEQ ID NO 45
<211> LENGTH: 3
<212> TYPE: PRT
<213> ORGANISM: Artificial Sequence
<220> FEATURE:
<223> OTHER INFORMATION: Positive candidate Clone ID 88 CDR2-VL analysed
      by IMGT

<400> SEQUENCE: 45

Asp Ala Thr
1

<210> SEQ ID NO 46
<211> LENGTH: 9
<212> TYPE: PRT
<213> ORGANISM: Artificial Sequence
<220> FEATURE:
<223> OTHER INFORMATION: Positive candidate Clone ID 88 CDR3-VL analysed
      by IMGT

<400> SEQUENCE: 46

Gln His Phe Trp Val Thr Pro Trp Thr
1               5

<210> SEQ ID NO 47
<211> LENGTH: 5
<212> TYPE: PRT
<213> ORGANISM: Artificial Sequence
<220> FEATURE:
<223> OTHER INFORMATION: Positive candidate Clone ID 125 CDR1-VH
      analysed by KABAT

<400> SEQUENCE: 47

Ile Tyr Asp Leu Ser
1               5

<210> SEQ ID NO 48
<211> LENGTH: 17
<212> TYPE: PRT
<213> ORGANISM: Artificial Sequence
<220> FEATURE:
<223> OTHER INFORMATION: Positive candidate Clone ID 125 CDR2-VH
      analysed by KABAT

<400> SEQUENCE: 48

Tyr Ile Asn Asn Gly Gly Ile Ser Thr Tyr Tyr Ser Asp Thr Val Lys
1               5                   10                  15

Gly

<210> SEQ ID NO 49
```

```
<211> LENGTH: 12
<212> TYPE: PRT
<213> ORGANISM: Artificial Sequence
<220> FEATURE:
<223> OTHER INFORMATION: Positive candidate Clone ID 125 CDR3-VH
      analysed by KABAT

<400> SEQUENCE: 49

Gly Pro Phe Tyr Gly Ser Ala Asn Tyr Phe Asp Tyr
1               5                   10

<210> SEQ ID NO 50
<211> LENGTH: 8
<212> TYPE: PRT
<213> ORGANISM: Artificial Sequence
<220> FEATURE:
<223> OTHER INFORMATION: Positive candidate Clone ID 125 CDR1-VH
      analysed by IMGT

<400> SEQUENCE: 50

Gly Phe Ala Phe Ser Ile Tyr Asp
1               5

<210> SEQ ID NO 51
<211> LENGTH: 8
<212> TYPE: PRT
<213> ORGANISM: Artificial Sequence
<220> FEATURE:
<223> OTHER INFORMATION: Positive candidate Clone ID 125 CDR2-VH
      analysed by IMGT

<400> SEQUENCE: 51

Ile Asn Asn Gly Gly Ile Ser Thr
1               5

<210> SEQ ID NO 52
<211> LENGTH: 14
<212> TYPE: PRT
<213> ORGANISM: Artificial Sequence
<220> FEATURE:
<223> OTHER INFORMATION: Positive candidate Clone ID 125 CDR3-VH
      analysed by IMGT

<400> SEQUENCE: 52

Val Arg Gly Pro Phe Tyr Gly Ser Ala Asn Tyr Phe Asp Tyr
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Positive candidate Clone ID 125 CDR1-VL
      analysed by KABAT

<400> SEQUENCE: 53

Arg Ala Ser Glu Asn Ile Tyr Ser Asn Leu Ala
1               5                   10

<210> SEQ ID NO 54
<211> LENGTH: 7
<212> TYPE: PRT
<213> ORGANISM: Artificial Sequence
<220> FEATURE:
<223> OTHER INFORMATION: Positive candidate Clone ID 125 CDR2-VL
      analysed by KABAT

<400> SEQUENCE: 54
```

Asp Ala Thr Lys Leu Ala Glu
1               5

<210> SEQ ID NO 55
<211> LENGTH: 9
<212> TYPE: PRT
<213> ORGANISM: Artificial Sequence
<220> FEATURE:
<223> OTHER INFORMATION: Positive candidate Clone ID 125 CDR3-VL
      analysed by KABAT

<400> SEQUENCE: 55

Gln His Phe Trp Val Thr Pro Trp Thr
1               5

<210> SEQ ID NO 56
<211> LENGTH: 6
<212> TYPE: PRT
<213> ORGANISM: Artificial Sequence
<220> FEATURE:
<223> OTHER INFORMATION: Positive candidate Clone ID 125 CDR1-VL
      analysed by IMGT

<400> SEQUENCE: 56

Glu Asn Ile Tyr Ser Asn
1               5

<210> SEQ ID NO 57
<211> LENGTH: 3
<212> TYPE: PRT
<213> ORGANISM: Artificial Sequence
<220> FEATURE:
<223> OTHER INFORMATION: Positive candidate Clone ID 125 CDR2-VL
      analysed by IMGT

<400> SEQUENCE: 57

Asp Ala Thr
1

<210> SEQ ID NO 58
<211> LENGTH: 9
<212> TYPE: PRT
<213> ORGANISM: Artificial Sequence
<220> FEATURE:
<223> OTHER INFORMATION: Positive candidate Clone ID 125 CDR3-VL
      analysed by IMGT

<400> SEQUENCE: 58

Gln His Phe Trp Val Thr Pro Trp Thr
1               5

<210> SEQ ID NO 59
<211> LENGTH: 5
<212> TYPE: PRT
<213> ORGANISM: Artificial Sequence
<220> FEATURE:
<223> OTHER INFORMATION: Positive candidate Clone ID 133 CDR1-VH
      analysed by KABAT

<400> SEQUENCE: 59

Asp Tyr Tyr Ile Gln
1               5

<210> SEQ ID NO 60
<211> LENGTH: 17
<212> TYPE: PRT
<213> ORGANISM: Artificial Sequence
<220> FEATURE:

```
<223> OTHER INFORMATION: Positive candidate Clone ID 133 CDR2-VH
      analysed by KABAT

<400> SEQUENCE: 60

Trp Ile Asp Pro Glu Ser Gly Asn Thr Lys Tyr Ala Pro Lys Phe Gln
1               5                   10                  15
Asp

<210> SEQ ID NO 61
<211> LENGTH: 10
<212> TYPE: PRT
<213> ORGANISM: Artificial Sequence
<220> FEATURE:
<223> OTHER INFORMATION: Positive candidate Clone ID 133 CDR3-VH
      analysed by KABAT

<400> SEQUENCE: 61

Tyr Tyr Asp Tyr Asp Gly Ser Met Asp Tyr
1               5                   10

<210> SEQ ID NO 62
<211> LENGTH: 8
<212> TYPE: PRT
<213> ORGANISM: Artificial Sequence
<220> FEATURE:
<223> OTHER INFORMATION: Positive candidate Clone ID 133 CDR1-VH
      analysed by IMGT

<400> SEQUENCE: 62

Gly Phe Asn Ile Lys Asp Tyr Tyr
1               5

<210> SEQ ID NO 63
<211> LENGTH: 8
<212> TYPE: PRT
<213> ORGANISM: Artificial Sequence
<220> FEATURE:
<223> OTHER INFORMATION: Positive candidate Clone ID 133 CDR2-VH
      analysed by IMGT

<400> SEQUENCE: 63

Ile Asp Pro Glu Ser Gly Asn Thr
1               5

<210> SEQ ID NO 64
<211> LENGTH: 12
<212> TYPE: PRT
<213> ORGANISM: Artificial Sequence
<220> FEATURE:
<223> OTHER INFORMATION: Positive candidate Clone ID 133 CDR3-VH
      analysed by IMGT

<400> SEQUENCE: 64

Asn Ala Tyr Tyr Asp Tyr Asp Gly Ser Met Asp Tyr
1               5                   10

<210> SEQ ID NO 65
<211> LENGTH: 16
<212> TYPE: PRT
<213> ORGANISM: Artificial Sequence
<220> FEATURE:
<223> OTHER INFORMATION: Positive candidate Clone ID 133 CDR1-VL
      analysed by KABAT

<400> SEQUENCE: 65

Arg Ser Ser Gln Ser Leu Val His Ser Asn Gly Asn Thr Tyr Leu His
1               5                   10                  15
```

<210> SEQ ID NO 66
<211> LENGTH: 7
<212> TYPE: PRT
<213> ORGANISM: Artificial Sequence
<220> FEATURE:
<223> OTHER INFORMATION: Positive candidate Clone ID 133 CDR2-VL
      analysed by KABAT

<400> SEQUENCE: 66

Lys Val Ser Asn Arg Phe Ser
1               5

<210> SEQ ID NO 67
<211> LENGTH: 10
<212> TYPE: PRT
<213> ORGANISM: Artificial Sequence
<220> FEATURE:
<223> OTHER INFORMATION: Positive candidate Clone ID 133 CDR3-VL
      analysed by KABAT

<400> SEQUENCE: 67

Ser Gln Ser Thr His Val Pro Thr Trp Thr
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Positive candidate Clone ID 133 CDR1-VL
      analysed by IMGT

<400> SEQUENCE: 68

Gln Ser Leu Val His Ser Asn Gly Asn Thr Tyr
1               5                   10

<210> SEQ ID NO 69
<211> LENGTH: 3
<212> TYPE: PRT
<213> ORGANISM: Artificial Sequence
<220> FEATURE:
<223> OTHER INFORMATION: Positive candidate Clone ID 133 CDR2-VL
      analysed by IMGT

<400> SEQUENCE: 69

Lys Val Ser
1

<210> SEQ ID NO 70
<211> LENGTH: 10
<212> TYPE: PRT
<213> ORGANISM: Artificial Sequence
<220> FEATURE:
<223> OTHER INFORMATION: Positive candidate Clone ID 133 CDR3-VL
      analysed by IMGT

<400> SEQUENCE: 70

Ser Gln Ser Thr His Val Pro Thr Trp Thr
1               5                   10

<210> SEQ ID NO 71
<211> LENGTH: 5
<212> TYPE: PRT
<213> ORGANISM: Artificial Sequence
<220> FEATURE:
<223> OTHER INFORMATION: Positive candidate Clone ID 219 CDR1-VH
      analysed by KABAT

<400> SEQUENCE: 71

Asn Tyr Trp Met Asn
1               5

<210> SEQ ID NO 72
<211> LENGTH: 17
<212> TYPE: PRT
<213> ORGANISM: Artificial Sequence
<220> FEATURE:
<223> OTHER INFORMATION: Positive candidate Clone ID 219 CDR2-VH
      analysed by KABAT

<400> SEQUENCE: 72

Met Ile His Pro Ser Asp Thr Glu Thr Arg Leu Asn Gln Asn Phe Lys
1               5                   10                  15

Asp

<210> SEQ ID NO 73
<211> LENGTH: 14
<212> TYPE: PRT
<213> ORGANISM: Artificial Sequence
<220> FEATURE:
<223> OTHER INFORMATION: Positive candidate Clone ID 219 CDR3-VH
      analysed by KABAT

<400> SEQUENCE: 73

Gly Glu Gly Leu Gly Ala Ala Arg Ser Val Ser Met Asp Tyr
1               5                   10

<210> SEQ ID NO 74
<211> LENGTH: 8
<212> TYPE: PRT
<213> ORGANISM: Artificial Sequence
<220> FEATURE:
<223> OTHER INFORMATION: Positive candidate Clone ID 219 CDR1-VH
      analysed by IMGT

<400> SEQUENCE: 74

Gly Tyr Ser Phe Thr Asn Tyr Trp
1               5

<210> SEQ ID NO 75
<211> LENGTH: 8
<212> TYPE: PRT
<213> ORGANISM: Artificial Sequence
<220> FEATURE:
<223> OTHER INFORMATION: Positive candidate Clone ID 219 CDR2-VH
      analysed by IMGT

<400> SEQUENCE: 75

Ile His Pro Ser Asp Thr Glu Thr
1               5

<210> SEQ ID NO 76
<211> LENGTH: 16
<212> TYPE: PRT
<213> ORGANISM: Artificial Sequence
<220> FEATURE:
<223> OTHER INFORMATION: Positive candidate Clone ID 219 CDR3-VH
      analysed by IMGT

<400> SEQUENCE: 76

Ala Arg Gly Glu Gly Leu Gly Ala Ala Arg Ser Val Ser Met Asp Tyr
1               5                   10                  15

```
<210> SEQ ID NO 77
<211> LENGTH: 11
<212> TYPE: PRT
<213> ORGANISM: Artificial Sequence
<220> FEATURE:
<223> OTHER INFORMATION: Positive candidate Clone ID 219 CDR1-VL
      analysed by KABAT

<400> SEQUENCE: 77

Arg Ala Ser Gln Asp Ile Ser Asn Tyr Leu Asn
1               5                   10

<210> SEQ ID NO 78
<211> LENGTH: 7
<212> TYPE: PRT
<213> ORGANISM: Artificial Sequence
<220> FEATURE:
<223> OTHER INFORMATION: Positive candidate Clone ID 219 CDR2-VL
      analysed by KABAT

<400> SEQUENCE: 78

Tyr Thr Ala Ile Leu His Ser
1               5

<210> SEQ ID NO 79
<211> LENGTH: 9
<212> TYPE: PRT
<213> ORGANISM: Artificial Sequence
<220> FEATURE:
<223> OTHER INFORMATION: Positive candidate Clone ID 219 CDR3-VL
      analysed by KABAT

<400> SEQUENCE: 79

Gln Gln Gly Asn Thr Leu Pro Trp Thr
1               5

<210> SEQ ID NO 80
<211> LENGTH: 6
<212> TYPE: PRT
<213> ORGANISM: Artificial Sequence
<220> FEATURE:
<223> OTHER INFORMATION: Positive candidate Clone ID 219 CDR1-VL
      analysed by IMGT

<400> SEQUENCE: 80

Gln Asp Ile Ser Asn Tyr
1               5

<210> SEQ ID NO 81
<211> LENGTH: 3
<212> TYPE: PRT
<213> ORGANISM: Artificial Sequence
<220> FEATURE:
<223> OTHER INFORMATION: Positive candidate Clone ID 219 CDR2-VL
      analysed by IMGT

<400> SEQUENCE: 81

Tyr Thr Ala
1

<210> SEQ ID NO 82
<211> LENGTH: 9
<212> TYPE: PRT
<213> ORGANISM: Artificial Sequence
<220> FEATURE:
<223> OTHER INFORMATION: Positive candidate Clone ID 219 CDR3-VL
      analysed by IMGT

<400> SEQUENCE: 82
```

```
Gln Gln Gly Asn Thr Leu Pro Trp Thr
1               5

<210> SEQ ID NO 83
<211> LENGTH: 5
<212> TYPE: PRT
<213> ORGANISM: Artificial Sequence
<220> FEATURE:
<223> OTHER INFORMATION: Positive candidate Clone ID 224 CDR1-VH
      analysed by KABAT

<400> SEQUENCE: 83

Asp Ile Tyr Met His
1               5

<210> SEQ ID NO 84
<211> LENGTH: 17
<212> TYPE: PRT
<213> ORGANISM: Artificial Sequence
<220> FEATURE:
<223> OTHER INFORMATION: Positive candidate Clone ID 224 CDR2-VH
      analysed by KABAT

<400> SEQUENCE: 84

Arg Ile Asp Pro Ala Thr Gly Asn Thr Lys His Asp Pro Lys Phe Gln
1               5                   10                  15
Asp

<210> SEQ ID NO 85
<211> LENGTH: 11
<212> TYPE: PRT
<213> ORGANISM: Artificial Sequence
<220> FEATURE:
<223> OTHER INFORMATION: Positive candidate Clone ID 224 CDR3-VH
      analysed by KABAT

<400> SEQUENCE: 85

Ser Pro Tyr Gly Asp Phe Gly Ala Met Asp Tyr
1               5                   10

<210> SEQ ID NO 86
<211> LENGTH: 8
<212> TYPE: PRT
<213> ORGANISM: Artificial Sequence
<220> FEATURE:
<223> OTHER INFORMATION: Positive candidate Clone ID 224 CDR1-VH
      analysed by IMGT

<400> SEQUENCE: 86

Gly Phe Asn Asn Lys Asp Ile Tyr
1               5

<210> SEQ ID NO 87
<211> LENGTH: 8
<212> TYPE: PRT
<213> ORGANISM: Artificial Sequence
<220> FEATURE:
<223> OTHER INFORMATION: Positive candidate Clone ID 224 CDR2-VH
      analysed by IMGT

<400> SEQUENCE: 87

Ile Asp Pro Ala Thr Gly Asn Thr
1               5

<210> SEQ ID NO 88
<211> LENGTH: 13
```

```
<212> TYPE: PRT
<213> ORGANISM: Artificial Sequence
<220> FEATURE:
<223> OTHER INFORMATION: Positive candidate Clone ID 224 CDR3-VH
      analysed by IMGT

<400> SEQUENCE: 88

Ala His Ser Pro Tyr Gly Asp Phe Gly Ala Met Asp Tyr
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Positive candidate Clone ID 224 CDR1-VL
      analysed by KABAT

<400> SEQUENCE: 89

Thr Ala Ser Ser Ser Val Ser Ser Asn Tyr Leu His
1               5                   10

<210> SEQ ID NO 90
<211> LENGTH: 7
<212> TYPE: PRT
<213> ORGANISM: Artificial Sequence
<220> FEATURE:
<223> OTHER INFORMATION: Positive candidate Clone ID 224 CDR2-VL
      analysed by KABAT

<400> SEQUENCE: 90

Ser Thr Ser Asn Leu Pro Ser
1               5

<210> SEQ ID NO 91
<211> LENGTH: 9
<212> TYPE: PRT
<213> ORGANISM: Artificial Sequence
<220> FEATURE:
<223> OTHER INFORMATION: Positive candidate Clone ID 224 CDR3-VL
      analysed by KABAT

<400> SEQUENCE: 91

His Gln Tyr His Arg Ser Pro Trp Thr
1               5

<210> SEQ ID NO 92
<211> LENGTH: 7
<212> TYPE: PRT
<213> ORGANISM: Artificial Sequence
<220> FEATURE:
<223> OTHER INFORMATION: Positive candidate Clone ID 224 CDR1-VL
      analysed by IMGT

<400> SEQUENCE: 92

Ser Ser Val Ser Ser Asn Tyr
1               5

<210> SEQ ID NO 93
<211> LENGTH: 3
<212> TYPE: PRT
<213> ORGANISM: Artificial Sequence
<220> FEATURE:
<223> OTHER INFORMATION: Positive candidate Clone ID 224 CDR2-VL
      analysed by IMGT

<400> SEQUENCE: 93

Ser Thr Ser
```

<210> SEQ ID NO 94
<211> LENGTH: 9
<212> TYPE: PRT
<213> ORGANISM: Artificial Sequence
<220> FEATURE:
<223> OTHER INFORMATION: Positive candidate Clone ID 224 CDR3-VL
      analysed by IMGT

<400> SEQUENCE: 94

His Gln Tyr His Arg Ser Pro Trp Thr
1               5

<210> SEQ ID NO 95
<211> LENGTH: 5
<212> TYPE: PRT
<213> ORGANISM: Artificial Sequence
<220> FEATURE:
<223> OTHER INFORMATION: Positive candidate Clone ID 226 CDR1-VH
      analysed by KABAT

<400> SEQUENCE: 95

Asn Tyr Trp Met Asn
1               5

<210> SEQ ID NO 96
<211> LENGTH: 17
<212> TYPE: PRT
<213> ORGANISM: Artificial Sequence
<220> FEATURE:
<223> OTHER INFORMATION: Positive candidate Clone ID 226 CDR2-VH
      analysed by KABAT

<400> SEQUENCE: 96

Met Ile His Pro Ser Asp Ser Glu Thr Arg Leu Asn Gln Lys Phe Lys
1               5                   10                  15

Asp

<210> SEQ ID NO 97
<211> LENGTH: 14
<212> TYPE: PRT
<213> ORGANISM: Artificial Sequence
<220> FEATURE:
<223> OTHER INFORMATION: Positive candidate Clone ID 226 CDR3-VH
      analysed by KABAT

<400> SEQUENCE: 97

Gly Glu Gly Leu Gly Ala Ala Arg Ser Val Ser Met Asp Tyr
1               5                   10

<210> SEQ ID NO 98
<211> LENGTH: 8
<212> TYPE: PRT
<213> ORGANISM: Artificial Sequence
<220> FEATURE:
<223> OTHER INFORMATION: Positive candidate Clone ID 226 CDR1-VH
      analysed by IMGT

<400> SEQUENCE: 98

Gly Tyr Ser Phe Thr Asn Tyr Trp
1               5

<210> SEQ ID NO 99
<211> LENGTH: 8
<212> TYPE: PRT
<213> ORGANISM: Artificial Sequence

```
<220> FEATURE:
<223> OTHER INFORMATION: Positive candidate Clone ID 226 CDR2-VH
      analysed by IMGT

<400> SEQUENCE: 99

Ile His Pro Ser Asp Ser Glu Thr
1               5

<210> SEQ ID NO 100
<211> LENGTH: 16
<212> TYPE: PRT
<213> ORGANISM: Artificial Sequence
<220> FEATURE:
<223> OTHER INFORMATION: Positive candidate Clone ID 226 CDR3-VH
      analysed by IMGT

<400> SEQUENCE: 100

Ala Arg Gly Glu Gly Leu Gly Ala Ala Arg Ser Val Ser Met Asp Tyr
1               5                   10                  15

<210> SEQ ID NO 101
<211> LENGTH: 11
<212> TYPE: PRT
<213> ORGANISM: Artificial Sequence
<220> FEATURE:
<223> OTHER INFORMATION: Positive candidate Clone ID 226 CDR1-VL
      analysed by KABAT

<400> SEQUENCE: 101

Arg Ala Ser Gln Asp Ile Ser Asn Tyr Leu Asn
1               5                   10

<210> SEQ ID NO 102
<211> LENGTH: 7
<212> TYPE: PRT
<213> ORGANISM: Artificial Sequence
<220> FEATURE:
<223> OTHER INFORMATION: Positive candidate Clone ID 226 CDR2-VL
      analysed by KABAT

<400> SEQUENCE: 102

Tyr Thr Ala Leu Leu His Ser
1               5

<210> SEQ ID NO 103
<211> LENGTH: 9
<212> TYPE: PRT
<213> ORGANISM: Artificial Sequence
<220> FEATURE:
<223> OTHER INFORMATION: Positive candidate Clone ID 226 CDR3-VL
      analysed by KABAT

<400> SEQUENCE: 103

Gln Gln Gly Asn Thr Leu Pro Trp Thr
1               5

<210> SEQ ID NO 104
<211> LENGTH: 6
<212> TYPE: PRT
<213> ORGANISM: Artificial Sequence
<220> FEATURE:
<223> OTHER INFORMATION: Positive candidate Clone ID 226 CDR1-VL
      analysed by IMGT

<400> SEQUENCE: 104

Gln Asp Ile Ser Asn Tyr
1               5
```

<210> SEQ ID NO 105
<211> LENGTH: 3
<212> TYPE: PRT
<213> ORGANISM: Artificial Sequence
<220> FEATURE:
<223> OTHER INFORMATION: Positive candidate Clone ID 226 CDR2-VL
      analysed by IMGT

<400> SEQUENCE: 105

Tyr Thr Ala
1

<210> SEQ ID NO 106
<211> LENGTH: 9
<212> TYPE: PRT
<213> ORGANISM: Artificial Sequence
<220> FEATURE:
<223> OTHER INFORMATION: Positive candidate Clone ID 226 CDR3-VL
      analysed by IMGT

<400> SEQUENCE: 106

Gln Gln Gly Asn Thr Leu Pro Trp Thr
1               5

<210> SEQ ID NO 107
<211> LENGTH: 5
<212> TYPE: PRT
<213> ORGANISM: Artificial Sequence
<220> FEATURE:
<223> OTHER INFORMATION: Positive candidate Clone ID 309 CDR1-VH
      analysed by KABAT

<400> SEQUENCE: 107

Ser Tyr Trp Ile His
1               5

<210> SEQ ID NO 108
<211> LENGTH: 17
<212> TYPE: PRT
<213> ORGANISM: Artificial Sequence
<220> FEATURE:
<223> OTHER INFORMATION: Positive candidate Clone ID 309 CDR2-VH
      analysed by KABAT

<400> SEQUENCE: 108

Glu Ile Asn Pro Asn Asn Gly Gly Thr Asp Tyr Asn Glu Lys Phe Lys
1               5                   10                  15

Arg

<210> SEQ ID NO 109
<211> LENGTH: 11
<212> TYPE: PRT
<213> ORGANISM: Artificial Sequence
<220> FEATURE:
<223> OTHER INFORMATION: Positive candidate Clone ID 309 CDR3-VH
      analysed by KABAT

<400> SEQUENCE: 109

Asp Ser Met Ile Thr Thr Thr Trp Phe Ala Tyr
1               5                   10

<210> SEQ ID NO 110
<211> LENGTH: 8
<212> TYPE: PRT
<213> ORGANISM: Artificial Sequence
<220> FEATURE:
<223> OTHER INFORMATION: Positive candidate Clone ID 309 CDR1-VH -continued analysed by IMGT

<400> SEQUENCE: 110

Gly Tyr Thr Phe Thr Ser Tyr Trp
1               5

<210> SEQ ID NO 111
<211> LENGTH: 8
<212> TYPE: PRT
<213> ORGANISM: Artificial Sequence
<220> FEATURE:
<223> OTHER INFORMATION: Positive candidate Clone ID 309 CDR2-VH
      analysed by IMGT

<400> SEQUENCE: 111

Ile Asn Pro Asn Asn Gly Gly Thr
1               5

<210> SEQ ID NO 112
<211> LENGTH: 13
<212> TYPE: PRT
<213> ORGANISM: Artificial Sequence
<220> FEATURE:
<223> OTHER INFORMATION: Positive candidate Clone ID 309 CDR3-VH
      analysed by IMGT

<400> SEQUENCE: 112

Thr Ile Asp Ser Met Ile Thr Thr Thr Trp Phe Ala Tyr
1               5                   10

<210> SEQ ID NO 113
<211> LENGTH: 11
<212> TYPE: PRT
<213> ORGANISM: Artificial Sequence
<220> FEATURE:
<223> OTHER INFORMATION: Positive candidate Clone ID 309 CDR1-VL
      analysed by KABAT

<400> SEQUENCE: 113

Lys Ala Ser Gln Asn Val Gly Thr Asn Val Ala
1               5                   10

<210> SEQ ID NO 114
<211> LENGTH: 7
<212> TYPE: PRT
<213> ORGANISM: Artificial Sequence
<220> FEATURE:
<223> OTHER INFORMATION: Positive candidate Clone ID 309 CDR2-VL
      analysed by KABAT

<400> SEQUENCE: 114

Ser Ala Ser Tyr Arg Tyr Ser
1               5

<210> SEQ ID NO 115
<211> LENGTH: 9
<212> TYPE: PRT
<213> ORGANISM: Artificial Sequence
<220> FEATURE:
<223> OTHER INFORMATION: Positive candidate Clone ID 309 CDR3-VL
      analysed by KABAT

<400> SEQUENCE: 115

Gln Gln Tyr Asn Ser Tyr Pro Phe Thr
1               5

<210> SEQ ID NO 116

```
<211> LENGTH: 6
<212> TYPE: PRT
<213> ORGANISM: Artificial Sequence
<220> FEATURE:
<223> OTHER INFORMATION: Positive candidate Clone ID 309 CDR1-VL
      analysed by IMGT

<400> SEQUENCE: 116

Gln Asn Val Gly Thr Asn
1               5

<210> SEQ ID NO 117
<211> LENGTH: 3
<212> TYPE: PRT
<213> ORGANISM: Artificial Sequence
<220> FEATURE:
<223> OTHER INFORMATION: Positive candidate Clone ID 309 CDR2-VL
      analysed by IMGT

<400> SEQUENCE: 117

Ser Ala Ser
1

<210> SEQ ID NO 118
<211> LENGTH: 9
<212> TYPE: PRT
<213> ORGANISM: Artificial Sequence
<220> FEATURE:
<223> OTHER INFORMATION: Positive candidate Clone ID 309 CDR3-VL
      analysed by IMGT

<400> SEQUENCE: 118

Gln Gln Tyr Asn Ser Tyr Pro Phe Thr
1               5

<210> SEQ ID NO 119
<211> LENGTH: 5
<212> TYPE: PRT
<213> ORGANISM: Artificial Sequence
<220> FEATURE:
<223> OTHER INFORMATION: Positive candidate Clone ID 352 CDR1-VH
      analysed by KABAT

<400> SEQUENCE: 119

Ser Tyr Gly Val His
1               5

<210> SEQ ID NO 120
<211> LENGTH: 16
<212> TYPE: PRT
<213> ORGANISM: Artificial Sequence
<220> FEATURE:
<223> OTHER INFORMATION: Positive candidate Clone ID 352 CDR2-VH
      analysed by KABAT

<400> SEQUENCE: 120

Val Ile Trp Ser Asp Gly Gly Thr Thr Tyr Asn Ser Ala Leu Lys Ser
1               5                   10                  15

<210> SEQ ID NO 121
<211> LENGTH: 11
<212> TYPE: PRT
<213> ORGANISM: Artificial Sequence
<220> FEATURE:
<223> OTHER INFORMATION: Positive candidate Clone ID 352 CDR3-VH
      analysed by KABAT

<400> SEQUENCE: 121
```

His Asp Asp Asp Gly Tyr Tyr Ala Met Asp Tyr
1               5                   10

<210> SEQ ID NO 122
<211> LENGTH: 8
<212> TYPE: PRT
<213> ORGANISM: Artificial Sequence
<220> FEATURE:
<223> OTHER INFORMATION: Positive candidate Clone ID 352 CDR1-VH
      analysed by IMGT

<400> SEQUENCE: 122

Gly Phe Ser Leu Thr Ser Tyr Gly
1               5

<210> SEQ ID NO 123
<211> LENGTH: 7
<212> TYPE: PRT
<213> ORGANISM: Artificial Sequence
<220> FEATURE:
<223> OTHER INFORMATION: Positive candidate Clone ID 352 CDR2-VH
      analysed by IMGT

<400> SEQUENCE: 123

Ile Trp Ser Asp Gly Gly Thr
1               5

<210> SEQ ID NO 124
<211> LENGTH: 13
<212> TYPE: PRT
<213> ORGANISM: Artificial Sequence
<220> FEATURE:
<223> OTHER INFORMATION: Positive candidate Clone ID 352 CDR3-VH
      analysed by IMGT

<400> SEQUENCE: 124

Ala Arg His Asp Asp Asp Gly Tyr Tyr Ala Met Asp Tyr
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Positive candidate Clone ID 352 CDR1-VL
      analysed by KABAT

<400> SEQUENCE: 125

Ser Ala Ser Ser Ser Val Gly Tyr Met Tyr
1               5                   10

<210> SEQ ID NO 126
<211> LENGTH: 7
<212> TYPE: PRT
<213> ORGANISM: Artificial Sequence
<220> FEATURE:
<223> OTHER INFORMATION: Positive candidate Clone ID 352 CDR2-VL
      analysed by KABAT

<400> SEQUENCE: 126

Leu Thr Ser Asn Leu Ala Ser
1               5

<210> SEQ ID NO 127
<211> LENGTH: 9
<212> TYPE: PRT
<213> ORGANISM: Artificial Sequence
<220> FEATURE:

```
<223> OTHER INFORMATION: Positive candidate Clone ID 352 CDR3-VL
      analysed by KABAT

<400> SEQUENCE: 127

Gln Gln Trp Ser Ser Asp Pro Phe Thr
1               5

<210> SEQ ID NO 128
<211> LENGTH: 5
<212> TYPE: PRT
<213> ORGANISM: Artificial Sequence
<220> FEATURE:
<223> OTHER INFORMATION: Positive candidate Clone ID 352 CDR1-VL
      analysed by IMGT

<400> SEQUENCE: 128

Ser Ser Val Gly Tyr
1               5

<210> SEQ ID NO 129
<211> LENGTH: 3
<212> TYPE: PRT
<213> ORGANISM: Artificial Sequence
<220> FEATURE:
<223> OTHER INFORMATION: Positive candidate Clone ID 352 CDR2-VL
      analysed by IMGT

<400> SEQUENCE: 129

Leu Thr Ser
1

<210> SEQ ID NO 130
<211> LENGTH: 9
<212> TYPE: PRT
<213> ORGANISM: Artificial Sequence
<220> FEATURE:
<223> OTHER INFORMATION: Positive candidate Clone ID 352 CDR3-VL
      analysed by IMGT

<400> SEQUENCE: 130

Gln Gln Trp Ser Ser Asp Pro Phe Thr
1               5

<210> SEQ ID NO 131
<211> LENGTH: 5
<212> TYPE: PRT
<213> ORGANISM: Artificial Sequence
<220> FEATURE:
<223> OTHER INFORMATION: Positive candidate Clone ID 365 CDR1-VH
      analysed by KABAT

<400> SEQUENCE: 131

Ser Tyr Gly Val His
1               5

<210> SEQ ID NO 132
<211> LENGTH: 16
<212> TYPE: PRT
<213> ORGANISM: Artificial Sequence
<220> FEATURE:
<223> OTHER INFORMATION: Positive candidate Clone ID 365 CDR2-VH
      analysed by KABAT

<400> SEQUENCE: 132

Leu Ile Trp Ser Asp Gly Ser Pro Asp Tyr Ser Ala Ala Phe Ile Ser
1               5                   10                  15
```

```
<210> SEQ ID NO 133
<211> LENGTH: 11
<212> TYPE: PRT
<213> ORGANISM: Artificial Sequence
<220> FEATURE:
<223> OTHER INFORMATION: Positive candidate Clone ID 365 CDR3-VH
      analysed by KABAT

<400> SEQUENCE: 133

Asn Asp Asp Gly Gly Asp Tyr Val Met Asp Tyr
1               5                   10

<210> SEQ ID NO 134
<211> LENGTH: 8
<212> TYPE: PRT
<213> ORGANISM: Artificial Sequence
<220> FEATURE:
<223> OTHER INFORMATION: Positive candidate Clone ID 365 CDR1-VH
      analysed by IMGT

<400> SEQUENCE: 134

Gly Phe Ser Leu Thr Ser Tyr Gly
1               5

<210> SEQ ID NO 135
<211> LENGTH: 7
<212> TYPE: PRT
<213> ORGANISM: Artificial Sequence
<220> FEATURE:
<223> OTHER INFORMATION: Positive candidate Clone ID 365 CDR2-VH
      analysed by IMGT

<400> SEQUENCE: 135

Ile Trp Ser Asp Gly Ser Pro
1               5

<210> SEQ ID NO 136
<211> LENGTH: 13
<212> TYPE: PRT
<213> ORGANISM: Artificial Sequence
<220> FEATURE:
<223> OTHER INFORMATION: Positive candidate Clone ID 365 CDR3-VH
      analysed by IMGT

<400> SEQUENCE: 136

Ala Arg Asn Asp Asp Gly Gly Asp Tyr Val Met Asp Tyr
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Positive candidate Clone ID 365 CDR1-VL
      analysed by KABAT

<400> SEQUENCE: 137

Ser Ala Ser Ser Ser Val Ser Tyr Met Tyr
1               5                   10

<210> SEQ ID NO 138
<211> LENGTH: 7
<212> TYPE: PRT
<213> ORGANISM: Artificial Sequence
<220> FEATURE:
<223> OTHER INFORMATION: Positive candidate Clone ID 365 CDR2-VL
      analysed by KABAT

<400> SEQUENCE: 138
```

```
Leu Thr Ser Asn Leu Ala Ser
1               5

<210> SEQ ID NO 139
<211> LENGTH: 9
<212> TYPE: PRT
<213> ORGANISM: Artificial Sequence
<220> FEATURE:
<223> OTHER INFORMATION: Positive candidate Clone ID 365 CDR3-VL
      analysed by KABAT

<400> SEQUENCE: 139

Gln Gln Trp Thr Ser Asn Pro Leu Thr
1               5

<210> SEQ ID NO 140
<211> LENGTH: 5
<212> TYPE: PRT
<213> ORGANISM: Artificial Sequence
<220> FEATURE:
<223> OTHER INFORMATION: Positive candidate Clone ID 365 CDR1-VL
      analysed by IMGT

<400> SEQUENCE: 140

Ser Ser Val Ser Tyr
1               5

<210> SEQ ID NO 141
<211> LENGTH: 3
<212> TYPE: PRT
<213> ORGANISM: Artificial Sequence
<220> FEATURE:
<223> OTHER INFORMATION: Positive candidate Clone ID 365 CDR2-VL
      analysed by IMGT

<400> SEQUENCE: 141

Leu Thr Ser
1

<210> SEQ ID NO 142
<211> LENGTH: 9
<212> TYPE: PRT
<213> ORGANISM: Artificial Sequence
<220> FEATURE:
<223> OTHER INFORMATION: Positive candidate Clone ID 365 CDR3-VL
      analysed by IMGT

<400> SEQUENCE: 142

Gln Gln Trp Thr Ser Asn Pro Leu Thr
1               5

<210> SEQ ID NO 143
<211> LENGTH: 5
<212> TYPE: PRT
<213> ORGANISM: Artificial Sequence
<220> FEATURE:
<223> OTHER INFORMATION: Positive candidate Clone ID 395 CDR1-VH
      analysed by KABAT

<400> SEQUENCE: 143

Ser Tyr Ser Val His
1               5

<210> SEQ ID NO 144
<211> LENGTH: 16
<212> TYPE: PRT
<213> ORGANISM: Artificial Sequence
```

```
<220> FEATURE:
<223> OTHER INFORMATION: Positive candidate Clone ID 395 CDR2-VH
      analysed by KABAT

<400> SEQUENCE: 144

Val Ile Trp Ser Asp Gly Gly Thr Asp Tyr Ser Ala Ala Phe Ile Ser
1               5                   10                  15

<210> SEQ ID NO 145
<211> LENGTH: 11
<212> TYPE: PRT
<213> ORGANISM: Artificial Sequence
<220> FEATURE:
<223> OTHER INFORMATION: Positive candidate Clone ID 395 CDR3-VH
      analysed by KABAT

<400> SEQUENCE: 145

Asn Asp Asp Gly Gly Asp Tyr Ala Met Asp Tyr
1               5                   10

<210> SEQ ID NO 146
<211> LENGTH: 8
<212> TYPE: PRT
<213> ORGANISM: Artificial Sequence
<220> FEATURE:
<223> OTHER INFORMATION: Positive candidate Clone ID 395 CDR1-VH
      analysed by IMGT

<400> SEQUENCE: 146

Gly Phe Ser Leu Thr Ser Tyr Ser
1               5

<210> SEQ ID NO 147
<211> LENGTH: 7
<212> TYPE: PRT
<213> ORGANISM: Artificial Sequence
<220> FEATURE:
<223> OTHER INFORMATION: Positive candidate Clone ID 395 CDR2-VH
      analysed by IMGT

<400> SEQUENCE: 147

Ile Trp Ser Asp Gly Gly Thr
1               5

<210> SEQ ID NO 148
<211> LENGTH: 13
<212> TYPE: PRT
<213> ORGANISM: Artificial Sequence
<220> FEATURE:
<223> OTHER INFORMATION: Positive candidate Clone ID 395 CDR3-VH
      analysed by IMGT

<400> SEQUENCE: 148

Ala Arg Asn Asp Asp Gly Gly Asp Tyr Ala Met Asp Tyr
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Positive candidate Clone ID 395 CDR1-VL
      analysed by KABAT

<400> SEQUENCE: 149

Ser Ala Ser Ser Ser Val Ser Tyr Met Tyr
1               5                   10
```

<210> SEQ ID NO 150
<211> LENGTH: 7
<212> TYPE: PRT
<213> ORGANISM: Artificial Sequence
<220> FEATURE:
<223> OTHER INFORMATION: Positive candidate Clone ID 395 CDR2-VL
      analysed by KABAT

<400> SEQUENCE: 150

Leu Thr Ser Asn Leu Ala Ser
1               5

<210> SEQ ID NO 151
<211> LENGTH: 9
<212> TYPE: PRT
<213> ORGANISM: Artificial Sequence
<220> FEATURE:
<223> OTHER INFORMATION: Positive candidate Clone ID 395 CDR3-VL
      analysed by KABAT

<400> SEQUENCE: 151

Gln Gln Trp Ser Ser Asn Pro Leu Thr
1               5

<210> SEQ ID NO 152
<211> LENGTH: 5
<212> TYPE: PRT
<213> ORGANISM: Artificial Sequence
<220> FEATURE:
<223> OTHER INFORMATION: Positive candidate Clone ID 395 CDR1-VL
      analysed by IMGT

<400> SEQUENCE: 152

Ser Ser Val Ser Tyr
1               5

<210> SEQ ID NO 153
<211> LENGTH: 3
<212> TYPE: PRT
<213> ORGANISM: Artificial Sequence
<220> FEATURE:
<223> OTHER INFORMATION: Positive candidate Clone ID 395 CDR2-VL
      analysed by IMGT

<400> SEQUENCE: 153

Leu Thr Ser
1

<210> SEQ ID NO 154
<211> LENGTH: 9
<212> TYPE: PRT
<213> ORGANISM: Artificial Sequence
<220> FEATURE:
<223> OTHER INFORMATION: Positive candidate Clone ID 395 CDR3-VL
      analysed by IMGT

<400> SEQUENCE: 154

Gln Gln Trp Ser Ser Asn Pro Leu Thr
1               5